(12) United States Patent
Limanto et al.

(10) Patent No.: US 9,006,460 B2
(45) Date of Patent: Apr. 14, 2015

(54) PROCESS FOR PREPARING AMINOCYCLOHEXYL ETHER COMPOUNDS

(75) Inventors: John Limanto, Rahway, NJ (US); Gregory L. Beutner, Green Brook, NJ (US); Jingjun Yin, Green Brook, NJ (US); Artis Klapars, Edison, NJ (US); Eric R. Ashley, Fanwood, NJ (US); Hallena R. Strotman, Somerset, NJ (US); Matthew D. Truppo, Bradley Beach, NJ (US); Cheol K. Chung, Westfield, NJ (US); Gregory Hughes, Scotch Plains, NJ (US); Zhijian Liu, Kendall Park, NJ (US); Brendan Grau, Warrington, NJ (US); Jacob Janey, New York, NY (US)

(73) Assignee: Cardiome International AG, Zug (CH)

( * ) Notice: Subject to any disclaimer, the term of this patent is extended or adjusted under 35 U.S.C. 154(b) by 0 days.

(21) Appl. No.: 13/817,274

(22) PCT Filed: Aug. 8, 2011

(86) PCT No.: PCT/US2011/046885
§ 371 (c)(1),
(2), (4) Date: Feb. 15, 2013

(87) PCT Pub. No.: WO2012/024100
PCT Pub. Date: Feb. 23, 2012

(65) Prior Publication Data
US 2013/0149751 A1  Jun. 13, 2013

Related U.S. Application Data

(60) Provisional application No. 61/373,966, filed on Aug. 16, 2010, provisional application No. 61/510,213, filed on Jul. 21, 2011.

(51) Int. Cl.
*C07D 207/12* (2006.01)
*C12P 17/10* (2006.01)

(52) U.S. Cl.
CPC ............... *C12P 17/10* (2013.01); *C07D 207/12* (2013.01)

(58) Field of Classification Search
CPC ............................. C07D 207/12; C12P 17/10
USPC ........................................................ 548/556
See application file for complete search history.

(56) References Cited

U.S. PATENT DOCUMENTS

| 3,328,432 | A  | * | 6/1967 | Kieser et al. ................. 552/511 |
| 6,537,746 | B2 |   | 3/2003 | Arnold et al. |
| 7,169,592 | B2 |   | 1/2007 | Yamada et al. |
| 2006/0195947 | A1 |   | 8/2006 | Davis et al. |
| 2008/0213845 | A1 |   | 9/2008 | Fotheringham et al. |
| 2010/0152464 | A1 | * | 6/2010 | Plouvier et al. ............... 548/544 |
| 2010/0209981 | A1 | * | 8/2010 | Dhawan et al. ............... 435/128 |

FOREIGN PATENT DOCUMENTS

| WO | 9319056 | 9/1993 |
| WO | 9508544 | 3/1995 |
| WO | 9522625 | 8/1995 |
| WO | 9700078 | 1/1997 |
| WO | 9735966 | 10/1997 |
| WO | 9827230 | 6/1998 |
| WO | 9950225 | 10/1999 |
| WO | 0042651 | 7/2000 |
| WO | 0175767 | 10/2001 |
| WO | 2004099137 | 11/2004 |
| WO | 2006075778 | 7/2006 |
| WO | 2006088525 | 8/2006 |
| WO | WO2006/088525 | * 8/2006 ............ C07C 213/02 |
| WO | 2006138673 | 12/2006 |
| WO | 2010081053 | 7/2010 |
| WO | 2010099501 | 9/2010 |

OTHER PUBLICATIONS

Iwasaki et al. (Appl Microbiol Biotechnol (2012) 93:1563-1573).*
International Search Report for PCT/US11/46885, Mailed Feb. 13, 2014, 3 pages, US.
Limanto et al., A Highly Efficient Asymmetric Synthesis of Vernakalant, Organic Letters, Apr. 4, 2014, pp. A-D, ACS Pulbications, US.
Al-Zoubi et al., Direct and Waste-Free Amidations and Cycloadditionas by Organocatalytic Activation of Carboxylic Acids at Room Temperature, Angewandte Chemie International, Edition 2008, v.47, pp. 2876-2879, US.
Arnold et al., To Catalyze or not to Catalyze? Insight into Direct Amide Bond Formation from Amines and Carboxylic Acids under Thermal and Catalyzed Conditions, 2006, Adv. Synth. Catalog, v.348, pp. 813-820, US.
Arnold et al., Synthesis, evaluation and application of novel bifunctional N,N-di-isopropylbenzylamineboronic acid catalyst for direct amide formation between carboxylic acids and amines, Green Chemistry, 2008, v.10, pp. 124-134, US.

(Continued)

*Primary Examiner* — Robert Havlin

(57) ABSTRACT

The present invention relates to a process for preparing aminocyclohexyl ether compounds of Formula I: or the pharmaceutically acceptable salts and esters thereof. In particular, the instant invention is directed towards a process for preparing (1R,2R)-2-[(3R)-Hydroxypyrrolidinyl]-1-(3,4-dimethoxyphenethoxy)-cyclohexane as well as various intermediates.

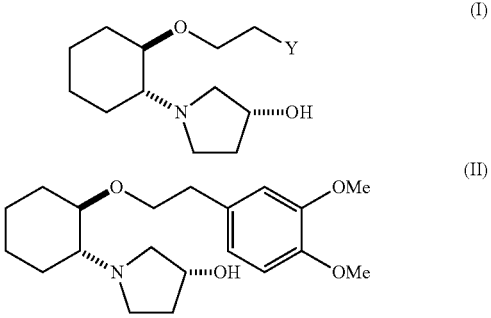

18 Claims, 2 Drawing Sheets

(56) References Cited

OTHER PUBLICATIONS

Bai et al., Enantioselective Synthesis of Chiral β-Aryloxy Alcohols by Ruthenium-Catalyzed Ketone Hydrogenation via Dynamic Kinetic Resolution (DKR), Adv. Synth. Catal., Dec. 2009, v.352, pp. 81-84, US.

Blazejewski et al., Enamines A Halogene Allylique-II Action Des Organometalliques, Tetrahedron, 1973, v.29, pp. 4233-4239, GB.

Brown et al., Organoboranes for Synthesis. 1. Protonolysis of Trialkylboranes, A Convenient Non-Catalytic Conversion of Alkenes into Saturated Compounds via Hydroboration-Protonolysis, Tetrahedron, 1986, v.42, No. 20, pp. 5497-5504, US.

Charville et al., The thermal and boron-catalysed direct amide formation reactions: mechanistically understudied yet important processes, ChemComm, 2010, v.46, pp. 1813-1823, US.

Chung et al., Process Development of C—N Cross-Coupling and Enantioselective Biocatalytic Reactions for the Asymmetric Synthesis of Niraparib, Organic Process Research & Development, 2014, v.18, pp. 215-227, US.

Cuetos et al., Expanding dynamic kinetic protocols: transaminase-catalyzed synthesis of α-substituted β-amino ester derivatives, Chemical Communications, 2013, v. 49, pp. 10688-10690.

Georgiou et al., Synthesis of Aminoboronic Acids and Their Applications in Bifunctional Catalysis, Accounts of Chemical Research, 2009, v. 42, pp. 756-768.

Hohne et al., Efficient Asymmetric Synthesis of Chiral Amines by Combining Transaminase and Pyruvate Decarboxylase, ChemBioChem, 2008, v. 9, pp. 363-365.

Ishihara et al., 3,4,5-Trifluorobenzeneboronic Acid as an Extremely Active Amidation Catalyst, Journal of Organic Chemistry, 1996, v. 61, pp. 4196-4197.

Ishihara et al., 3,5-Bis(perfluorodecyl)phenylboronic Acid as an Easily Recyclable Direct Amide Condensation Catalyst, Synlett, 2001, No. 9, pp. 1371-1374.

Iwasaki et al., Microbial synthesis of chiral amines by (R)-specific transamination with Arthrobacter sp. KNK168, Biotechnological Products and Process Engineering, 2006, v. 69, pp. 499-505.

Johnson et al., Industrial-Scale Synthesis and Applications of Asymmetric Hydrogenation Catalysts, Accounts Chemical Research, 2007, v. 40, pp. 1291-1299.

Koszelewski et al., Asymmetric Synthesis of Optically Pure Pharmacologically Relevant Amines Employing ω-Transaminases, Advanced Synthesis and Catalysis, 2008, v. 350, pp. 2761-2766.

Koszelewski et al., Deracemisation of α-Chiral Primary Amines by a One-Pot, Two-Step Cascade Reaction Catalysed by ω-Transaminases, European Journal of Organic Chemistry, 2009, pp. 2289-2292.

Koszelewski et al., Synthesis of 4-phenylpyrrolidin-2-one via dynamic kinetic resolution catalyzed by ω-transaminases, Journal of Molecular Catalysis B: Enzymatic, 2009, v. 60, pp. 191-194.

Koszelewski et al., Formal Asymmetric Biocatalytic Reductive Amination, Angewandte Chemie International, Edition 2008, v. 47, pp. 9337-9340.

Maki et al., N-Alkyl-4-boronopyridinium Halides versus Boric Acid as Catalysts for the Esterification of α-Hydroxycarboxylic Acids, Organic Letters, 2005, v. 7, pp. 5047-5050.

Maki et al., New boron(III)-catalyzed amide and ester condensation reactions, Tetrahedron, 2007, v. 63, pp. 8645-8657.

Martin-Matute et al., Dynamic kinetic resolution catalyzed by enzymes and metals, Opinions in Chemical Biology, 2007, v. 11, pp. 226-232.

Peng et al., Development of a Concise, Asymmetric Synthesis of a Smoothened Receptor (SMO) Inhibitor: Enzymatic Transamination of a 4-Piperidinone with Dynamic Kinetic Resolution, Organic Letters, 2014, v. 16, pp. 860-863.

Reddy et al., Lewis Acid and Hexamethyldisilazane-Promoted Efficient Synthesis of N-Alkyl- and N-Arylimide Derivatives, Journal of Organic Chemistry, 1997, v. 62, pp. 2652-2654.

Savile et al., Biocatalytic Asymmetric Synthesis of Chiral Amines from Ketones Applied to Sitagliptin Manufacture, Science, 2010, v. 329, pp. 305-309.

Shin et al., Exploring the Active Site of Amine:Pyruvate Aminotransferase on the Basis of the Substrate Structure-Reactivity Relationship: How the Enzyme Controls Substrate Specificity and Stereoselectivity, Journal of Organic Chemistry, 2002, v. 67, pp. 2848-2853.

Truppo et al., Efficient kinetic resolution of racemic amines using a transaminase in combination with an amino acis oxidase, Chemical Communication, 2009, pp. 2127-2129.

Truppo et al., Rapid screening and scale-up of transminase catalysed reactions, Organic and Biomolecular Chemistry, 2008, v. 7, pp. 395-398.

Vizzardi et al., A New Antiarrhythmic Drug in the Treatment of Recent-Onset Atrial Fibrillation: Vernakalant, Cardiovascular Therapeutics, 2013, v. 31, pp. E55-E62.

Yamashita et al., Primary Alkylboronic Acids as Highly Active Catalysts for the Dehydrative Amide Condensation of α-Hydroxycarboxylic Acids, Organic Letters, 2013, v. 15, pp. 3654-3657.

Ye et al., New Procedure for the Preparation of (1R,2R)-2-[(R)-3-(Benzyloxy)pry-rolidin-1-yl]cyclohexanol, Synthesis, 2012, v. 44, pp. 51-56.

* cited by examiner

SEQUENCE LISTING

```
<160> NUMBER OF SEQ ID NOS: 102

<210> SEQ ID NO 1
<211> LENGTH: 993
<212> TYPE: DNA
<213> ORGANISM: Arthrobacter sp. KNK168

<400> SEQUENCE: 1
atggcattca gcgccgatac ctccgagatc gtctacacgc acgacaccgg cctcgactac      60
atcacttata gcgactacga actcgatcct gctaacccgc tcgcgggagg tgcggcatgg     120
atcgagggtg cattcgtgcc gccgtcggag gcgcggatct cgatcttcga tcagggttac     180
ctccactcgg acgtcaccta cacggtcttc cacgtctgga acggaaatgc attccgcctc     240
gacgaccaca tcgaacgcct cttctccaac gcggagtcga tgcgcatcat ccctccgctc     300
acacaggacg aagtgaagga gattgcgctc gaactcgtcg cgaagaccga attgcgtgag     360
gccttcgtgt ccgtgtcgat tacccgcggt tacagctcga ctccgggcga gcgcgacatc     420
acgaagcacc gcccgcaggt gtacatgtat gccgtcccat atcagtggat cgtgccgttt     480
gaccgaattc gcgacggcgt gcacgccatg gtcgcacaga gcgtgcgccg aacccgcgc     540 agctcgatcg accctcaggt caagaacttc cagtgggggg atctgatccg tgcggttcaa     600
gagacgcacg accgcgggtt cgaggctccc cttctgctcg acggcgatgg actgcttgcc     660
gagggctcgg ggttcaacgt cgtcgtgatc aaggacggcg tcgtgcgcag cccgggtcga     720
```

-continued

```
gcggcgctcc ccggcattac gcggaagacc gtgctcgaga tcgccgaatc gctcggacac    780
gaggcgattc tcgccgacat cacgctcgct gaactgctcg acgccgacga agtgctcggc    840
tgcacgactg cgggcggagt gtggccattc gtcagcgtgg acggcaaccc catctcggac    900
ggggttcccg gccccatcac ccagtcgatc atccgtcgtt actgggagct gaatgtcgag    960
agctcgtcgt tgcttacgcc tgtgcagtac tga                                993
```

<210> SEQ ID NO 2
<211> LENGTH: 330
<212> TYPE: PRT
<213> ORGANISM: Arthrobacter sp. KNK168

<400> SEQUENCE: 2

```
Met Ala Phe Ser Ala Asp Thr Ser Glu Ile Val Tyr Thr His Asp Thr
  1               5                  10                  15

Gly Leu Asp Tyr Ile Thr Tyr Ser Asp Tyr Glu Leu Asp Pro Ala Asn
                 20                  25                  30

Pro Leu Ala Gly Gly Ala Ala Trp Ile Glu Gly Ala Phe Val Pro Pro
             35                  40                  45

Ser Glu Ala Arg Ile Ser Ile Phe Asp Gln Gly Tyr Leu His Ser Asp
         50                  55                  60

Val Thr Tyr Thr Val Phe His Val Trp Asn Gly Asn Ala Phe Arg Leu
 65                  70                  75                  80

Asp Asp His Ile Glu Arg Leu Phe Ser Asn Ala Glu Ser Met Arg Ile
                 85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Phe Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Ser Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Ala Gly Gly Val Trp
        275                 280                 285

Pro Phe Val Ser Val Asp Gly Asn Pro Ile Ser Asp Gly Val Pro Gly
    290                 295                 300

Pro Ile Thr Gln Ser Ile Arg Arg Tyr Trp Glu Leu Asn Val Glu
305                 310                 315                 320
```

Ser Ser Ser Leu Leu Thr Pro Val Gln Tyr
            325                 330

<210> SEQ ID NO 3
<211> LENGTH: 993
<212> TYPE: DNA
<213> ORGANISM: Artificial Sequence
<220> FEATURE:
<223> OTHER INFORMATION: Engineered variant of Arthrobacter transaminase

<400> SEQUENCE: 3

```
atggctttct ctgctgacac ctctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggttac     180
ctgcactctg acgttaccta caccgttttc acgtttgga acggtaacgc tttccgtctg      240
gacgaccaca tcgaacgtct gttctctaac gctgaatcta tgcgtatcat cccgccgctg     300
acccaggacg aagttaaaga aatcgctctg gaactggttg ctaaaaccga actgcgtgaa     360
gcattcgttt ctgtttctat cacccgtggt tactcttcta ccccaggtga acgtgacatc     420
accaaacatc gtccgcaggt ttacatgtac gctgttccgt accagtggat cgtaccgttt     480
gaccgcatcc gtgacggtgt tcacgctatg gttgctcagt ctgttcgtcg tactccgcgt     540
tcttctatcg acccgcaggt taaaaacttc cagtggggtg acctgatccg tgcagttcag     600
gaaacccacg accgtggttt cgaagctccg ctgctgctgg acggtgacgg tctgctggct     660
gaaggttctg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccctggct gaactgctgg acgctgacga agttctgggt     840
tgcactaccg ctggtggtgt ttggccgttc gtttctgttg acggtaaccc gatctctgac     900
ggtgttccgg tccggttac ccagtctatc atccgtcgtt actgggaact gaacgttgaa     960
tcttcttctc tgctgacccc ggtacagtac tga                                   993
```

<210> SEQ ID NO 4
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 4

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Val Thr Tyr Thr Val Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Phe Val Ser Val Ser Ile Thr

|     |     |     |     | 115 |     |     |     |     | 120 |     |     |     |     | 125 |     |
| --- | --- | --- | --- | --- | --- | --- | --- | --- | --- | --- | --- | --- | --- | --- | --- |

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Ser Gly
210                 215                 220

Phe Asn Val Val Val Ile Lys Asp Gly Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Ala Gly Gly Val Trp
        275                 280                 285

Pro Phe Val Ser Val Asp Gly Asn Pro Ile Ser Asp Gly Val Pro Gly
290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330

```
<210> SEQ ID NO 5
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 5
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccaccttc acgtttgga acgtaacgc tttccgtctg       240 ggggaccaca tcgaacgtct gttctctaat gcggaatcta ttcgtttgat cccgccgctg     300
acccaggaca agttaaaga gatcgctctg gaactggttg ctaaaaccga actgcgtgaa      360
gcgatcgttt ctgtttctat cacccgtggt tactcttcta ccccattcga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagctgccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat cacccccggct gaactgtacg acgctgacga agttctgggt     840
```

```
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                      990
```

<210> SEQ ID NO 6
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 6

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 7
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 7

```
atggctttct cagctgacac ccctgaaatc gtttacaccc acgacaccgg tttggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccaccttc acgtttgga acggtaacgc tttccgtctg      240
ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
gcgatcgttg tcgttttctat cacccgtggt tactcttcta ccccatggga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagttatcg ctgctgctgg actgcgacaa cctgctggct     660
gaaggtccgg gttcaacgt tgttgttatc aaagacggtg ttgttcgttc tccgggtcgt      720
gctgccctgc cgggtatcac ccgtaaaacc gttctggaaa tcgctgaatc tctgggtcac     780
gaagctatcc tggctgacat caccccggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                      990
```

<210> SEQ ID NO 8
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 8

```
Met Ala Phe Ser Ala Asp Thr Pro Glu Ile Val Tyr Thr His Asp Thr
  1               5                  10                  15

Gly Leu Asp Tyr Ile Thr Tyr Ser Asp Tyr Glu Leu Asp Pro Ala Asn
             20                  25                  30

Pro Leu Ala Gly Gly Ala Ala Trp Ile Glu Gly Ala Phe Val Pro Pro
         35                  40                  45

Ser Glu Ala Arg Ile Ser Ile Phe Asp Gln Gly Phe Tyr Thr Ser Asp
     50                  55                  60

Ala Thr Tyr Thr Thr Phe His Val Trp Asn Gly Asn Ala Phe Arg Leu
 65                  70                  75                  80

Gly Asp His Ile Glu Arg Leu Phe Ser Asn Ala Glu Ser Ile Arg Leu
                 85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Val Ser Ile Thr
        115                 120                 125

Arg Gly Tyr Ser Ser Thr Pro Trp Glu Arg Asp Ile Thr Lys His Arg
```

```
                    130                 135                 140
Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
            195                 200                 205

Leu Ser Leu Leu Leu Asp Cys Asp Asn Leu Leu Ala Glu Gly Pro Gly
        210                 215                 220

Phe Asn Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 9
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 9
atggctttct cagctgacac ccctgaaatc gtttacaccc acgacaccgg ccttgactat     60
atcacctact ctgactacga actggacccg gctaacccgc tggctggtgg tgctgcttgg    120
atcgaaggtg ctttcgttcc gccgtctgaa gctcgtatct ctatcttcga ccagggtttt    180
tatacttctg acgctaccta caccgtcttc cacgtttgga acggtaacgc tttccgtctg    240
ggggaccaca tcgaacgtct gttctctaat gcggaatcta ttcgtttgat cccgccgctg    300
acccaggacg aagttaaaga tcgctctctg gaactggttg ctaaaaccga actgcgtgaa    360
gcgatcgttt ctgtttctat caccgtgggt tactcttcta ccccatggga gcgtgacatc    420
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagctgccg ctgctgctgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatt cctgggtcac    780
gaagctatcc tggctgacat cacccccggct gaactgtacg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
```
ccttcttctc tgctgacccc ggtacagtac					990

<210> SEQ ID NO 10
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 10

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Trp Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Phe Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 11
<211> LENGTH: 990

<212> TYPE: DNA
<213> ORGANISM: Artificial Sequence
<220> FEATURE:
<223> OTHER INFORMATION: Engineered variant of Arthrobacter transaminase

<400> SEQUENCE: 11

```
atggctttct cagctgacac ccctgaaatc gtttacaccc acgacaccgg tctggactat      60
atcacctact ctgactacga accggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccgtcttc cacgtttgga acggtaacgc tttccgtctg     240
ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
gcgatcgttt ctgtttctat cacccgtggt tactcttcta ccccatggga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagttaccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccccggct gaactgtacg acgctgacga agttctgggt     840
tgctcaaccg tggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                       990
```

<210> SEQ ID NO 12
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 12

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Pro Asp Pro Ala Asn
                20                  25                  30

Pro Leu Ala Gly Gly Ala Ala Trp Ile Glu Gly Ala Phe Val Pro Pro
            35                  40                  45

Ser Glu Ala Arg Ile Ser Ile Phe Asp Gln Gly Phe Tyr Thr Ser Asp
        50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Trp Glu Arg Asp Ile Thr Lys His Arg
    130                 135                 140

Pro Gln Val Tyr Met Tyr Ala Val Pro Tyr Gln Trp Ile Val Pro Phe
```

```
            145                 150                 155                 160
Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
                195                 200                 205

Leu Pro Leu Leu Leu Asp Cys Asp Asn Leu Leu Ala Glu Gly Pro Gly
        210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 13
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 13
atggctttct cagctgacac ccctgaaatc gtttacaccc gcacaccgg tctggactat      60 atcacctact ctgactacga actggacccg gctaacccgc tggctggtgg tgctgcttgg     120
atcgaaggtg ctttcgttcc gccgtctgaa gctcgtatct ctatctccga ccagggtttt    180
tatacttctg acgctaccta caccgtcttc cacgtttgga acggtaacgc tttccgtctg    240
ggggaccaca tcgaacgtct gttctctaat gcggaatcta ttcgtttgat cccgccgctg    300
acccaggacg aagttaaaga gatcgctctg gaactggttg ctaaaaccga actgcgtgaa    360
gcgatcgttt ctgtttctat cacccgtggt tactcttcta ccccatggga gcgtgacatc    420
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagctgccg ctgctgctgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tgactgacat caccccggct gaactgtacg acgcagacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                     990
```

<210> SEQ ID NO 14
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 14

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Ser Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Trp Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Thr Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 15
<211> LENGTH: 990
<212> TYPE: DNA
<213> ORGANISM: Artificial Sequence
<220> FEATURE:

<223> OTHER INFORMATION: Engineered variant of Arthrobacter transaminase

<400> SEQUENCE: 15

```
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccgtcttc acgtttgga acggtaacgc tttccgtctg      240
ggggaccaca tcgaacgtct gttctctaat gcggaatcta ttcgttttga cccgccgctg     300
acccaggacg aagttaaaga gatcgctctg gaactggttg ctaaaaccga actgcgtgaa     360
gcgatcgttt ctgtttctat cacccgtggt tactcttcta ccccatggga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagctgccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccccggct gaactgtacg acgctgacga agttctgggt     840
tgctcaaccg tggtggtgt ttggccgttc gtttctgttg acggtaactc tatctctgac     900
ggtgttccgg tccggttac ccagtctatc atccgtcgtt actgggaact gaacgttgaa     960
ccttcttctc tgctgacccc ggtacagtac                                      990
```

<210> SEQ ID NO 16
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 16

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Trp Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
```

```
                 165                 170                 175
Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
            195                 200                 205

Leu Pro Leu Leu Leu Asp Cys Asp Asn Leu Leu Ala Glu Gly Pro Gly
            210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
                260                 265                 270

Tyr Asp Ala Asp Glu Val Leu Gly Cys Ser Thr Gly Gly Gly Val Trp
                275                 280                 285

Pro Phe Val Ser Val Asp Gly Asn Ser Ile Ser Asp Gly Val Pro Gly
            290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

```
<210> SEQ ID NO 17
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 17
atggctttct cagctgacac ccctgaaatc gtttacaccc acgacaccgg tctggactat    60
atcacctact ctgactacga actggacccg gctaacccgc tggctggtgg tgctgcttgg   120
atcgaaggtg ctttcgttcc gccgtctgaa gctcgtatct ctatcttcga ccagggtttt   180
tatacttctg acgctaccta caccgtcttc acgtttgga acgtaacgc tttccgtctg   240
ggggaccaca tcgaacgtct gttctctaat gcggaatcta ttcgttttgat cccgccgctg   300
acccaggacg aagttaaaga gatcgctctg gaactggttg ctaaaaccga actgcgtgaa   360
gcgatcgtta tcgtttctat cacccgtggt tactcttcta ccccatggga gcgtgacatc   420
accaaacatc gtccgcaggt ttacatgtat gctgttccgt accagtggat cgtaccgttt   480
gaccgcatcc gtgacggtgt tcacctgatg gttgctcagt cagttcgtcg tacaccgcgt   540
agctctatcg acccgcaggt taaaaacttc cagtggggtg acctgatccg tgcaattcag   600
gaaacccacg accgtggttt cgagctgccg ctgctgctgg actgcgacaa cctgctggct   660
gaaggtccgg gtttcaacgt tgttgttatc aaagacggtg ttgttcgttc tccgggtcgt   720
gctgctctgc cgggtatcac ccgtaaaacc gttctggaaa tcgctgaatc tctgggtcac   780
gaagctatcc tggctgacat caccccggct gaactgtacg acgctgacga agttctgggt   840
tgctcaaccg gtggtggtgt ttggccgttc gtttctgttg acggtaactc tatctctgac   900
ggtgttccgg gtccggttac ccagtctatc atccgtcgtt actgggaact gaacgttgaa   960
ccttcttctc tgctgacccc ggtacagtac                                     990

<210> SEQ ID NO 18
<211> LENGTH: 330
```

<212> TYPE: PRT
<213> ORGANISM: Artificial Sequence
<220> FEATURE:
<223> OTHER INFORMATION: Engineered variant of Arthrobacter transaminase

<400> SEQUENCE: 18

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ile Val Ser Ile Thr
        115                 120                 125

Arg Gly Tyr Ser Ser Thr Pro Trp Glu Arg Asp Ile Thr Lys His Arg
130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 19
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 19

```
atggctttct cagctgacac ccctgaaatc gtttacaccc acgacaccgg tctggactat    60
atcacctact ctgactacga actggacccg gctaacccgc tggctggtgg tgctgcttgg   120
atcgaaggtg ctttcgttcc gccgtctgaa gctcgtatct ctatcttcga ccagggtttt   180
tatacttctg acgctaccta caccgtcttc acgtttgga acggtaacgc tttccgtctg   240
ggggaccaca tcgaacgtct gttctctaat gcggaatcta ttcgtttgat cccgccgctg   300
acccaggacg aagttaaaga gatcgctctg gaactggttg ctaaaaccga actgcgtgaa   360
gcgatcgttt ctgtttctat cacccgtggt tactcttcta ccccatggga gcgtgacatc   420
accaaacatc gtccgcaggt ttacatgtat gctgttccgt accagtggat cgtaccgttt   480
gaccgcatcc gtgacggtgt tcacctgatg gttgctcagt cagttcgtcg taccgcgt    540
agctctatcg acccgcaggt taaaaacttc cagtggggtg acctgatccg tgcaattcag   600
gaaacccacg accgtggttt cgagctgccg ctgctgctgg actgcgacaa cctgctggct   660
gaaggtccgg gtttcaacgt tgttgttatc aaagacggtg ttgttcgttc ccgggtcgt    720
gctgctctgc cgggtatcac ccgtaaaacc gttctggaaa tcgctgaatc tctgggtcac   780
gaagctatcc tggctgacat caccccggct gaactgtacg acgctgacga agttctgggt   840
tgctcaaccg gtggtggtgt ttggccgttc gtttctgttg acggtaactc tatctctgac   900
ggtgttccag gtccggttac ccagtctatc atccgtcgtt actgggaact gaacgttgaa   960
ccttcttctc tgctgacccc ggtacagtac                                    990
```

<210> SEQ ID NO 20
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 20

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Trp Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
```

```
               180                 185                 190
Gly Asp Leu Ile Arg Ala Ile Gln Glu Thr His Asp Arg Gly Phe Glu
            195                 200                 205

Leu Pro Leu Leu Leu Asp Cys Asp Asn Leu Leu Ala Glu Gly Pro Gly
        210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
        290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 21
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 21
atggctttct cagctgacac ccctgaagtc gtttacaccc gcgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccgtcttc cacgtttgga acgtaacgc tttccgtctg      240 ggggaccaca tcgaacgtct gttctctaat gcggaatcta ttcgtttgat cccgccgctg     300
acccaggacg aagtcaaaga gatcgctctg gaactggttg ctaaaaccga actgcgtgaa     360
gcgatcgttt ctgtttctat caccgtggt tactcttcta ccccatggga gcgtgacatc      420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc agtggggtg acctgatccg tgcaattcag      600
gaaacccacg accgtggttt cgagctgccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccccggct gaactgtacg acgctgacga agttctgggt     840
tgctcaaccg gtggtggtgt tggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                      990

<210> SEQ ID NO 22
<211> LENGTH: 330
<212> TYPE: PRT
<213> ORGANISM: Artificial Sequence
<220> FEATURE:
```

<223> OTHER INFORMATION: Engineered variant of Arthrobacter transaminase

<400> SEQUENCE: 22

```
Met Ala Phe Ser Ala Asp Thr Pro Glu Val Val Tyr Thr Arg Asp Thr
1               5                   10                  15
Gly Leu Asp Tyr Ile Thr Tyr Ser Asp Tyr Glu Leu Asp Pro Ala Asn
                20                  25                  30
Pro Leu Ala Gly Gly Ala Ala Trp Ile Glu Gly Ala Phe Val Pro Pro
            35                  40                  45
Ser Glu Ala Arg Ile Ser Ile Phe Asp Gln Gly Phe Tyr Thr Ser Asp
        50                  55                  60
Ala Thr Tyr Thr Val Phe His Val Trp Asn Gly Asn Ala Phe Arg Leu
65                  70                  75                  80
Gly Asp His Ile Glu Arg Leu Phe Ser Asn Ala Glu Ser Ile Arg Leu
                85                  90                  95
Ile Pro Pro Leu Thr Gln Asp Glu Val Lys Glu Ile Ala Leu Glu Leu
            100                 105                 110
Val Ala Lys Thr Glu Leu Arg Glu Ala Ile Val Ser Val Ser Ile Thr
        115                 120                 125
Arg Gly Tyr Ser Ser Thr Pro Trp Glu Arg Asp Ile Thr Lys His Arg
130                 135                 140
Pro Gln Val Tyr Met Tyr Ala Val Pro Tyr Gln Trp Ile Val Pro Phe
145                 150                 155                 160
Asp Arg Ile Arg Asp Gly Val His Leu Met Val Ala Gln Ser Val Arg
                165                 170                 175
Arg Thr Pro Arg Ser Ser Ile Asp Pro Gln Val Lys Asn Phe Gln Trp
            180                 185                 190
Gly Asp Leu Ile Arg Ala Ile Gln Glu Thr His Asp Arg Gly Phe Glu
        195                 200                 205
Leu Pro Leu Leu Leu Asp Cys Asp Asn Leu Leu Ala Glu Gly Pro Gly
210                 215                 220
Phe Asn Val Val Ile Lys Asp Gly Val Val Arg Ser Pro Gly Arg
225                 230                 235                 240
Ala Ala Leu Pro Gly Ile Thr Arg Lys Thr Val Leu Glu Ile Ala Glu
                245                 250                 255
Ser Leu Gly His Glu Ala Ile Leu Ala Asp Ile Thr Pro Ala Glu Leu
            260                 265                 270
Tyr Asp Ala Asp Glu Val Leu Gly Cys Ser Thr Gly Gly Gly Val Trp
        275                 280                 285
Pro Phe Val Ser Val Asp Gly Asn Ser Ile Ser Asp Gly Val Pro Gly
        290                 295                 300
Pro Val Thr Gln Ser Ile Ile Arg Arg Tyr Trp Glu Leu Asn Val Glu
305                 310                 315                 320
Pro Ser Ser Leu Leu Thr Pro Val Gln Tyr
                325                 330
```

<210> SEQ ID NO 23
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 23
atggctttct cagctgacac ccctgaaatc gtttacaccc acgacaccgg tctggactat    60

```
atcacctact ctgactacga actggacccg gctaacccgc tggctggtgg tgctgcttgg    120
atcgaaggtg ctttcgttcc gccgtctgaa gctcgtatct ctatcttcga ccagggtttt    180
tatacttctg acgctaccta caccaccttc acgtttgga acggtaacgc tttccgtctg    240
ggggaccaca tcgaacgtct gttctctaat gcggaatcta ttcgtttgat cccgccgctg    300
acccaggacg aagttaaaga gatcgctctg gaactggttg ctaaaaccga actgcgtgaa    360
gcgatcgtta tcgtttctat cacccgtggt tactcttcta ccccatggga gcgtgacatc    420
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
ggctctatcg acccgcaggt taaaaacttc cagtggggtg acctgatccg tgcaattcag    600
gaaacccacg accgtggttt cgagctgccg ctgctgctgg actgcgacaa cctgctggct    660
gaaggtccgg gtttcaacgt tgttgttatc aaagacggtg ttgttcgttc tccgggtcgt    720
gctgctctgc ggggtatcac ccgtaaaaac gttctggaaa tcgctgaatc tctgggtcac    780
gaagctatcc tggctgacat caccccggct gaactgtacg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgaccc ggtacagtac                                       990
```

<210> SEQ ID NO 24
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 24

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ile Val Ser Ile Thr
        115                 120                 125

Arg Gly Tyr Ser Ser Thr Pro Trp Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Gly Ser Ile Asp Pro Gln Val Lys Asn Phe Gln Trp
            180                 185                 190

Gly Asp Leu Ile Arg Ala Ile Gln Glu Thr His Asp Arg Gly Phe Glu

```
            195                 200                 205
Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 25
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 25

```
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg cttcgttcc gccgtctgaa gctcgtatct ctatcttcga ccagggtttt     180
tatacttctg acgctaccta caccgtcttc cacgtttgga acggtaacgc tttccgtctg     240
ggggaccaca tcgaacgtct gttctctaat gcggaatcta ttcgtttgat cccgccgctg     300
acccaggacg aagttaaaga tcgctctg gaactggttg ctaaaaccga actgcgtgaa     360
gcgatcgttt ctgtttctat caccgtgg tactcttcta ccccatggga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagctgccg ctgctgctgg actgcgacaa cctgctggct     660
gaaggtccgg gtttcaacgt tgttgttatc aaagacggtg ttgttcgttc tccgggtcgt     720
gctgctctgc cgggcatcac ccgtaaaacc gttctggaaa tcgctgaatc tctgggtcac     780
gaagctatcc tgactgacat caccccggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                      990
```

<210> SEQ ID NO 26
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 26

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
                20                  25                  30

Pro Leu Ala Gly Gly Ala Ala Trp Ile Glu Gly Ala Phe Val Pro Pro
            35                  40                  45

Ser Glu Ala Arg Ile Ser Ile Phe Asp Gln Gly Phe Tyr Thr Ser Asp
50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Trp Glu Arg Asp Ile Thr Lys His Arg
130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
210                 215                 220

Phe Asn Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Thr Asp Ile Thr Pro Ala Glu Leu
            260                 265                 270

Tyr Asp Ala Asp Glu Val Leu Gly Cys Ser Thr Gly Gly Gly Val Trp
275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 27
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 27
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc cgccgtctga agctcgtatct ctatcttcga ccagggtttt    180

-continued

```
tatacttctg acgctaccta caccaccttc cacgtttgga acggtaacgc tttccgtctg    240
ggggaccaca tcgaacgtct gttctctaat gcggaatcta ttcgtttgat cccgccgctg    300
acccaggacg aagttaaaga gatcgctctg aactggttg ctaaaaccga actgcgtgaa     360
gcgatcgtta tcgtttctat cacccgtggt tactcttcta ccccatggga gcgtgacatc    420
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagctgccg ctgctgctgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                     990
```

<210> SEQ ID NO 28
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 28

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
                20                  25                  30

Pro Leu Ala Gly Gly Ala Ala Trp Ile Glu Gly Ala Phe Val Pro
            35                  40                  45

Ser Glu Ala Arg Ile Ser Ile Phe Asp Gln Gly Phe Tyr Thr Ser Asp
    50                  55                  60

Ala Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ile Ser Ile Thr
        115                 120                 125

Arg Gly Tyr Ser Ser Thr Pro Trp Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
```

```
                    210                 215                 220

Phe Asn Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 29
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 29
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccgtcttc cacgtttgga acgtaacgc tttccgtctg      240 ggggaccaca tcgaacgtct gttctctaat gcggaatcta ttcgtttgat cccgctgctg     300
acccaggacg aagttaaaga gatcgctctg gaactggttg ctaaaaccga actgcgtgaa     360
gcgatcgttt ctgtttctat caccgtggt tactcttcta ccccatggga gcgtgacatc      420
accagacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagctgccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccccggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                      990

<210> SEQ ID NO 30
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 30

Met Ala Phe Ser Ala Asp Thr Pro Glu Ile Val Tyr Thr His Asp Thr
1               5                   10                  15
```

```
Gly Leu Asp Tyr Ile Thr Tyr Ser Asp Tyr Glu Leu Asp Pro Ala Asn
                20                  25                  30

Pro Leu Ala Gly Gly Ala Ala Trp Ile Glu Gly Ala Phe Val Pro Pro
            35                  40                  45

Ser Glu Ala Arg Ile Ser Ile Phe Asp Gln Gly Phe Tyr Thr Ser Asp
        50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Leu Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Trp Glu Arg Asp Ile Thr Arg His Arg
130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 31
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 31
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccgtcttc cacgtttgga acggtaacgc tttccgtctg     240
```

```
ggggaccaca tcgaacgtct gttctctaat gcggaatcta ttcgtttgat cccgccgctg    300
acccaggacg aagttaaaga gatcgctctg gaactggttg ctaaaaccga actgcgtgaa    360
gcgatcgtta tcgtttctat cacccgtggt tactcttcta ccccattcga gcgtgacatc    420
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagctgccg ctgctgctgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat cacccccggct gaactgtacg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                     990
```

<210> SEQ ID NO 32
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 32

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ile Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
```

```
                225                 230                 235                 240
Ala Ala Leu Pro Gly Ile Thr Arg Lys Thr Val Leu Glu Ile Ala Glu
                    245                 250                 255

Ser Leu Gly His Glu Ala Ile Leu Ala Asp Ile Thr Pro Ala Glu Leu
                260                 265                 270

Tyr Asp Ala Asp Glu Val Leu Gly Cys Ser Thr Gly Gly Val Trp
                275                 280                 285

Pro Phe Val Ser Val Asp Gly Asn Ser Ile Ser Asp Gly Val Pro Gly
                290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 33
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 33
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccaccttc acgtttgga acggtaacgc tttccgtctg      240
ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
gcgatcgttg tcgtttctat caccccgtggt tactcttcta ccccatggga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagctgccg ctgctgctgg actgcgacaa cctgctggct     660
gaaggtccgg gttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccccggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                      990

<210> SEQ ID NO 34
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 34

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
                20                  25                  30
```

```
Pro Leu Ala Gly Gly Ala Ala Trp Ile Glu Gly Ala Phe Val Pro Pro
            35                  40                  45

Ser Glu Ala Arg Ile Ser Ile Phe Asp Gln Gly Phe Tyr Thr Ser Asp
 50                  55                  60

Ala Thr Tyr Thr Thr Phe His Val Trp Asn Gly Asn Ala Phe Arg Leu
 65                  70                  75                  80

Gly Asp His Ile Glu Arg Leu Phe Ser Asn Ala Glu Ser Ile Arg Leu
                 85                  90                  95

Ile Pro Pro Leu Thr Gln Asp Glu Val Lys Glu Ile Ala Leu Glu Leu
                100                 105                 110

Val Ala Lys Thr Glu Leu Arg Glu Ala Ile Val Val Ser Ile Thr
                115                 120                 125

Arg Gly Tyr Ser Ser Thr Pro Trp Glu Arg Asp Ile Thr Lys His Arg
                130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
                180                 185                 190

Gly Asp Leu Ile Arg Ala Ile Gln Glu Thr His Asp Arg Gly Phe Glu
                195                 200                 205

Leu Pro Leu Leu Leu Asp Cys Asp Asn Leu Leu Ala Glu Gly Pro Gly
                210                 215                 220

Phe Asn Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
                260                 265                 270

Tyr Asp Ala Asp Glu Val Leu Gly Cys Ser Thr Gly Gly Gly Val Trp
                275                 280                 285

Pro Phe Val Ser Val Asp Gly Asn Ser Ile Ser Asp Gly Val Pro Gly
                290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 35
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 35
atggctttct cagctgacac ccctgaaatc gtttacaccc acgacaccgg tctggactat      60
atcacctact ctgactacga actgacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccgtcttc cacgtttgga acggtaacgc tttccgtctg     240
ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
```

```
gcgatcgttt ctgtttctat cacccgtggt tactcttcta ccccatggga gcgtgacatc    420
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagttatcg ctgctgctgg actgcgacaa cctgctggct    660
gaaggtccgg gtttcaacgt tgttgttatc aaagacggtg ttgttcgttc ccgggtcgt    720 gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                     990
```

<210> SEQ ID NO 36
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 36

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Trp Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Ser Leu Leu Leu Asp Cys Asp Asn Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
```

Ser Leu Gly His Glu Ala Ile Leu Ala Asp Ile Thr Pro Ala Glu Leu
                260                 265                 270

Tyr Asp Ala Asp Glu Val Leu Gly Cys Ser Thr Gly Gly Gly Val Trp
            275                 280                 285

Pro Phe Val Ser Val Asp Gly Asn Ser Ile Ser Asp Gly Val Pro Gly
        290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 37
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 37
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg cttttcgttcc gccgtctgaa gctcgtatct ctatcttcga ccagggtttt     180
tatacttctg acgctaccta caccaccttc acgtttgga acggtaacgc tttccgtctg     240
ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
gcgatcgttt ctgttttctat cacccgtggt tactcttcta ccccatggga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg aactgatccg tgcaattcag     600
gaaacccacg accgtggttt cgaggaatcg ctgctgctgg actgcgacaa cctgctggct     660
gaaggtccgg gtttcaacgt tgttgttatc aaagacggtg ttgttcgttc ccgggtcgt      720
gctgctctgc cgggtatcac ccgtaaaacc gttctggaaa tcgctgaatc tctgggtcac     780
gaagctatcc tggctgacat cacccccggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                      990

<210> SEQ ID NO 38
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 38

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
        50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
            115                 120                 125

Arg Gly Tyr Ser Ser Thr Pro Trp Glu Arg Asp Ile Thr Lys His Arg
        130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Glu Ser Leu Leu Leu Asp Cys Asp Asn Leu Leu Ala Glu Gly Pro Gly
210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 39
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 39
atggctttct cagctgacac ccctgaaatc gtttacaccc acgacaccgg tctggactat    60
atcacctact ctgactacga actggacccg gctaacccgc tggctggtgg tgctgcttgg   120
atcgaaggtg ctttcgttcc gccgtctgaa gctcgtatct ctatcttcga ccagggtttt   180
tatacttctg acgctaccta caccaccttc cacgtttgga acggtaacgc tttccgtctg   240
ggggaccaca tcgaacgtct gttctctaat gcggaatcta ttcgtttgat cccgccgctg   300
acccaggacg aagttaaaga gatcgctctg gaactggttg ctaaaaccga actgcgtgaa   360
gcgatcgttg tggtttctat cacccgtggt tactcttcta ccccattcga gcgtgacatc   420

```
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagctgtcg ctgctgctgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg tggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                    990
```

<210> SEQ ID NO 40
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 40

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Ser Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
```

```
              260                 265                 270
Tyr Asp Ala Asp Glu Val Leu Gly Cys Ser Thr Gly Gly Val Trp
            275                 280                 285

Pro Phe Val Ser Val Asp Gly Asn Ser Ile Ser Asp Gly Val Pro Gly
            290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 41
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 41
atggctttct cagctgacac ccctgaaatc gtttacaccc acgacaccgg tctggactat      60
atcacctact ctgactacga actggacccg ctaacccgc tggctggtgg tgctgcttgg     120
atcgaaggtg ctttcgttcc gccgtctgaa gctcgtatct ctatcttcga ccagggtttt    180
tatacttctg acgctaccta caccgttttc cacgtttgga cggtaacgc tttccgtctg     240 ggggaccaca tcgaacgtct gttctctaat gcggaatcta ttcgtttgat cccgccgctg    300
acccaggacg aagttaaaga gatcgctctg gaactggttg ctaaaaccga actgcgtgaa    360
gcgatcgttt ctgtttctat cacccgtggt tactcttcta ccccattcga gcgtgacatc    420
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagctgccg ctgctgctgg actgcgacaa cctgctggct    660
gaaggtccgg gtttcaacgt tgttgttatc aaagacggtg ttgttcgttc ccgggtcgt    720 gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                     990

<210> SEQ ID NO 42
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 42

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60
```

```
Ala Thr Tyr Thr Val Phe His Val Trp Asn Gly Asn Ala Phe Arg Leu
 65                  70                  75                  80

Gly Asp His Ile Glu Arg Leu Phe Ser Asn Ala Glu Ser Ile Arg Leu
                 85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
210                 215                 220

Phe Asn Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 43
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 43

```
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt    180
tatacttctg acgctaccta caccgttttc cacgtttgga acggtaacgc tttccgtctg    240
ggggaccaca tcgaacgtct gttctctaat gcggaatcta tccgttttgat cccgccgctg    300 acccaggacg aagttaaaga gatcgctctg gaactggttg ctaaaaccga actgcgtgaa    360
gcgatcgttt ctgtttctat cacccgtggt tactcttcta cccccattcga gcgtgacatc    420 accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
```

```
agctctatcg acccgcaggt taaaaacttc cagtggggtg acctgatccg tgcaattcag    600
gaaacccacg accgtggttt cgagctgccg ctgctgctgg actacgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                     990
```

<210> SEQ ID NO 44
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 44

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Tyr Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
```

```
                275                 280                 285
Pro Phe Val Ser Val Asp Gly Asn Ser Ile Ser Asp Gly Val Pro Gly
            290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 45
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 45
atggctttct cagctgacac ccctgaaatc gtttacaccc acgacaccgg tctggactat      60
atcacctact ctgactacga actgaccccg gctaacccgc tggctggtgg tgctgcttgg     120
atcgaaggtg ctttcgttcc gccgtctgaa gctcgtatct ctatcttcga ccagggtttt     180
tatacttctg acgctaccta caccaccttc acgtttgga acggtaacgc tttccgtctg     240
ggggaccaca tcgaacgtct gttctctaat gcggaatcta ttcgttttga cccgccgctg     300
acccaggacg aagttaaaga gatcgctctg aactggttg ctaaaaccga actgcgtgaa     360
gcgatcgttt ctgtttctat caccgtggt tactcttcta ccccattcga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgaggagccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccccggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                      990

<210> SEQ ID NO 46
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 46

Met Ala Phe Ser Ala Asp Thr Pro Glu Ile Val Tyr Thr His Asp Thr
1               5                  10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80
```

```
Gly Asp His Ile Glu Arg Leu Phe Ser Asn Ala Glu Ser Ile Arg Leu
                85                  90                  95
Ile Pro Pro Leu Thr Gln Asp Glu Val Lys Glu Ile Ala Leu Glu Leu
            100                 105                 110
Val Ala Lys Thr Glu Leu Arg Glu Ala Ile Val Ser Val Ser Ile Thr
        115                 120                 125
Arg Gly Tyr Ser Ser Thr Pro Phe Glu Arg Asp Ile Thr Lys His Arg
    130                 135                 140
Pro Gln Val Tyr Met Tyr Ala Val Pro Tyr Gln Trp Ile Val Pro Phe
145                 150                 155                 160
Asp Arg Ile Arg Asp Gly Val His Leu Met Val Ala Gln Ser Val Arg
                165                 170                 175
Arg Thr Pro Arg Ser Ser Ile Asp Pro Gln Val Lys Asn Phe Gln Trp
            180                 185                 190
Gly Asp Leu Ile Arg Ala Ile Gln Glu Thr His Asp Arg Gly Phe Glu
        195                 200                 205
Glu Pro Leu Leu Leu Asp Cys Asp Asn Leu Leu Ala Glu Gly Pro Gly
    210                 215                 220
Phe Asn Val Val Val Ile Lys Asp Gly Val Val Arg Ser Pro Gly Arg
225                 230                 235                 240
Ala Ala Leu Pro Gly Ile Thr Arg Lys Thr Val Leu Glu Ile Ala Glu
                245                 250                 255
Ser Leu Gly His Glu Ala Ile Leu Ala Asp Ile Thr Pro Ala Glu Leu
            260                 265                 270
Tyr Asp Ala Asp Glu Val Leu Gly Cys Ser Thr Gly Gly Gly Val Trp
        275                 280                 285
Pro Phe Val Ser Val Asp Gly Asn Ser Ile Ser Asp Gly Val Pro Gly
    290                 295                 300
Pro Val Thr Gln Ser Ile Ile Arg Arg Tyr Trp Glu Leu Asn Val Glu
305                 310                 315                 320
Pro Ser Ser Leu Leu Thr Pro Val Gln Tyr
                325                 330

<210> SEQ ID NO 47
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 47
atggctttct cagctgacac ccctgaaatc gtttacaccc acgacaccgg tctggactat      60
atcacctact ctgactacga actgaccccg gctaacccgc tggctggtgg tgctgcttgg     120
atcgaaggtg ctttcgttcc gccgtctgaa gctcgtatct ctatcttcga ccagggtttt     180
tatacttctg acgctaccta caccgttttc acgtttggaa cggtaacgc tttccgtctg      240 ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
gcgatcgttt ctgtttctat cacccgtggt tactcttcta ccccattcga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
```

```
gaaacccacg accgtggttt cgagctgccg ctgctgctgg actgcgacag cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                    990
```

<210> SEQ ID NO 48
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 48

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Ser Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
```

```
                    290                 295                 300
Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 49
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 49
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ttttcgttcc gccgtctgaa gctcgtatct ctatcttcga ccagggtttt     180
tatacttctg acgctaccta caccaccttc acgtttgga acggtaacgc tttccgtctg      240
ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
gcgatcgttt ctgtttctat cacccgtggt tactcttcta ccccattcga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagctgccg ctgctgctgg actgcgacaa cctgctggct     660
gaaggtaatg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccccggct gaactgtacg acgctgacga agttctgggt     840
tgctcaaccg gtggtggtgt tggccgttc gtttctgttg acggtaactc tatctctgac     900
ggtgttccgg tccggttac ccagtctatc atccgtcgtt actgggaact gaacgttgaa     960
ccttcttctc tgctgacccc ggtacagtac                                      990

<210> SEQ ID NO 50
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 50

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
                20                  25                  30

Pro Leu Ala Gly Gly Ala Ala Trp Ile Glu Gly Val Phe Val Pro Pro
            35                  40                  45

Ser Glu Ala Arg Ile Ser Ile Phe Asp Gln Gly Phe Tyr Thr Ser Asp
        50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95
```

```
Ile Pro Pro Leu Thr Gln Asp Glu Val Lys Glu Ile Ala Leu Glu Leu
            100                 105                 110
Val Ala Lys Thr Glu Leu Arg Glu Ala Ile Val Ser Val Ser Ile Thr
        115                 120                 125
Arg Gly Tyr Ser Ser Thr Pro Phe Glu Arg Asp Ile Thr Lys His Arg
    130                 135                 140
Pro Gln Val Tyr Met Tyr Ala Val Pro Tyr Gln Trp Ile Val Pro Phe
145                 150                 155                 160
Asp Arg Ile Arg Asp Gly Val His Leu Met Val Ala Gln Ser Val Arg
                165                 170                 175
Arg Thr Pro Arg Ser Ser Ile Asp Pro Gln Val Lys Asn Phe Gln Trp
            180                 185                 190
Gly Asp Leu Ile Arg Ala Ile Gln Glu Thr His Asp Arg Gly Phe Glu
        195                 200                 205
Leu Pro Leu Leu Leu Asp Cys Asp Asn Leu Leu Ala Glu Gly Asn Gly
    210                 215                 220
Phe Asn Val Val Ile Lys Asp Gly Val Val Arg Ser Pro Gly Arg
225                 230                 235                 240
Ala Ala Leu Pro Gly Ile Thr Arg Lys Thr Val Leu Glu Ile Ala Glu
                245                 250                 255
Ser Leu Gly His Glu Ala Ile Leu Ala Asp Ile Thr Pro Ala Glu Leu
            260                 265                 270
Tyr Asp Ala Asp Glu Val Leu Gly Cys Ser Thr Gly Gly Gly Val Trp
        275                 280                 285
Pro Phe Val Ser Val Asp Gly Asn Ser Ile Ser Asp Gly Val Pro Gly
    290                 295                 300
Pro Val Thr Gln Ser Ile Ile Arg Arg Tyr Trp Glu Leu Asn Val Glu
305                 310                 315                 320
Pro Ser Ser Leu Leu Thr Pro Val Gln Tyr
                325                 330

<210> SEQ ID NO 51
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 51
atggctttct cagctgacac ccctgaaatc gtttacaccc acgacaccgg tctggactat    60
atcacctact ctgactacga actggacccg gctaacccgc tggctggtgg tgctgcttgg   120
atcgaaggtg ctttcgttcc gccgtctgaa gctcgtatct ctatcttcga ccagggtttt   180
tatacttctg acgctaccta caccaccttc acgtttgga acggtaacgc tttccgtctg   240
ggggaccaca tcgaacgtct gttctctaat gcggaatcta ttcgtttgat cccgccgctg   300
acccaggacg aagttaaaga gatcgctctg gaactggttg ctaaaaccga actgcgtgaa   360
gcgatcgttt ctgtttctat cacccgtggt tactcttcta ccccattcga gcgtgacatc   420
accaaacatc gtccgcaggt ttacatgtat gctgttccgt accagtggat cgtaccgttt   480
gaccgcatcc gtgacggtgt tcacctgatg gttgctcagt cagttcgtcg tacaccgcgt   540
agctctatcg acccgcaggt taaaaacttc cagtggggtg acctgatccg tgcaattcag   600
gaaacccacg accgtggttt cgagctgccg ctgctgctgg actgcgacaa cctgctggct   660
gaaggtaatg gtttcaacgt tgttgttatc aaagacggtg ttgttcgttc tccgggtcgt   720
```

```
gctgctctgc cgggtatcac ccgtaaaacc gttctggaaa tcgctgaatc tctgggtcac    780
gaagctatcc tggctgacat cacccccggct gaactgtacg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                      990
```

```
<210> SEQ ID NO 52
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 52
```

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Asn Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu

```
                305                 310                 315                 320
Pro Ser Ser Leu Leu Thr Pro Val Gln Tyr
                    325                 330

<210> SEQ ID NO 53
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 53
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccaccttc acgtttgga acggtaacgc tttccgtctg      240
ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
gcgatcgttt ctgtttctat cacccgtggt tactcttcta ccccattcga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc agtggggtg acctgatccg tgcaattcag      600
gaaacccacg accgtggttt cgagctgccg ctgctgctgg actgcgacaa cctgctggct     660
gaaggtctgg gtttcaacgt tgttgttatc aaagacggtg ttgttcgttc tccgggtcgt     720
gctgctctgc cgggtatcac ccgtaaaaacc gttctggaaa tcgctgaatc tctgggtcac     780
gaagctatcc tggctgacat caccccggct gaactgtacg acgctgacga agttctgggt     840
tgctcaaccg tggtggtgt ttggccgttc gtttctgttg acggtaactc tatctctgac      900
ggtgttccgg gtccggttac ccagtctatc atccgtcgtt actgggaact gaacgttgaa     960
ccttcttctc tgctgacccc ggtacagtac                                      990

<210> SEQ ID NO 54
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 54

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
                20                  25                  30

Pro Leu Ala Gly Gly Ala Ala Trp Ile Glu Gly Ala Phe Val Pro Pro
            35                  40                  45

Ser Glu Ala Arg Ile Ser Ile Phe Asp Gln Gly Phe Tyr Thr Ser Asp
        50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110
```

Val Ala Lys Thr Glu Leu Arg Glu Ala Ile Val Ser Val Ser Ile Thr
            115                 120                 125

Arg Gly Tyr Ser Ser Thr Pro Phe Glu Arg Asp Ile Thr Lys His Arg
        130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Leu Gly
210                 215                 220

Phe Asn Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 55
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 55
atggctttct cagctgacac ccctgaaatc gtttacaccc cgacaccgg tctggactat      60 atcacctact ctgactacga actggacccg gctaacccgc tggctggtgg tgctgcttgg    120
atcgaaggtg ctttcgttcc gccgtctgaa gctcgtatct ctatcctcga ccagggtttt    180
tatacttctg acgctaccta caccaccttc acgtttgga acggtaacgc tttccgtctg    240
ggggaccaca tcgaacgtct gttctctaat gcggaatcta ttcgtttgat cccgccgctg    300
acccaggacg aagttaaaga gatcgctctg gaactggttg ctaaaaccga actgcgtgaa    360
gcgatcgtta ttgtttctat cacccgtggt tactcttcta ccccattcga gcgtgacatc    420
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagctgccg ctgctgctgg actgcgacaa cctgctggct    660
gaaggtccgg tttcaacgt tgttgttatc aaagacggtg ttgttcgttc tccgggtcgt    720
gctgctctgc cgggtatcac ccgtaaaacc gttctggaaa tcgctgaatc tctgggtcac    780

```
gaagctatcc tggctgacat cacccccggct gaactgtacg acgctgacga agttctgggt    840
tgctcaaccg gtggtggtgt ttggccgttc gttctgttg acggtaactc tatctctgac      900
ggtgttccgg gtccggttac ccagtctatc atccgtcgtt actgggaact gaacgttgaa     960
ccttcttctc tgctgacccc ggtacagtac                                      990
```

<210> SEQ ID NO 56
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 56

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Leu Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ile Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
```

<210> SEQ ID NO 57
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 57

```
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg cttttcgttcc gccgtctgaa gctcgtatct ctatcttcga ccagggtttt    180
tatacttctg acgctaccta caccaccttc cacgtttgga acggtaacgc tttccgtctg    240
ggggaccaca tcgaacgtct gttctctaat gcggaatcta ttcgttttga cccgccgctg    300
acccaggacg aagttaaaga gatcgctctg gaactggttg ctaaaaccga actgcgtgaa    360
gcgatcgttt ctgtttctat cacccgtggt tactcttcta ccccattcga gcgtgacatc    420
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagctgccg ctgctgctgg actgcgacaa cctgctggct    660
gaaggtattg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg gtggtggtgt ttggccgttc gtttctgttg acggtaactc tatctctgac    900
ggtgttccgg tccggttac ccagtctatc atccgtcgtt actgggaact gaacgttgaa    960
ccttcttctc tgctgacccc ggtacagtac                                      990
```

<210> SEQ ID NO 58
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 58

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
                20                  25                  30

Pro Leu Ala Gly Gly Ala Ala Trp Ile Glu Gly Ala Phe Val Pro Pro
            35                  40                  45

Ser Glu Ala Arg Ile Ser Ile Phe Asp Gln Gly Phe Tyr Thr Ser Asp
        50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125
```

Arg Gly Tyr Ser Ser Thr Pro Phe Glu Arg Asp Ile Thr Lys His Arg
            130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Ile Gly
210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
            325                 330

<210> SEQ ID NO 59
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 59
atggctttct cagctgacgc ccctgaaatc gtttacaccc acgacaccgg tctggactat     60
atcacctact ctgactacga actgacccg gctaacccgc tggctggtgg tgctgcttgg    120
atcgaaggtg ctttcgttcc gccgtctgaa gctcgtatct ctatcttcga ccagggtttt    180
tatacttctg acgctaccta caccaccttc acgtttgga acggtaacgc tttccgtctg    240
ggggaccaca tcgaacgtct gttctctaat gcggaatcta ttcgttttgat cccgccgctg    300 acccaggacg aagttaaaga gatcgctctg gaactggttg ctaaaaccga actgcgtgaa    360
gcgatcgttc ttgtttctat caccgtggt tactcttcta ccccattcga gcgtgacatc    420
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagctgccg ctgctgctgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat cacccccggct gaactgtacg acgctgacga agttctgggt    840
tgctcaaccg gtggtggtgt ttggccgttc gttctgttg acggtaactc tatctctgac    900

```
ggtgttccgg gtccggttac ccagtctatc atccgtcgtt actgggaact gaacgttgaa    960
ccttcttctc tgctgacccc ggtacagtac                                     990
```

<210> SEQ ID NO 60
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 60

```
Met Ala Phe Ser Ala Asp Ala Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Leu Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 61
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 61

```
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccaccttc acgtttgga acggtaacgc tttccgtctg     240
ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
gcgatcgttt ctgtttctat cacccgtggt tactcttcta ccccattcga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcatatcag     600
gaaacccacg accgtggttt cgagctgccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccccggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                      990
```

<210> SEQ ID NO 62
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 62

```
Met Ala Phe Ser Ala Asp Thr Pro Glu Ile Val Tyr Thr His Asp Thr
 1               5                  10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140
```

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
            165                 170                 175

Arg Thr Pro Arg Ser Ser Ile Asp Pro Gln Val Lys Asn Phe Gln Trp
        180                 185                 190

Gly Asp Leu Ile Arg Ala Tyr Gln Glu Thr His Asp Arg Gly Phe Glu
    195                 200                 205

Leu Pro Leu Leu Leu Asp Cys Asp Asn Leu Leu Ala Glu Gly Pro Gly
210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
            245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
            325                 330

<210> SEQ ID NO 63
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 63
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta cacctggttc acgtttggaa cggtaacgc tttccgtctg     240 ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
gcgatcgttt ctgtttctat cacccgtggt tactcttcta ccccattcga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg taccgcgt      540 agctctatcg acccgcaggt taaaaacttc cagtggggtg acctgatccg tgcaattcag     600
gaaacccacg accgtggttt cgagctgccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccccggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
cctccttctc tgctgacccc ggtacagtac 990

<210> SEQ ID NO 64
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 64

Met Ala Phe Ser Ala Asp Thr Pro Glu Ile Val Tyr Thr His Asp Thr
1               5                   10                  15
Gly Leu Asp Tyr Ile Thr Tyr Ser Asp Tyr Glu Leu Asp Pro Ala Asn
            20                  25                  30
Pro Leu Ala Gly Gly Ala Ala Trp Ile Glu Gly Ala Phe Val Pro Pro
        35                  40                  45
Ser Glu Ala Arg Ile Ser Ile Phe Asp Gln Gly Phe Tyr Thr Ser Asp
    50                  55                  60
Ala Thr Tyr Thr Trp Phe His Val Trp Asn Gly Asn Ala Phe Arg Leu
65                  70                  75                  80
Gly Asp His Ile Glu Arg Leu Phe Ser Asn Ala Glu Ser Ile Arg Leu
                85                  90                  95
Ile Pro Pro Leu Thr Gln Asp Glu Val Lys Glu Ile Ala Leu Glu Leu
            100                 105                 110
Val Ala Lys Thr Glu Leu Arg Glu Ala Ile Val Ser Val Ser Ile Thr
        115                 120                 125
Arg Gly Tyr Ser Ser Thr Pro Phe Glu Arg Asp Ile Thr Lys His Arg
    130                 135                 140
Pro Gln Val Tyr Met Tyr Ala Val Pro Tyr Gln Trp Ile Val Pro Phe
145                 150                 155                 160
Asp Arg Ile Arg Asp Gly Val His Leu Met Val Ala Gln Ser Val Arg
                165                 170                 175
Arg Thr Pro Arg Ser Ser Ile Asp Pro Gln Val Lys Asn Phe Gln Trp
            180                 185                 190
Gly Asp Leu Ile Arg Ala Ile Gln Glu Thr His Asp Arg Gly Phe Glu
        195                 200                 205
Leu Pro Leu Leu Leu Asp Cys Asp Asn Leu Leu Ala Glu Gly Pro Gly
    210                 215                 220
Phe Asn Val Val Val Ile Lys Asp Gly Val Val Arg Ser Pro Gly Arg
225                 230                 235                 240
Ala Ala Leu Pro Gly Ile Thr Arg Lys Thr Val Leu Glu Ile Ala Glu
                245                 250                 255
Ser Leu Gly His Glu Ala Ile Leu Ala Asp Ile Thr Pro Ala Glu Leu
            260                 265                 270
Tyr Asp Ala Asp Glu Val Leu Gly Cys Ser Thr Gly Gly Gly Val Trp
        275                 280                 285
Pro Phe Val Ser Val Asp Gly Asn Ser Ile Ser Asp Gly Val Pro Gly
    290                 295                 300
Pro Val Thr Gln Ser Ile Ile Arg Arg Tyr Trp Glu Leu Asn Val Glu
305                 310                 315                 320
Pro Ser Ser Leu Leu Thr Pro Val Gln Tyr
                325                 330

<210> SEQ ID NO 65
<211> LENGTH: 990
<212> TYPE: DNA

<213> ORGANISM: Artificial Sequence
<220> FEATURE:
<223> OTHER INFORMATION: Engineered variant of Arthrobacter transaminase

<400> SEQUENCE: 65

```
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccaccttc acgtttggga acggtaacgc tttccgtctg     240
ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
gcgatcgttt ctgtttctat cacccgtggt tactcttcta ccccatggga gcgtgacatc     420
accaaacatc gtccgcaggt ttacatgtat gctgttccgt accagtggat cgtaccgttt     480
gaccgcatcc gtgacggtgt tcacctgatg gctgctcagt cagttcgtcg tacaccgcgt     540
agctctatcg acccgcaggt taaaaacttc agtggggtg acctgatccg tgcaattcag     600
gaaacccacg accgtggttt cgagctgccg ctgctgctgg actgcgacaa cctgctggct     660
gaaggtccgg gttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccccggct gaactgtacg acgctgacga gttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                      990
```

<210> SEQ ID NO 66
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 66

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Trp Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160
```

Asp Arg Ile Arg Asp Gly Val His Leu Met Ala Ala Gln Ser Val Arg
            165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
            195                 200                 205

Leu Pro Leu Leu Leu Asp Cys Asp Asn Leu Leu Ala Glu Gly Pro Gly
            210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
            245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
            275                 280                 285

Pro Phe Val Ser Val Asp Gly Asn Ser Ile Ser Asp Gly Val Pro Gly
            290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
            325                 330

<210> SEQ ID NO 67
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 67

```
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccaccttc cacgtttgga cggtaacgc tttccgtctg      240
ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
gcgatcgttt tgtttctat cacccgtggt tactcttcta ccccattcga gcgtgacatc      420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagctgccg ctgctgctgg actgcgacaa cctgctggct     660
gaaggtccgg gtttcaacgt tgttgttatc aaagacggtg ttgttcgttc tccgggtcgt     720
gctgctctgc cgagtatcac ccgtaaaacc gttctggaaa tcgctgaatc tctgggtcac     780
gaagctatcc tggctgacat cacccccggct gaactgtacg acgctgacga agttctgggt     840
tgctcaaccg gtggtggtgt tggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                      990
```

```
<210> SEQ ID NO 68
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 68

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Phe Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Ser Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 69
<211> LENGTH: 990
<212> TYPE: DNA
<213> ORGANISM: Artificial Sequence
<220> FEATURE:
<223> OTHER INFORMATION: Engineered variant of Arthrobacter transaminase
```

<400> SEQUENCE: 69

```
atggctttct cagctgacac ccctgaaatc gtttacaccc acgacaccgg tctggactat    60
atcacctact ctgactacga actggacccg gctaacccgc tggctggtgg tgctgcttgg   120
atcgaaggtg ctttcgttcc gccgtctgaa gctcgtatct ctatcttcga ccagggtttt   180
tatacttctg acgctaccta caccaccttc cacgtttgga acggtaacgc tttccgtctg   240
ggggaccaca tcgaacgtct gttctctaat gcggaatcta ttcgtttgat cccgccgctg   300
acccaggacg aagttaaaga gatcgctctg gaactggttg ctaaaaccga actgcgtgaa   360
gcgatcgttt ctgttctat cacccgtggt tactcttcta ccccattcga gcgtgacatc   420
accaaacatc gtccgcaggt ttacatgtat gctgttccgt accagtggat cgtaccgttt   480
gaccgcatcc gtgacggtgt tcacctgatg gttgctcagt cagttcgtcg tacaccgcgt   540
agctctatcg acccgcaggt taaaaacttc agtggggtg acctgatccg tgcaattcag   600
gaaacccacg accgtggttt cgaggatccg ctgctgctgg actgcgacaa cctgctggct   660
gaaggtccgg gtttcaacgt tgttgttatc aaagacggtg ttgttcgttc tccgggtcgt   720
gctgctctgc cgggtatcac ccgtaaaacc gttctggaaa tcgctgaatc tctgggtcac   780
gaagctatcc tggctgacat caccccggct gaactgtacg acgctgacga agttctgggt   840
tgctcaaccg tggtggtgt ttggccgttc gtttctgttg acggtaactc tatctctgac   900
ggtgttccgg gtccggttac ccagtctatc atccgtcgtt actgggaact gaacgttgaa   960
ccttcttctc tgctgacccc ggtacagtac                                    990
```

<210> SEQ ID NO 70
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 70

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175
```

```
Arg Thr Pro Arg Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Asp Pro Leu Leu Leu Asp Cys Asp Asn Leu Leu Ala Glu Gly Pro Gly
210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 71
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 71
atggctttct cagctgacac ccctgaaatc gtttacaccc acgacaccgg tctggactat     60
atcacctact ctgactacga actggacccg gctaacccgc tggctggtgg tgctgcttgg    120
atcgaaggtg cttctgttcc gccgtctgaa gctcgtatct ctatcttcga ccagggtttt    180
tatacttctg acgctaccta caccaccttc acgtttgga acgtaacgc tttccgtctg     240 ggggaccaca tcgaacgtct gttctctaat gcggaatcta ttcgtttgat cccgccgctg    300
acccaggacg aagttaaaga gatcgctctg gaactggttg ctaaaaccga actgcgtgaa    360
gcgatcgttt ttgtttctat cacccgtggt tactcttcta ccccattcga gcgtgacatc    420
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagctgccg ctgctgccgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                    990

<210> SEQ ID NO 72
<211> LENGTH: 330
<212> TYPE: PRT
```

<213> ORGANISM: Artificial Sequence
<220> FEATURE:
<223> OTHER INFORMATION: Engineered variant of Arthrobacter transaminase

<400> SEQUENCE: 72

```
Met Ala Phe Ser Ala Asp Thr Pro Glu Ile Val Tyr Thr His Asp Thr
1               5                  10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Phe Val Ser Ile Thr
        115                 120                 125

Arg Gly Tyr Ser Ser Thr Pro Phe Glu Arg Asp Ile Thr Lys His Arg
130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Pro Asp Cys Asp Asn Leu Leu Ala Glu Gly Pro Gly
210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 73
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 73

```
atggctttct cagctgacac ccctgaaatc gtttacaccc acgacaccgg tctggactat    60
atcacctact ctgactacga actggacccg gctaacccgc tggctggtgg tgctgcttgg   120
atcgaaggtg ctttcgttcc gccgtctgaa gctcgtatct ctatcttcga ccagggtttt   180
tatacttctg acgctaccta caccaccttc cacgtttgga acggtaacgc tttccgtctg   240
ggggaccaca tcgaacgtct gttctctaat gcggaatcta ttcgtttgat cccgccgctg   300
acccaggacg aagttaaaga gatcgctctg gaactggttg ctaaaaccga actgcgtgaa   360
gcgatcgttt ctgtttctat cacccgtggt tactcttcta cccaattcga gcgtgacatc   420
accaaacatc gtccgcaggt ttacatgtat gctgttccgt accagtggat cgtaccgttt   480
gaccgcatcc gtgacggtgt tcacctgatg gttgctcagt cagttcgtcg tacaccgcgt   540
agctctatcg acccgcaggt taaaaacttc cagtggggtg acctgatccg tgcaattcag   600
gaaacccacg accgtggttt cgagctgccg ctgctgctgg actgcgacaa cctgctggct   660
gaaggtccgg gtttcaacgt tgttgttatc aaagacggtg ttgttcgttc ccgggtcgt    720
gctgctctgc cgggtatcac ccgtaaaacc gttctggaaa tcgctgaatc tctgggtcac   780
gaagctatcc tggctgacat caccccggct gaactgtacg acgctgacga agttctgggt   840
tgctcgaccg tggtggtgt ttggccgttc gtttctgttg acggtaactc tatctctgac    900
ggtgttccgg tccggttac ccagtctatc atccgtcgtt actgggaact gaacgttgaa    960
ccttcttctc tgctgacccc ggtacagtac                                    990
```

<210> SEQ ID NO 74
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 74

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Gln Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

```
Gly Asp Leu Ile Arg Ala Ile Gln Glu Thr His Asp Arg Gly Phe Glu
            195                 200                 205

Leu Pro Leu Leu Leu Asp Cys Asp Asn Leu Leu Ala Glu Gly Pro Gly
        210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
            325                 330

<210> SEQ ID NO 75
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 75
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta cacctgtttc acgtttgga acggtaacgc tttccgtctg     240
ggggaccaca tcgaacgtct gttctctaat gcggaatcta ttcgttttga tccgccgctg     300
acccaggacg aagttaaaga gatcgctctg gaactggttg ctaaaaccga actgcgtgaa     360
gcgatcgttt ctgtttctat caccgtggt tactcttcta ccccattcga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagctgccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccccggct gaactgtacg acgctgacga agttctgggt     840
tgctcaaccg gtggtggtgt tggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                       990

<210> SEQ ID NO 76
<211> LENGTH: 330
<212> TYPE: PRT
<213> ORGANISM: Artificial Sequence
<220> FEATURE:
<223> OTHER INFORMATION: Engineered variant of Arthrobacter transaminase
```

<400> SEQUENCE: 76

```
Met Ala Phe Ser Ala Asp Thr Pro Glu Ile Val Tyr Thr His Asp Thr
1               5                   10                  15
Gly Leu Asp Tyr Ile Thr Tyr Ser Asp Tyr Glu Leu Asp Pro Ala Asn
            20                  25                  30
Pro Leu Ala Gly Ala Ala Trp Ile Glu Gly Ala Phe Val Pro Pro
        35                  40                  45
Ser Glu Ala Arg Ile Ser Ile Phe Asp Gln Gly Phe Tyr Thr Ser Asp
    50                  55                  60
Ala Thr Tyr Thr Cys Phe His Val Trp Asn Gly Asn Ala Phe Arg Leu
65                  70                  75                  80
Gly Asp His Ile Glu Arg Leu Phe Ser Asn Ala Glu Ser Ile Arg Leu
                85                  90                  95
Ile Pro Pro Leu Thr Gln Asp Glu Val Lys Glu Ile Ala Leu Glu Leu
            100                 105                 110
Val Ala Lys Thr Glu Leu Arg Glu Ala Ile Val Ser Val Ser Ile Thr
        115                 120                 125
Arg Gly Tyr Ser Ser Thr Pro Phe Glu Arg Asp Ile Thr Lys His Arg
130                 135                 140
Pro Gln Val Tyr Met Tyr Ala Val Pro Tyr Gln Trp Ile Val Pro Phe
145                 150                 155                 160
Asp Arg Ile Arg Asp Gly Val His Leu Met Val Ala Gln Ser Val Arg
                165                 170                 175
Arg Thr Pro Arg Ser Ser Ile Asp Pro Gln Val Lys Asn Phe Gln Trp
            180                 185                 190
Gly Asp Leu Ile Arg Ala Ile Gln Glu Thr His Asp Arg Gly Phe Glu
        195                 200                 205
Leu Pro Leu Leu Leu Asp Cys Asp Asn Leu Leu Ala Glu Gly Pro Gly
210                 215                 220
Phe Asn Val Val Val Ile Lys Asp Gly Val Val Arg Ser Pro Gly Arg
225                 230                 235                 240
Ala Ala Leu Pro Gly Ile Thr Arg Lys Thr Val Leu Glu Ile Ala Glu
                245                 250                 255
Ser Leu Gly His Glu Ala Ile Leu Ala Asp Ile Thr Pro Ala Glu Leu
            260                 265                 270
Tyr Asp Ala Asp Glu Val Leu Gly Cys Ser Thr Gly Gly Gly Val Trp
        275                 280                 285
Pro Phe Val Ser Val Asp Gly Asn Ser Ile Ser Asp Gly Val Pro Gly
    290                 295                 300
Pro Val Thr Gln Ser Ile Ile Arg Arg Tyr Trp Glu Leu Asn Val Glu
305                 310                 315                 320
Pro Ser Ser Leu Leu Thr Pro Val Gln Tyr
                325                 330
```

<210> SEQ ID NO 77
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 77

```
atggctttct cagctgacac ccctgaaatc gtttacaccc acgacaccgg tctggactat      60
atcacctact ctgactacga actggacccg gctaacccgc tggctggtgg tgctgcttgg     120
```

```
atcgaaggtg ctttcgttcc gccgtctgaa gctcgtatct ctatcttcga ccagggtttt      180
tatacttctg acgctaccta caccaccttc cacgtttgga acggtaacgc tttccgtctg      240
ggggaccaca tcgaacgtct gttctctaat gcggaatcta ttcgtttgat cccgccgctg      300
acccaggacg aagttaaaga gatcgctctg gaactggttg ctaaaaccga actgcgtgaa      360
gcgatcgttt ctgtttctat cacccgtggt tactcttcta ccccattcga gcgtgacatc      420
accaaacatc gtccgcaggt ttacatgtat gctgttccgt accagtggat cgtaccgttt      480
gaccgcatcc gtgacggtgt tcacctgatg gttgctcagt cagttcgtcg tacaccgcgt      540
agctctatcg acccgcaggt taaaaacttc cagtggggtg acctgatccg tgcaattcag      600
gaaacccacg accgtggttt cgagtgtccg ctgctgctgg actgcgacaa cctgctggct      660
gaaggtccgg gtttcaacgt tgttgttatc aaagacggtg ttgttcgttc tccgggtcgt      720
gctactctgc cgggtatcac ccgtaaaacc gttctggaaa tcgctgaatc tctgggtcac      780
gaagctatcc tggctgacat caccccggct gaactgtacg acgctgacga agttctgggt      840
tgctcaaccg gtggtggtgt ttggccgttc gtttctgttg acggtaactc tatctctgac      900
ggtgttccgg gtccggttac ccagtctatc atccgtcgtt actgggaact gaacgttgaa      960
ccttcttctc tgctgacccc ggtacagtac                                       990
```

<210> SEQ ID NO 78
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 78

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205
```

```
Cys Pro Leu Leu Leu Asp Cys Asp Asn Leu Leu Ala Glu Gly Pro Gly
            210                 215                 220

Phe Asn Val Val Val Ile Lys Asp Gly Val Val Arg Ser Pro Gly Arg
225                 230                 235                 240

Ala Thr Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
            275                 280                 285

Pro Phe Val Ser Val Asp Gly Asn Ser Ile Ser Asp Gly Val Pro Gly
        290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 79
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 79
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccaccttc cacgtttgga acgtaacgc tttccgtctg      240 ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
gcgatcgttc tggtttctat cacccgtggt tactcttcta ccccattcga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagctgccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat cacccccggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                       990

<210> SEQ ID NO 80
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 80
```

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
                20                  25                  30

Pro Leu Ala Gly Gly Ala Ala Trp Ile Glu Gly Ala Phe Val Pro Pro
            35                  40                  45

Ser Glu Ala Arg Ile Ser Ile Phe Asp Gln Gly Phe Tyr Thr Ser Asp
50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
                100                 105                 110

Val Ala Lys Thr Glu Leu Arg Glu Ala Ile Val Leu Val Ser Ile Thr
            115                 120                 125

Arg Gly Tyr Ser Ser Thr Pro Phe Glu Arg Asp Ile Thr Lys His Arg
            130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
                180                 185                 190

Gly Asp Leu Ile Arg Ala Ile Gln Glu Thr His Asp Arg Gly Phe Glu
            195                 200                 205

Leu Pro Leu Leu Leu Asp Cys Asp Asn Leu Leu Ala Glu Gly Pro Gly
210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
            275                 280                 285

Pro Phe Val Ser Val Asp Gly Asn Ser Ile Ser Asp Gly Val Pro Gly
            290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 81
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 81
atggctttct cagctgacac ccctgaaatc gtttacaccc acgacaccgg tctggactat     60
atcacctact ctgactacga actggacccg gctaacccgc tggctggtgg tgctgcttgg    120
atcgaaggtg ctttcgttcc cgccgtctga agctcgtatct ctatcttcga ccagggtttt    180

```
tatacttctg acgctaccta caccaccttc cacgtttgga acggtaacgc tttccgtctg    240
ggggaccaca tcgaacgtct gttctctaat gcggaatcta ttcgtttgat cccgccgctg    300
acccaggacg aagttaaaga gatcgctctg gaactggttg ctaaaaccga actgcgtgaa    360
gcgatcgttt ctgtttctat cacccgtggt tactcttcta ccccatggga gcgtgacatc    420
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagctgccg ctgctgctgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg tggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                     990
```

<210> SEQ ID NO 82
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 82

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Trp Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220
```

Phe Asn Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
            245                 250                 255

Ser Leu Gly His Glu Ala Ile Leu Ala Asp Ile Thr Pro Ala Glu Leu
        260                 265                 270

Tyr Asp Ala Asp Glu Val Leu Gly Cys Ser Thr Gly Gly Val Trp
    275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 83
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 83
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccaccttc cacgtttgga cggtaacgc tttccgtctg      240 ggggaccaca tcgaacgtct gttctctaat gcggaatcta ttcgtttgat cccgccgctg     300
acccaggacg aagttaaaga tcgctctg gaactggttg ctaaaaccga actgcgtgaa       360
gcgatcgttg tggtttctat cacccgtggt tactcttcta ccccattcga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc agtggggtg acctgatccg tgcaattcag      600
gaaacccacg accgtggttt cgagctgccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat cacccgggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                     990

<210> SEQ ID NO 84
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 84

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 85
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 85
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccaccttc cacgtttgga acggtaacgc tttccgtctg     240
ggggaccaca tcgaacgtct gttctctaat gcggaatcta ttcgttttga tccgccgctg     300

```
acccaggacg aagttaaaga gatcgctctg gaactggttg ctaaaaccga actgcgtgaa    360
gcgatcgttt ctgtttctat cacccgtggt tactcttcta ccccattcga gcgtgacatc    420
accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcatttcag    600
gaaacccacg accgtggttt cgagctgccg ctgctgctgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg tggtggtgt ttggccgttc gtttctgttg acggtaactc tatctctgac    900
ggtgttccgg tccggttac ccagtctatc atccgtcgtt actgggaact gaacgttgaa    960
ccttcttctc tgctgacccc ggtacagtac                                      990
```

<210> SEQ ID NO 86  
<211> LENGTH: 330  
<212> TYPE: PRT  
<213> ORGANISM: Artificial Sequence  
<220> FEATURE:  
<223> OTHER INFORMATION: Engineered variant of Arthrobacter transaminase

<400> SEQUENCE: 86

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Phe Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240
```

```
Ala Ala Leu Pro Gly Ile Thr Arg Lys Thr Val Leu Glu Ile Ala Glu
            245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
        290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 87
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 87
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccaccttc acgtttggaa acgtaacgc tttccgtctg      240 ggggaccaca tcgaacgtct gttctctaat gcggaatcta ttcgttttga tcccgccgctg    300 acccaggacg aagttaaaga gatcgctctg gaactggttg ctaaaaccga actgcgtgaa     360
gcgatcgttt ctgtttctat cacccgtggt tactcttcta ccccattcga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtgggggtg aacctgatcc gtcaaggcag    600
gaaacccacg accgtggttt cgagctgccg ctgctgctgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccccgggct gaactgtacg acgctgacga agttctgggt   840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                      990

<210> SEQ ID NO 88
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 88

Met Ala Phe Ser Ala Asp Thr Pro Glu Ile Val Tyr Thr His Asp Thr
1               5                  10                  15

Gly Leu Asp Tyr Ile Thr Tyr Ser Asp Tyr Glu Leu Asp Pro Ala Asn
            20                  25                  30
```

Pro Leu Ala Gly Gly Ala Ala Trp Ile Glu Gly Ala Phe Val Pro Pro
                35                  40                  45

Ser Glu Ala Arg Ile Ser Ile Phe Asp Gln Gly Phe Tyr Thr Ser Asp
 50                  55                  60

Ala Thr Tyr Thr Thr Phe His Val Trp Asn Gly Asn Ala Phe Arg Leu
 65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
                100                 105                 110

Val Ala Lys Thr Glu Leu Arg Glu Ala Ile Val Ser Val Ser Ile Thr
                115                 120                 125

Arg Gly Tyr Ser Ser Thr Pro Phe Glu Arg Asp Ile Thr Lys His Arg
130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
                180                 185                 190

Gly Asp Leu Ile Arg Ala Arg Gln Glu Thr His Asp Arg Gly Phe Glu
                195                 200                 205

Leu Pro Leu Leu Leu Asp Cys Asp Asn Leu Leu Ala Glu Gly Pro Gly
210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
                260                 265                 270

Tyr Asp Ala Asp Glu Val Leu Gly Cys Ser Thr Gly Gly Gly Val Trp
                275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 89
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 89
atggctttct cagctgacac ccctgaaatc gtttacaccc cgacaccgg tctggactat     60 atcacctact ctgactacga actggacccg gctaacccgc tggctggtgg tgctgcttgg    120
atcgaaggtg ctttcgttcc gccgtctgaa gctcgtatct ctatcttcga ccagggtttt    180
tatacttctg acgctaccta caccaccttc acgtttgga acggtaacgc tttccgtctg    240
ggggaccaca tcgaacgtct gttctctaat gcggaatcta ttcgtttgat cccgccgctg    300
acccaggacg aagttaaaga gatcgctctg gaactggttg ctaaaaccga actgcgtgaa    360

```
gcgatcgttt ctgtttctat cacccgtggt tactcttcta ccccattcga gcgtgacatc      420
accaaacatc gtccgcaggt ttacatgtat gctgttccgt accagtggat cgtaccgttt      480
gaccgcatcc gtgacggtgt tcacctgatg gttgctcagt cagttcgtcg tacaccgcgt      540
agctctatcg acccgcaggt taaaaacttc cagtggggtg acctgatccg tgcaattcag      600
gaaacccacg accgtggttt cgagctgccg ctgctgctgg actgcgacaa cctgctggct      660
gaaggtatgg gtttcaacgt tgttgttatc aaagacggtg ttgttcgttc ccgggtcgt       720 gctgctctgc cgggtatcac ccgtaaaacc gttctggaaa tcgctgaatc tctgggtcac      780
gaagctatcc tggctgacat caccccggct gaactgtacg acgctgacga agttctgggt      840
tgctcaaccg gtggtggtgt ttggccgttc gtttctgttg acggtaactc tatctctgac      900
ggtgttccgg tccggttac ccagtctatc atccgtcgtt actgggaact gaacgttgaa       960
ccttcttctc tgctgacccc ggtacagtac                                       990
```

<210> SEQ ID NO 90
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 90

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Met Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255
```

```
Ser Leu Gly His Glu Ala Ile Leu Ala Asp Ile Thr Pro Ala Glu Leu
        260                 265                 270

Tyr Asp Ala Asp Glu Val Leu Gly Cys Ser Thr Gly Gly Val Trp
    275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 91
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 91
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt    180
tatacttctg acgctaccta caccgtcttc acgtttgga acggtaacgc tttccgtctg     240
ggggaccaca tcgaacgtct gttctctaat gcggaatcta ttcgtttgat cccgccgctg     300
acccaggacg aagtgaaaga gatcgctctg gaactggttg ctaaaaccga actgcgtgaa     360
gcgatcgtta tcgtttctat cacccgtggt tactcttcta ccccatggga gcgtgacatc     420
accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc agtgggggtg acctgatccg tgcaattcag     600
gaaacccacg accgtggttt cgagttaccg ctgctgctgg acttcgacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccccggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttcac tgctgacccc ggtacagtac                                     990

<210> SEQ ID NO 92
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 92

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45
```

```
Ser Glu Ala Arg Ile Ser Ile Phe Asp Gln Gly Phe Tyr Thr Ser Asp
 50                  55                  60

Ala Thr Tyr Thr Val Phe His Val Trp Asn Gly Asn Ala Phe Arg Leu
 65                  70                  75                  80

Gly Asp His Ile Glu Arg Leu Phe Ser Asn Ala Glu Ser Ile Arg Leu
                 85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ile Val Ser Ile Thr
        115                 120                 125

Arg Gly Tyr Ser Ser Thr Pro Trp Glu Arg Asp Ile Thr Lys His Arg
130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Phe Asp Asn Leu Leu Ala Glu Gly Pro Gly
210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 93
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 93
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccgtcttc acgtttgga acggtaacgc tttccgtctg     240
ggggaccaca tcgaacgtct gttctctaat gcggaatcta ttcgttttgat cccgccgctg     300 acccaggacg aagttaaaga gatcgctctg gaactggttg ctaaaaccga actgcgtgaa     360
gcgatcgtta tcgtttctat caccgtggt tactcttcta ccccatggga gcgtgacatc     420
accaaacatc gtccgcaggt ttacatgtat gctgttccgt accagtcgat cgtaccgttt     480
```

```
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagttaccg ctgttgctgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacgt cacccccggct gaactgtacg acgctgacga agttctgggt    840
tgctcaaccg tggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                     990
```

<210> SEQ ID NO 94
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 94

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ile Ser Ile Thr
        115                 120                 125

Arg Gly Tyr Ser Ser Thr Pro Trp Glu Arg Asp Ile Thr Lys His Arg
    130                 135                 140

Pro Gln Val Tyr Met Tyr Ala Val Pro Tyr Gln Ser Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Val Thr Pro Ala Glu Leu
            260                 265                 270
```

Tyr Asp Ala Asp Glu Val Leu Gly Cys Ser Thr Gly Gly Val Trp
            275                 280                 285

Pro Phe Val Ser Val Asp Gly Asn Ser Ile Ser Asp Gly Val Pro Gly
        290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 95
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 95

```
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccgtcttc acgtttgga acggtaacgc tttccgtctg     240
ggggaccaca tcgaacgtct gttctctaat gcggaatcta ttcgtttgat cccgccgctg     300
acccaggacg aagttaaaga tcgctctg gaactggttg ctaaaaccga actgcgtgaa      360
gcgatcgtta tcgttactat caccgtggt tactcttcta ccccatggga gcgtgacatc     420
accaaacatc gtccgcaggt ttacatgaat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagttaccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaaac gttctggaaa tcgctgaatc tctgggtcac     780
gaagctatcc tggctgacat caccccggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                     990
```

<210> SEQ ID NO 96
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 96

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ile Thr Ile Thr
        115                 120                 125

Arg Gly Tyr Ser Ser Thr Pro Trp Glu Arg Asp Ile Thr Lys His Arg
    130                 135                 140

Pro Gln Val Tyr Met Asn Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 97
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 97
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccgtcttc acgtttgga acggtaacgc tttccgtctg      240
ggggaccaca tcgaacgtct gttctctaat gcggaatcta ttcgttttga tcccgccgctg    300 acccaggacg aagttaaaga gatcgctctg gaactggttg ctaaaaccga actgcgtgaa     360
gcgatcgtta tcgtttctat caccccgtggt tactcttcta ccccatggga gcgtgacatc    420
accaaacatc gtccgcaggt ttacatggcg gctgttccgt accagtggat cgtaccgttt     480
gaccgcatcc gtgacggtgt tcacctgatg gttgctcagt cagttcgtcg tacaccgcgt     540

```
agctctatcg acccgcaggt taaaaacttc cagtggggtg acctgatccg tgcaattcag    600
gaaacccacg accgtggttt cgagttaccg ctgctgctgg actgcgacaa cctgctggct    660
gaaggtccgg gtttcaacgt tgttgttatc aaagacggtg ttgttcgttc ccgggtcgt     720 gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                    990
```

<210> SEQ ID NO 98
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 98

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ile Ser Ile Thr
        115                 120                 125

Arg Gly Tyr Ser Ser Thr Pro Trp Glu Arg Asp Ile Thr Lys His Arg
    130                 135                 140

Pro Gln Val Tyr Met Ala Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285
```

```
Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 99
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 99
atggctttct cagctgacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccgtcttc cacgtttgga acggtaacgc tttccgtctg     240
ggggaccaca tcgaacgtct gttctctaat gcggaatcta ttcgttttga tccgccgctg     300
acccaggacg aagttaaaga gatcgctctg gaactggttg ctaaaaccga actgcgtgaa     360
gcgattgtta ttgttaccat cacccgtggt tactcttcta ccccatggga agtgacatc      420 accaaacatc gtccgcaggt ttacatgtat gctgttccgt accagtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagttaccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaaacc gttctggaaa tcgctgaatc tctgggtcac     780
gaagctatcc tggctgacat cacccccggct gaactgtacg acgctgacga agttctgggt     840
tgctcaaccg tggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                      990

<210> SEQ ID NO 100
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 100

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
                20                  25                  30

Pro Leu Ala Gly Gly Ala Ala Trp Ile Glu Gly Ala Phe Val Pro Pro
            35                  40                  45

Ser Glu Ala Arg Ile Ser Ile Phe Asp Gln Gly Phe Tyr Thr Ser Asp
        50                  55                  60

Ala Thr Tyr Thr Val Phe His Val Trp Asn Gly Asn Ala Phe Arg Leu
65                  70                  75                  80
```

Gly Asp His Ile Glu Arg Leu Phe Ser Asn Ala Glu Ser Ile Arg Leu
            85                  90                  95

Ile Pro Pro Leu Thr Gln Asp Glu Val Lys Glu Ile Ala Leu Glu Leu
        100                 105                 110

Val Ala Lys Thr Glu Leu Arg Glu Ala Ile Val Ile Val Thr Ile Thr
        115                 120                 125

Arg Gly Tyr Ser Ser Thr Pro Trp Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 101
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 101
atggctttct cagctgacac ccctgaaatc gtttacaccc acgacaccgg tctggactat     60
atcacctact ctgactacga actggacccg gctaacccgc tggctggtgg tgctgcttgg    120
atcgaaggtg ctttcgttcc gccgtctgaa gctcgtatct ctatcttcga ccagggtttt    180
tatacttctg acgctaccta caccgtcttc acgtttgga acgtaacgc tttccgtctg    240 ggggaccaca tcgaacgtct gttctctaat gcggaatcta ttcgttttgat cccgccgctg    300 acccaggacg aagttaaaga gatcgctctg gaactggttg ctaaaaccga actgcgtgaa    360
gcgatcgtta tcgttgctat cacccgtggt tactcttcta ccccatggga agcgtgacatc    420 accaaacatc gtccgcaggt ttacatgtat gctgttccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagttaccg ctgctgctgg actgcgacaa cctgctggct    660

```
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg tggtggtgt ttggccgttc gtttctgttg acggtaactc tatctctgac    900
ggtgttccgg tccggttac ccagtctatc atccgtcgtt actgggaact gaacgttgaa    960
ccttcttctc tgctgacccc ggtacagtac                                    990
```

```
<210> SEQ ID NO 102
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 102
```

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ile Val Ala Ile Thr
        115                 120                 125

Arg Gly Tyr Ser Ser Thr Pro Trp Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

```
Pro Val Thr Gln Ser Ile Ile Arg Arg Tyr Trp Glu Leu Asn Val Glu
305                 310             315                 320
Pro Ser Ser Leu Leu Thr Pro Val Gln Tyr
                325             330
```

PROCESS FOR PREPARING AMINOCYCLOHEXYL ETHER COMPOUNDS

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "MRL-ACV-00034 SEQ.txt", a creation date of Jul. 13, 2011, and a size of 455,772 bytes. The Sequence Listing filed via EFS-Web is part of the specification and is incorporated in its entirety by reference herein.

BACKGROUND OF THE INVENTION

Arrhythmia is a variation from the normal rhythm of the heart beat and generally represents the end product of abnormal ion-channel structure, number or function. Both atrial arrhythmias and ventricular arrhythmias are known. The major cause of fatalities due to cardiac arrhythmias is the subtype of ventricular arrhythmias known as ventricular fibrillation (VF).

Atrial fibrillation (AF) is the most common arrhythmia seen in clinical practice and is a cause of morbidity in many individuals (Pritchett E. L., N. Engl. J. Med. 327(14):1031 Oct. 1, 1992, discussion 1031-2; Kannel and Wolf, Am. Heart J. 123(1):264-7 Jan. 1992). Its prevalence is likely to increase as the population ages and it is estimated that 3-5% of patients over the age of 60 years have AF (Kannel W. B., Abbot R. D., Savage D. D., McNamara P. M., N. Engl. J. Med. 306(17): 1018-22, 1982; Wolf P. A., Abbot R. D., Kannel W. B. Stroke. 22(8):983-8, 1991). While AF is rarely fatal, it can impair cardiac function and is a major cause of stroke (Hinton R. C., Kistler J. P., Fallon J. T., Friedlich A. L., Fisher C. M., American Journal of Cardiology 40(4):509-13, 1977; Wolf P. A., Abbot R. D., Kannel W. B., Archives of Internal Medicine 147(9):1561-4, 1987; Wolf P. A., Abbot R D., Kannel W. B. Stroke. 22(8):983-8, 1991; Cabin R. S., Clubb K. S., Rall C., Perlmutter R A., Feinstein A. R, American Journal of Cardiology 65(16): 1112-6, 1990).

Antiarrhythmic agents have been developed to prevent or alleviate cardiac arrhythmia.

WO95/08544 discloses a class of aminocyclohexylester compounds as useful for the treatment of arrhythmias.

WO93/19056 discloses a class of aminocyclohexylamides as useful in the treatment of arrhythmia and in the inducement of local anaesthesia.

WO99/50225 and WO 04/099137 disclose aminocyclohexylether compounds as being useful for the treatment of arrhythmias.

WO06/138673 and WO 06/88525 describe processes for preparing aminocyclohexylether compounds This invention relates to a process for preparing aminocyclohexyl ether compounds via functionalization of a cyclohexyl amine. The invention is also related to a process that utilizes etherification of a racemic intermediate, as well as a dynamic kinetic resolution-transamination step. The instant invention is less expensive than previous processes since provides a stereoselective product using inexpensive starting materials.

SUMMARY OF THE INVENTION

The present invention relates to a process for preparing aminocyclohexyl ether compounds of Formula I:

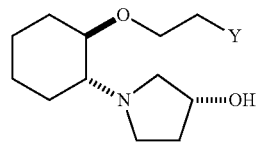

or the pharmaceutically acceptable salts and esters thereof. In particular, the instant invention is directed towards a process for preparing (1R,2R)-2-[(3R)-Hydroxypyrrolidinyl]-1-(3,4-dimethoxyphenethoxy)-cyclohexane

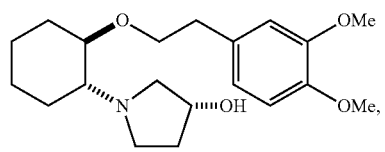 [SMILES: COc1ccc(CCO[C@@H]2CCCC[C@H]2N2CC[C@@H](O)C2)cc1OC]

as well as various intermediates. For brevity, this compound may also be referred to herein as "Compound A." Additional objects will be evident from the following detailed description.

BRIEF DESCRIPTION OF THE FIGURES

FIG. 1 is a characteristic X-ray diffraction pattern (XRPD) of the crystalline D-malate salt of

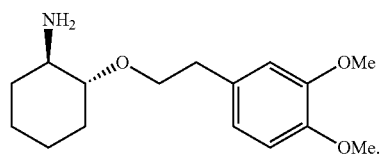 [SMILES: COc1ccc(CCO[C@@H]2CCCC[C@H]2N)cc1OC]

Figure 2:
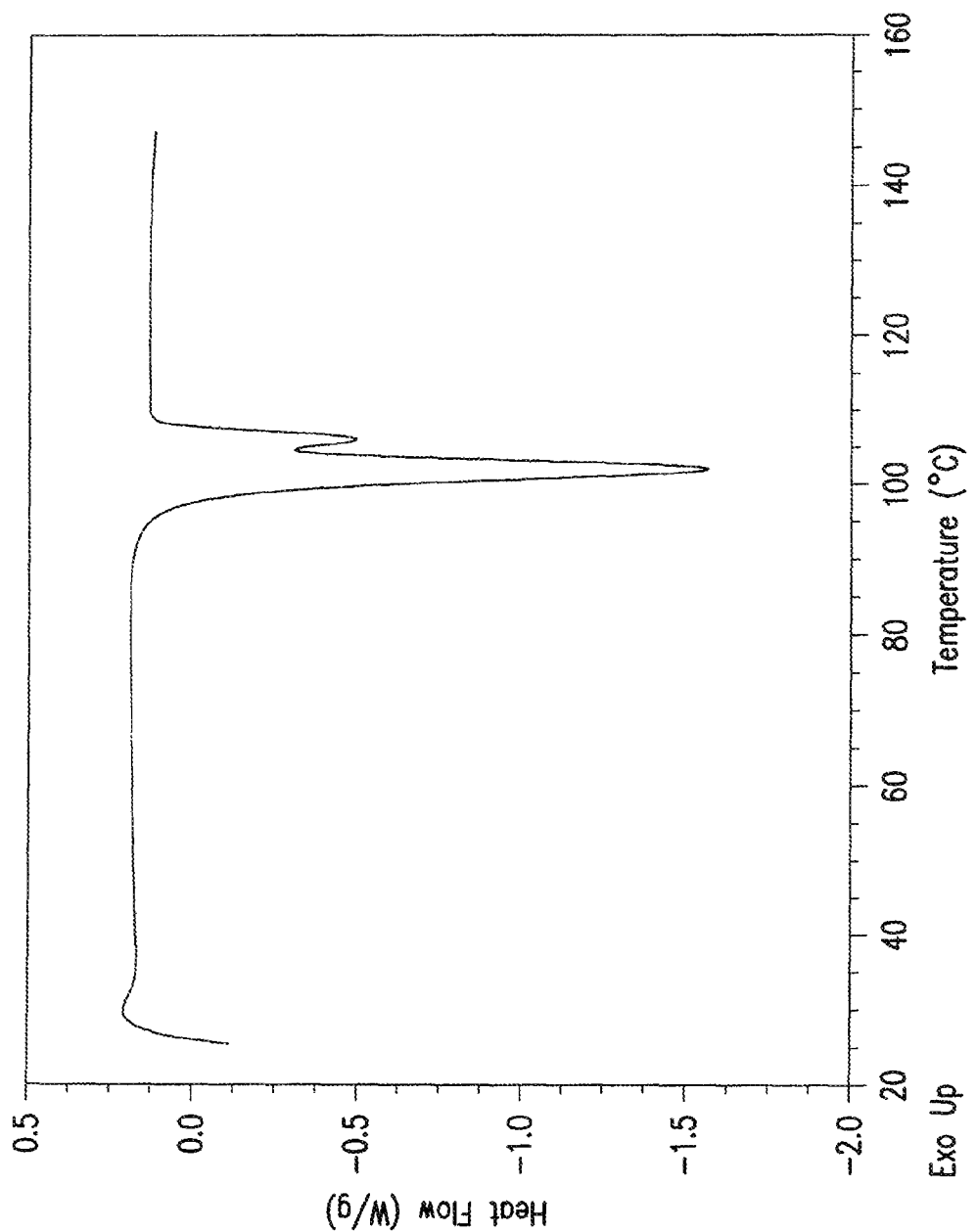

FIG. 2 is a typical differential scanning calorimetry (DSC) curve of the crystalline D-malate salt of

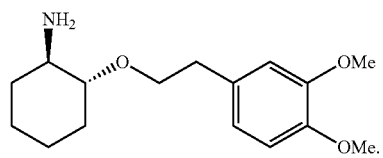 [SMILES: COc1ccc(CCO[C@@H]2CCCC[C@H]2N)cc1OC]

DETAILED DESCRIPTION OF THE INVENTION

An embodiment of the instant inventions is a process for preparing preparing aminocyclohexyl ether compounds of Formula I:

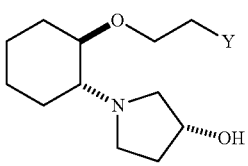

where Y is selected from 3,4-dimethoxyphenyl, 3,4-dihydroxyphenyl or a 3,4-dihalophenyl, comprising the steps of:
  a) Mixing a cyclohexyl amine (iv)

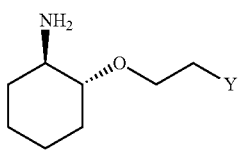

with a malic acid derivative (v)

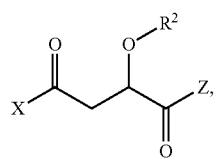

where $R^2$ is selected from hydrogen, esters, carbonates, carbamates, silyl ethers, phosphates or sulfates and where X and Z are independently selected from OH, $C_1$-$C_6$ alkoxy, esters, halides or O-acyl, said X and Z may optionally be joined to form a ring (v-a)

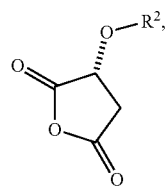

to obtain a hydroxy succinimide (vi)

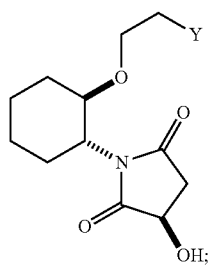

and
  b) reducing the hydroxy succinimide (vi) to obtain a compound of Formula I.

In an embodiment, the process for preparing a compound of Formula I comprises the steps of
  a) mixing an alkoxy ketone (iii)

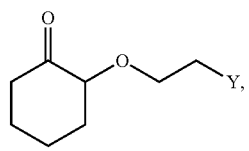

where Y is selected from 3,4-dimethoxyphenyl, 3,4-dihydroxyphenyl or a 3,4-dihalophenyl, with a co-factor, a transaminase polypeptide and an amine to produce a cyclohexyl amine (iv)

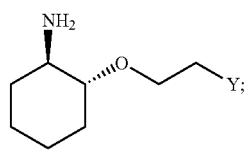

b) mixing the cyclohexyl amine (iv) with a malic acid derivative (v)

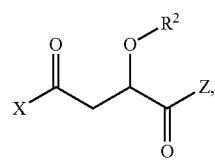

where $R^2$ is selected from hydrogen, esters, carbonates, carbamates, silyl ethers, phosphates or sulfates, and where X and Z are independently selected from OH, $C_1$-$C_6$ alkoxy, esters, halides or O-acyl, said X and Z may optionally be joined to form a ring (v-a)

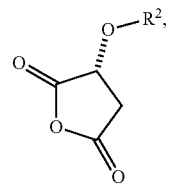

to obtain a hydroxy succinimide (vi)

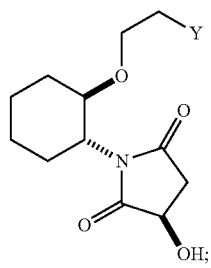

and c) reducing the hydroxy succinimide (vi) to obtain a compound of Formula I.

In a further embodiment, the process for preparing a compound of Formula I comprises the steps of:

a) mixing a substituted cycloalkanone (i)

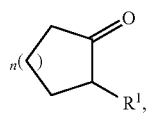

where $R^1$ is an activated leaving group and integer n is selected from 1, 2, or 3, with a substituted ethanol (ii)

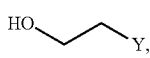

where Y is selected from 3,4-dimethoxyphenyl, 3,4-dihydroxyphenyl or a 3,4-dihalophenyl, in the presence of a metal salt and an organic base to form an alkoxy ketone (iii)

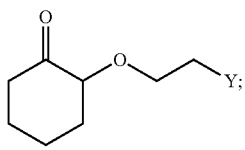

b) mixing the alkoxy ketone (iii) with a co-factor, a transaminase polypeptide and an amine to produce a cyclohexyl amine (iv)

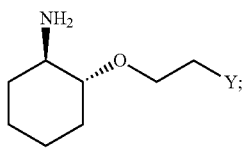

c) mixing the cyclohexyl amine (iv) with a malic acid derivative (v)

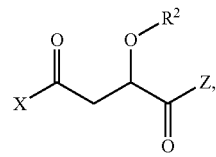

where $R^2$ is selected from hydrogen, esters, carbonates, carbamates, silyl ethers, phosphates or sulfates, and where X and Z are independently selected from OH, $C_1$-$C_6$ alkoxy, esters, halides or O-acyl, said X and Z may optionally be joined to form a ring (v-a)

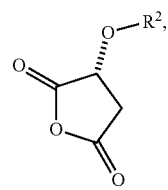

to obtain a hydroxy succinimide (vi)

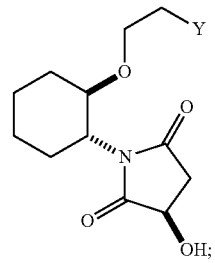

and d) reducing the hydroxy succinimide (vi) to obtain a compound of Formula I.

In a further embodiment, the process of the instant invention further comprises in step b) mixing the alkoxy ketone (iii) with the co-factor, and a slurry containing the transaminase polypeptide in a basic buffer and an amine.

In a further embodiment, the process of the instant invention further comprises adding an acid activator to step c.

In a further embodiment, the process of the instant invention further comprises adding a metal hydride to the hydroxy succinimide (vi) to obtain a compound of Formula I.

In a further embodiment of the instant process, the transaminase polypeptide comprises an amino acid sequence having at least 80% sequence identity to the reference polypeptide of SEQ ID NO: 6.

In a further embodiment of the instant process, the transaminase polypeptide comprises an amino acid sequence having at least 80% sequence identity to the reference polypeptide of SEQ ID NO: 6 and an amino acid residue difference as compared to SEQ ID NO: 6 at one or more of the following positions: X2; X4; X5; X7; X8; X9; X10; X11; X14; X22; X28; X37; X38; X41; X42; X44; X52; X54; X55; X56; X58; X69; X94; X99; X108; X124; X126; X135; X136; X141; X142; X150; X155; X156; X157; X164; X165; X171; X182; X199; X209; X210; X213; X215; X217; X218; X223; X245; X257; X265; X267; X296; and X328.

In a further embodiment, the invention is related to a process comprising the steps of:

a) Mixing a substituted ethanol (ii)

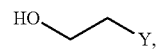

where Y is selected from 3,4-dimethoxyphenyl, 3,4-dihydroxyphenyl or a 3,4-dihalophenyl, with a zinc salt, a secondary amine and an organic base in a first solvent;

b) Adding a solution of a substituted cycloalkanone (i)

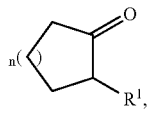

where $R^1$ is an activated leaving group and integer n is 2, to obtain a mixture;

c) Heating the mixture to about 60 to about 150° C. and then cooling the mixture to less than about 60° C.;

d) Adding an acidic aqueous solution to create a biphasic mixture and discarding the aqueous phase;

e) Adding a second solvent to obtain an alkoxy ketone (iii)

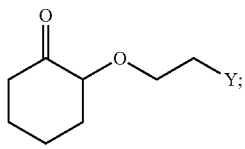

f) Mixing a co-factor with a slurry of a transaminase polypeptide in a basic buffer and a primary amine to produce a solution;

g) Adding the alkoxy ketone (iii) in a second solvent to the solution of step f);

h) Adding a third solvent to create a biphasic mixture and discarding the aqueous layer;

i) Washing the organic layer from step h) with a basic aqueous solution and discarding the aqueous layer;

j) Performing a solvent switch from the third solvent to a fourth solvent;

k) Adding an acid to create a slurry;

l) Filtering the slurry to obtain cyclohexyl amine salt (iv-a);

m) Adding the cyclohexyl amine salt (iv-a) to a mixture of a first solvent and a basic aqueous solution and discarding the aqueous layer;

n) Adding a malic acid derivative, which is selected from malic acid or (v-a)

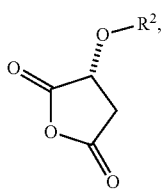

in a first solvent to the cyclohexyl amine (iv-a) in a first solvent;

o) Adding an acid activator;

p) Adding a fourth solvent to obtain hydroxy succinimide (vi)

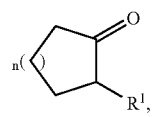

q) Mixing a metal hydride, an additive and an acid, which is selected from a Lewis acid or a protic acid, with a solution of the hydroxy succinimide (vi);

r) Adding a fifth solvent and a basic aqueous solution to obtain a biphasic mixture and discarding the aqueous layer to obtain Compound A

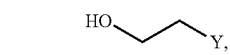

and s) Adding an acid to obtain the salt of Compound A.

In another embodiment of the instant invention, the process for preparing Compound A

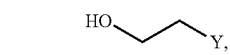

comprises the stets of:

a) Mixing a substituted ethanol (ii)

$$HO\diagdown\diagup Y,$$

where Y is selected from 3,4-dimethoxyphenyl, 3,4-dihydroxyphenyl or 3,4-dihalophenyl, with a zinc salt, a secondary amine and an organic base in a first solvent;

b) Adding a substituted cycloalkanone (i)

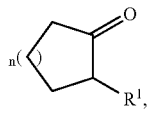

where $R^1$ is an activated leaving group and integer n is 2, to obtain a mixture;

c) Adding an acidic aqueous solution to create a biphasic mixture and discarding the aqueous layer;
d) Adding a second solvent to obtain an alkoxy ketone (iii)

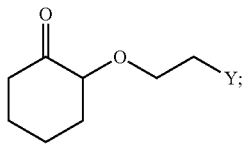

e) Mixing a co-factor with a slurry of a transaminase polypeptide in a basic buffer and an amine to produce a solution;
f) Adding the alkoxy ketone (iii)

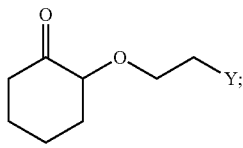

g) Adding a third solvent to create a biphasic mixture and discarding the aqueous layer;
h) Performing a solvent switch from the third solvent to a fourth solvent to obtain cyclohexyl amine (iv)

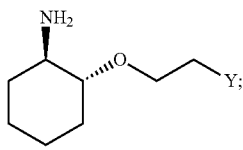

i) Adding an acid to create a slurry;
j) Filtering the slurry to obtain cyclohexyl amine salt (iv-a);
k) Adding cyclohexyl amine salt iv-a to a mixture of a second solvent and an inorganic base followed by a 1,4-dielectrophile of formula vii-a or vii-b

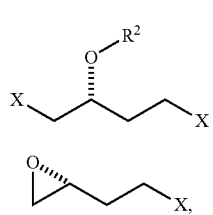

where $R^2$ is selected from hydrogen, esters, carbonates, carbamates, silyl ethers, phosphates or sulfates and X is an activated leaving group;
l) Adding a fifth solvent and a basic aqueous solution to obtain a biphasic mixture and discarding the aqueous layer;
m) Adding an acid to obtain the salt of compound A.

In a further embodiment of the instant process, a transaminase polypeptide having an amino acid sequence of SEQ ID NO: 18 is used.

In a further embodiment of the instant process, a transaminase polypeptide having a polynucleotide sequence of SEQ ID NO: 17 is used.

In a further embodiment of the instant process, a transaminase polypeptide having an amino acid sequence of SEQ ID NO: 206 is used.

In a further embodiment of the instant process, a transaminase polypeptide having a polynucleotide sequence of SEQ ID NO: 205 is used.

In further embodiment of the instant invention, the process for preparing Compound A

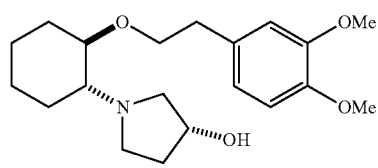 [SMILES: COc1ccc(CCO[C@@H]2CCCC[C@H]2N2CC[C@@H](O)C2)cc1OC]

comprises the steps of:
a) Mixing 3,4-dimethoxyphenyl ethanol with zinc chloride, diisopropylethylamine and pyrrolidine in toluene;
b) Adding 2-chlorocyclohexanone to obtain a mixture;
c) Adding aqueous hydrochloric acid and discarding the aqueous layer to obtain 2-(3,4-dimethoxyphenyl ethoxy)-cyclohexanone;
d) Adding PLP to a slurry of a transaminase polypeptide having SEQ ID NO: 18, in sodium tetraborate and isopropylamine to produce a solution;
e) Mixing 2-(3,4-dimethoxyphenyl ethoxy)-cyclohexanone with the solution of step d);
f) Adding a mixture of IPA and MTBE to create a biphasic mixture and discarding the aqueous layer;
g) Performing a solvent switch on the organic layer from the mixture of IPA and MTBE to a fourth solvent, which is selected from sec-butanol or isopropanol, to obtain a solution;
h) Adding a solution of maleic acid in a fourth solvent to the solution of step g) to obtain 2-(3,4-dimethoxyphenylethoxy)-cyclohexylammonium maleate;
i) Mixing 2-(3,4-dimethoxyphenylethoxy)-cyclohexylammonium maleate with a first solvent and a basic aqueous solution and discarding the aqueous layer to obtain 2-(3,4-dimethoxyphenylethoxy)-cyclohexylamine;
j) Adding R-acetoxy malic acid anhydride to 2-(3,4-dimethoxyphenylethoxy)-cyclohexylamine;
k) Adding acetyl chloride;
l) Adding the fourth solvent, which is selected from ethanol or isopropanol, to obtain 1-{2-[2-(3,4-dimethoxyphenyl)-ethoxy]-cyclohexyl}-3-hydroxypyrrolidine-2,5-dione;
m) Mixing 1-{2-[2-(3,4-dimethoxyphenyl)-ethoxy]-cyclohexyl}-3-hydroxypyrrolidine-2,5-dione with sodium borohydride, trimethylborate and an acid, which is selected from $BF_3OEt_2$ or $BF_3THF$, in THF;
n) Adding water;
o) Adding a basic aqueous solution, which is selected from sodium hydroxide or ammonia, and IPAc, to obtain a biphasic mixture and discarding the aqueous layer to obtain Compound A; and
p) Adding hydrochloric acid to obtain the salt of Compound A.

In a further embodiment, the process comprises, in step e) above, mixing 2-(3,4-dimethoxyphenyl ethoxy)-cyclohexanone in a second solvent, which is selected from DMSO, ethanol or isopropanol, with the solution of step d).

In a further embodiment, the invention is related to a process comprising the steps of:

a) Mixing a substituted ethanol (ii)

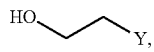

where Y is selected from 3,4-dimethoxyphenyl, 3,4-dihydroxyphenyl or a 3,4-dihalophenyl, with a zinc salt, a secondary amine and an organic base in a first solvent;

b) Adding a solution of a substituted cycloalkanone (i)

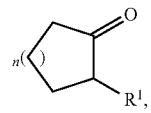

where R¹ is an activated leaving group and integer n is 2, to obtain a mixture;

c) Adding an acidic aqueous solution and discarding the aqueous phase to obtain an alkoxy ketone (iii)

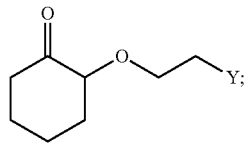

d) Mixing a co-factor with a slurry of a transaminase polypeptide in a basic buffer and a primary amine to produce a solution;

e) Adding the alkoxy ketone (iii) in a second solvent to the solution of step d);

f) Adding a third solvent to create a biphasic mixture and discarding the aqueous layer;

g) Washing the organic layer from step f) with a basic aqueous solution and discarding the aqueous layer;

h) Performing a solvent switch from the third solvent to a fourth solvent;

i) Adding D-malic acid in a fourth solvent to obtain cyclohexyl amine D-malate salt (iv-c)

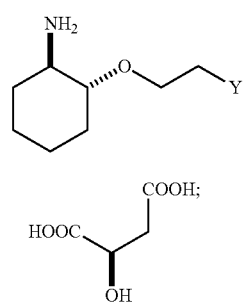

j) Mixing the cyclohexyl amine D-malate salt (iv-c) with a sixth solvent and adding a catalytic amount of an acid activator;

k) Adding HMDS and a Lewis acid to obtain hydroxy succinimide (vi)

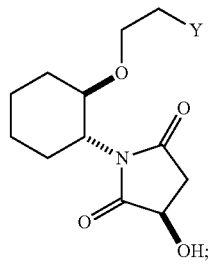

l) Mixing a metal hydride, an additive and an acid, which is selected from a Lewis acid or a protic acid, with a solution of the hydroxy succinimide (vi);

m) Adding a fifth solvent and a basic aqueous solution to obtain a biphasic mixture and discarding the aqueous layer to obtain Compound A

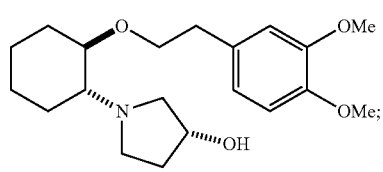 [SMILES: COc1ccc(CCO[C@@H]2CCCC[C@H]2N2CC[C@@H](O)C2)cc1OC]

and n) Adding an acid to obtain the salt of Compound A.

In a further embodiment, the cyclohexyl amine D-malate salt (iv-c)

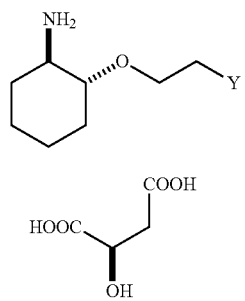

is isolated as the crystalline form.

In further embodiment of the instant invention, the process for preparing Compound A

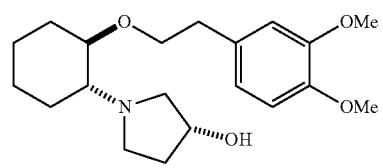 [SMILES: COc1ccc(CCO[C@@H]2CCCC[C@H]2N2CC[C@@H](O)C2)cc1OC]

comprises the steps of:

a) Mixing 3,4-dimethoxyphenyl ethanol with zinc chloride, diisopropylethylamine and pyrrolidine in toluene;

b) Adding 2-chlorocyclohexanone to obtain a mixture;

c) Adding aqueous hydrochloric acid and discarding the aqueous layer to obtain 2-(3,4-dimethoxyphenyl ethoxy)-cyclohexanone;

d) Adding PLP to a slurry of a transaminase polypeptide having SEQ ID NO: 206, in sodium tetraborate and isopropylamine to produce a solution;
e) Mixing 2-(3,4-dimethoxyphenyl ethoxy)-cyclohexanone with the solution of step d);
f) Adding a mixture of IPA and MTBE to create a biphasic mixture and discarding the aqueous layer;
g) Performing a solvent switch on the organic layer from the mixture of IPA and MTBE to a fourth solvent, which is selected from sec-butanol or isopropanol, to obtain a solution;
h) Adding a solution of D-malic acid in a fourth solvent to the solution of step g) to obtain 2-(3,4-dimethoxyphenylethoxy)-cyclohexylammonium malate;
i) Mixing 2-(3,4-dimethoxyphenylethoxy)-cyclohexylammonium malate with an ester solvent and adding a catalytic amount of an alkyl boronic acid;
j) Heating to about 90 to about 125° C., then cooling to about 70° C.;
k) Adding HMDS and a Lewis acid to obtain 1-{2-[2-(3,4-dimethoxyphenyl)-ethoxy]-cyclohexyl}-3-hydroxy-pyrrolidine-2,5-dione, where said Lewis acid is zinc chloride, iron(II) chloride, lithium chloride, copper(II) trifluoromethanesulfonate, iron(III) chloride, iron(II) bromide, zinc bromide, zinc acetate or zinc trifluoromethanesulfonate;
l) Mixing 1-{2-[2-(3,4-dimethoxyphenyl)-ethoxy]-cyclohexyl}-3-hydroxypyrrolidine-2,5-dione with sodium borohydride, trimethylborate and an acid, which is selected from BF$_3$OEt$_2$ or BF$_3$THF, in THF;
m) Adding water;
n) Adding a basic aqueous solution, which is selected from sodium hydroxide or ammonia, and IPAc, to obtain a biphasic mixture and discarding the aqueous layer to obtain Compound A; and
o) Adding hydrochloric acid to obtain the salt of Compound A.

In a further embodiment, the Lewis acid in step k) above is zinc chloride.

In further embodiment of the instant invention, the process for preparing Compound A

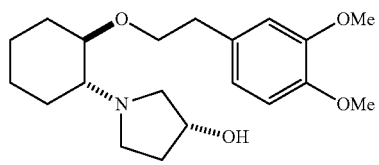 [SMILES: COc1ccc(CCO[C@@H]2CCCC[C@H]2N2CC[C@@H](O)C2)cc1OC]

comprises the steps of:
a) Mixing 3,4-dimethoxyphenyl ethanol with zinc chloride, diisopropylethylamine and pyrrolidine in toluene;
b) Adding 2-chlorocyclohexanone to obtain a mixture;
c) Adding aqueous hydrochloric acid and discarding the aqueous layer to obtain 2-(3,4-dimethoxyphenyl ethoxy)-cyclohexanone;
d) Adding PLP to a slurry of a transaminase polypeptide, said transaminase polypeptide having SEQ ID NO: 18 or SEQ ID NO: 206, in sodium tetraborate and isopropylamine to produce a solution;
e) Mixing 2-(3,4-dimethoxyphenyl ethoxy)-cyclohexanone with the solution of step d);
f) Adding a mixture of IPA and MTBE to create a biphasic mixture and discarding the aqueous layer;
g) Performing a solvent switch on the organic layer from the mixture of IPA and MTBE to a fourth solvent, which is selected from sec-butanol or isopropanol, to obtain a solution;
h) Adding a solution of oxalic acid in the fourth solvent, which is selected from sec-butanol or isopropanol, to the solution of step g to obtain 2-(3,4-dimethoxyphenylethoxy)-cyclohexylammonium oxalate iv-b;
i) Adding 2-(3,4-dimethoxyphenylethoxy)-cyclohexylammonium oxalate iv-b to a mixture of DMAc and potassium bicarbonate followed by (R)-1,4-dibromo-butan-2-ol;
j) Adding IPAc and a basic aqueous solution to obtain a biphasic mixture and discarding the aqueous layer to obtain Compound A; and
k) Adding hydrochloric acid to obtain the salt of Compound A.

In reference to the present disclosure, the technical and scientific terms used in the descriptions herein will have the meanings commonly understood by one of ordinary skill in the art, unless specifically defined otherwise. Accordingly, the following terms are intended to have the following meanings:

As used herein, a substituted cycloalkanone (i) is cycloalkanone of formula (i)

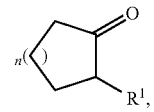

where R$^1$ is an activated leaving group and integer n is selected from 1, 2, or 3. In a further embodiment, integer n is 2. When integer n is 1, the ring size of the cycloalkanone may be expanded, using techniques known in the art (Tiffeneau-Demjanov rearrangement, Krow, G. R. Tetrahedron 1987, 43, 3-38; Fattori, D.; Henry, S.; Vogel, P. Tetrahedron 1993, 49, 1649-1664.) When integer n is 3, the ring size of the cycloalkanone may be contracted, using techniques known in the art. (Wolff rearrangement—Gill, G. B. The Wolff rearrangement. in Comp. Org. Synth. (eds. Trost, B. M; Fleming, I.), 3, 887-912 (Pergamon, Oxford, 1991); Ye, T.; McKervey, M. A. Chem. Rev. 1994, 94, 1091-1160) (Favorskii rearrangement—Mann, J. The Favorskii Rearrangement in Comp. Org. Synth. (eds. Trost, B. M; Fleming, I.), 3, 839-861 (Pergamon Press, Oxford, 1991)). Examples of an activated leaving group include, but are not limited to, chloride, bromide, iodide, mesylate, tosylate, triflate and the like. In an embodiment, a substituted cyclohexanone is selected from 2-chlorocyclohexanone, 2-cyclohexanone methanesulfonate or 2-cyclohexanone p-methylphenylsulfonate. In a further embodiment, the substituted cycloalkanone is 2-chlorocyclohexanone.

As used herein, a substituted ethanol (ii) is a compound of formula (ii)

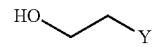

where Y is phenyl, optionally substituted with one or two substituents selected from halogen or OR, where R is hydrogen, alkyl or aryl ether, alkyl or aryl ester, carbonate, carbamate, sulfonate, phosphate. In an embodiment, Y is selected from 3,4-dimethoxyphenyl, 3,4-dihydroxyphenyl or 3,4-dihalophenyl. In a further embodiment, the substituted ethanol is 3,4-dimethoxyphenyl ethanol.

As used herein except where noted, "alkyl" is intended to include both branched- and straight-chain saturated aliphatic hydrocarbon groups having from 1 to 6 carbon atoms. Commonly used abbreviations for alkyl groups are used throughout the specification, e.g. methyl may be represented by conventional abbreviations including "Me" or $CH_3$ or a symbol that is an extended bond without defined terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_1$-$C_6$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. If no number is specified, 1-10 carbon atoms are intended for linear or branched alkyl groups. The phrase "$C_{1-6}$ alkyl, wherein the alkyl group may be unsubstituted or substituted with 1-3 fluorine atoms" refers to alkyl groups having 0, 1, 2 or 3 fluorine atoms attached to one or more carbon atoms. The group "$CF_3$", for example, is a methyl group having three fluorine atoms attached the same carbon atom.

"Aryl" unless otherwise indicated, means mono- and bicyclic aromatic rings containing 6-12 carbon atoms. Examples of aryl include, but are not limited to, phenyl, naphthyl, indenyl and the like. "Aryl" also includes monocyclic rings fused to an aryl group. Examples include tetrahydronaphthyl, indanyl and the like. In an embodiment, aryl is phenyl.

Esters are chemical compounds derived by reacting an oxoacid (one containing an oxo group, X=O) with a hydroxyl compound such as an alcohol or phenol. Esters are usually derived from an inorganic acid or organic acid in which at least one —OH (hydroxyl) group is replaced by an —O-alkyl (alkoxy) group, and most commonly from carboxylic acids and alcohols. Basically, esters are formed by condensing an acid with an alcohol.

A carbonate is a salt of carbonic acid, characterized by the presence of the carbonate ion, $CO_3^{2-}$. The name may also mean an ester of carbonic acid, an organic compound containing the carbonate group O=C(O—)$_2$. Examples of a carbonate include, but are not limited to, $H_2CO_3$, $Li_2CO_3$, $Na_2CO_3$, $K_2CO_3$, $MgCO_3$ and the like.

Carbamates are organic compounds which can be derived for examples, but not limited to, by reactions between a carbamic acid ($R^xR^yNCO_2H$) or isocyanates ($R^xN=C=O$) with an alcohol ($R^zOH$) and generally have a formula of $R^xR^yNCO_2R^z$, where $R^x$ and $R^z$ can be, but not limited to, aliphatic (saturated or unsaturated hydrocarbons) or aromatic groups and $R^y$ can be H or aliphatic or aromatic groups. Examples of carbamates are, but not limited to, N-phenylcarbamate ($PhNHCO_2R^z$), N,N-dimethylcarbamate ($Me_2NCO_2R^z$) and the like.

Sulfonates have the general formula of $RSO_2O^-$. Examples of sulfonates include, but are not limited to, mesylate, triflate, tosylate, besylate and the like.

A phosphate is a salt of phosphoric acid and have the general formula of $P(O)(OR)_3$. Examples of phosphates include, but are not limited to sodium phosphate, potassium phosphate, ammonium phosphate and the like.

As used herein, a metal salt is an ionic compound of the form $MX_s$, where M is a transition metal selected from groups IIB to IIIB in the periodic table, X is selected from halide, alkoxide, inflate, mesylate, carboxylate, phosphate and integer s is 1, 2, 3, 4, 5 or 6. Examples of transition metals include Sc, Y, Ti, Nb, Ta, Cr, Mo, W, Mn, Tc, Re, Fe, Ru, Os, Co, Rh, Ir, Ni, Pd, Pt, Cu, Ag, Au, Zn, Cd and Hg. In an embodiment, the metal salt is a zinc salt. Examples include zinc(II) salts, or zinc salts, such as zinc oxide, zinc acetate, zinc phosphate, zinc sulfonates, and zinc halides. In an embodiment, a metal salt is selected from $ZnCl_2$, $ZnBr_2$, ZnO and $Zn(OTf)_2$. In a further embodiment, the metal salt is $ZnCl_2$.

As used herein, an organic base is a nitrogen-centered molecule which acts as a Bronstead base. Examples include pyridine, 2,6-lutidine, tetramethylguanidine, 1,8-diazabicyclo[5.4.0]undec-7-ene, primary-, secondary- and tertiary-alkylamines. In an embodiment, the organic base is selected from tertiary-alkylamines such as triethylamine, tributylamine, trioctylamine, N-methylpyrrolidine, N-methyl morpholine or diisopropylethylamine (DIPEA).

As used herein, an alkoxy ketone (iii) is a compound of formula (iii)

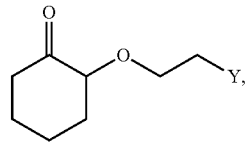

where Y is phenyl, optionally substituted with one or two substituents selected from halogen or OR, where R is hydrogen, alkyl or aryl ether, alkyl or aryl ester, carbonate, carbamate, sulfonate, phosphate. In an embodiment, Y is selected from 3,4-dimethoxyphenyl, 3,4-dihydroxyphenyl or 3,4-dihalophenyl. In a further embodiment, the substituted alkoxy ketone is 2-(3,4-dimethoxyphenyl ethoxy)-cyclohexanone.

As used herein, cyclohexyl amine (iv) is a compound of the type

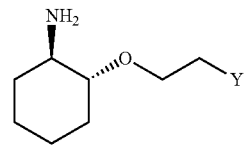

where Y is a phenyl, optionally substituted with one or two substituents selected from halogen or OR, where R is hydrogen, alkyl or aryl ether, alkyl or aryl ester, carbonate, carbamate, sulfonate, phosphate. In an embodiment, Y is selected from 3,4-dimethoxyphenyl, 3,4-dihydroxyphenyl or 3,4-dihalophenyl. In a further embodiment, the cyclohexyl amine is 2-(3,4-dimethoxyphenyl ethoxy)-cyclohexylamine.

In another embodiment, a salt form of the cyclohexyl amine (iv-a) may be used. A salt is formed by the addition of an inorganic or organic protic acid. Examples of such acids include HCl, $H_2SO_4$, oxalic, pivalic, malic or maleic acid. Examples of such a cyclohexyl amine salt include

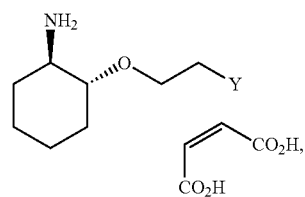

iv-a

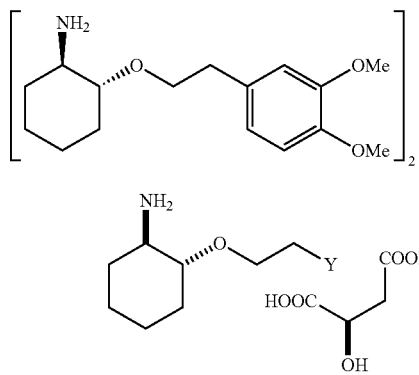

iv-b iv-c

In an embodiment, the cyclohexyl amine is

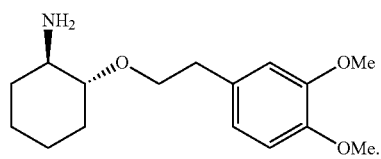 [SMILES: COc1ccc(CCO[C@@H]2CCCC[C@H]2N)cc1OC]

In a further embodiment, the cyclohexyl amine salt is a D-malate salt of

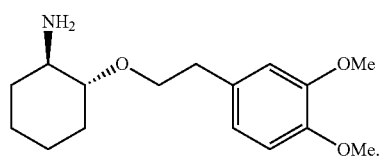 [SMILES: COc1ccc(CCO[C@@H]2CCCC[C@H]2N)cc1OC]

In a further embodiment, the cyclohexyl amine salt is the crystalline D-malate salt of

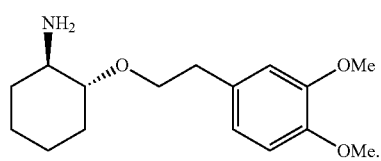 [SMILES: COc1ccc(CCO[C@@H]2CCCC[C@H]2N)cc1OC]

Figure 1:
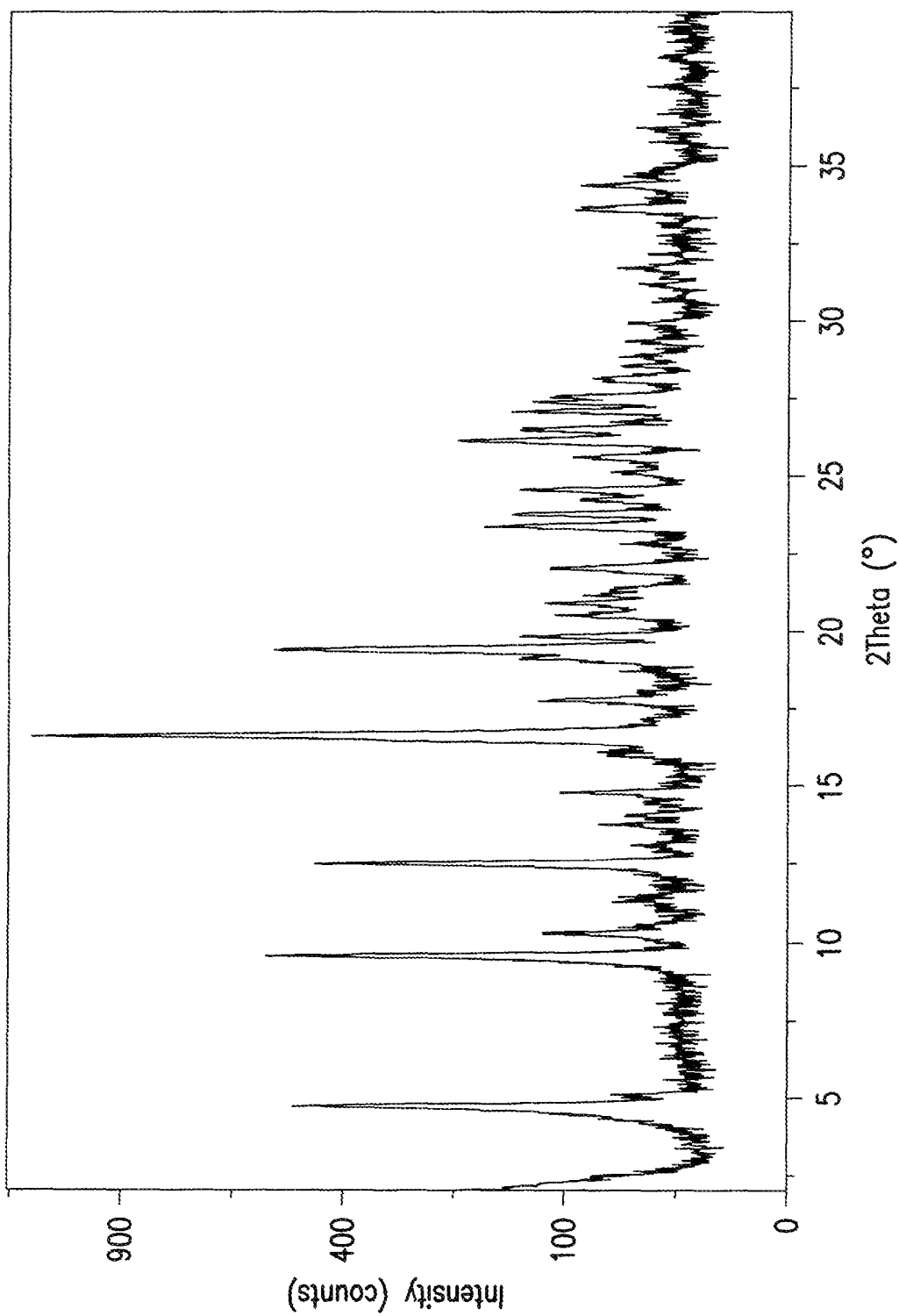

FIG. 1 shows the x-ray diffraction pattern for the crystalline D-malate salt.

The X-ray powder diffraction patterns were generated on a Philips Analytical X'Pert PRO X-ray Diffraction System with PW3040/60 console. A PW3373/00 ceramic Cu LEF X-ray tube K-Alpha radiation was used as the source. Further data for the crystalline D-malate salt of

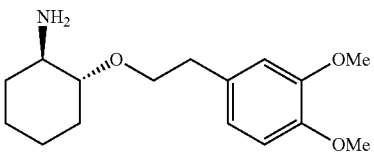 [SMILES: COc1ccc(CCO[C@@H]2CCCC[C@H]2N)cc1OC]

is shown below:

| Pos. [°2Th.] | Height [cts] | d-spacing [Å] | Rel Int. [%] |
|---|---|---|---|
| 16.5 | 1138.2 | 5.38 | 100.0 |
| 9.4 | 493.2 | 9.41 | 43.3 |
| 4.5 | 415.4 | 19.43 | 36.5 |
| 12.3 | 397.7 | 7.18 | 34.9 |
| 23.2 | 169.0 | 3.84 | 14.9 |
| 19.7 | 120.3 | 4.52 | 10.6 |
| 17.6 | 102.2 | 5.04 | 9.0 |
| 10.1 | 99.9 | 8.76 | 8.8 |
| 14.6 | 84.5 | 6.08 | 7.4 |

The crystalline D-malate salt of

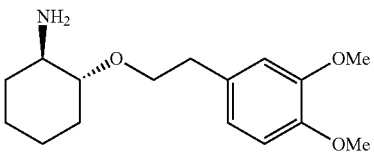

exhibited characteristic diffraction peaks corresponding to at least 6 of the following d-spacings: 5.38, 9.41, 19.43 and 7.18 angstroms.

FIG. 2 shows the characteristic DSC curve for the crystalline D-malate salt of

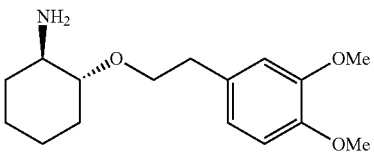

DSC data were acquired using TA Instruments DSC 2910 or equivalent. Between 2 and 6 mg sample was weighed into a pan and covered. This pan was placed at the sample position in the calorimeter cell. An empty pan was placed at the reference position. The calorimeter cell was closed and a flow of nitrogen was passed through the cell. The heating program was set to heat the sample at a heating rate of 10° C./min to a temperature of approximately 300° C. The heating program was started. When the run was completed, the data were analyzed using the DSC analysis program contained in the system software. The thermal events were integrated between baseline temperature points that were above and below the temperature range over which the thermal event is observed. The data reported are the onset temperature, peak temperature and enthalpy.

As used herein, a malic acid derivative (v) is a compound of formula (v)

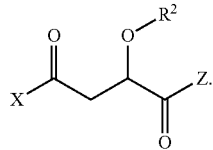

Examples of a malic acid derivative include, but are not limited to structures where $R^2$ is selected from hydrogen, esters, carbonates, carbamates, phosphates or sulfates and where X and Z are independently selected from OH, $C_1$-$C_6$ alkoxy, esters, halides or O-acyl. Additionally X and Z may optionally be joined to form a ring (v-a)

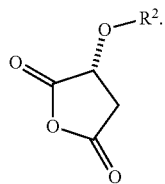

In an embodiment, $R^2$ is $C_1$-$C_6$ alkyl ester. In a further embodiment, a malic acid derivative is selected from R-acetoxy malic acid anhydride, malic acid dimethyl ester or malic acid.

As used herein, a hydroxy succinimide (vi) is a compound of formula (vi)

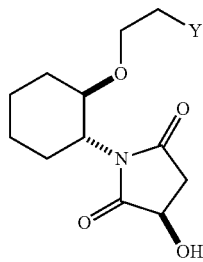

where Y is a phenyl, optionally substituted with one or two substituents selected from halogen or OR, where R is hydrogen, alkyl or aryl ether, alkyl or aryl ester, carbonate, carbamate, sulfonate, phosphate. In an embodiment, Y is selected from 3,4-dimethoxyphenyl, 3,4-dihydroxyphenyl or 3,4-dihalophenyl. In a further embodiment, the hydroxy succinimide is 1-{2-[2-(3,4-Dimethoxy-phenyl)-ethoxy]-cyclohexyl}-3-hydroxy-pyrrolidine-2,5-dione.

As used herein, a 1,4-dielectrophile is a compound of the formula (vii-a,b)

vii-a

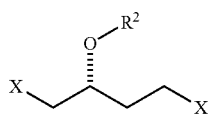

vii-b

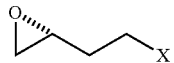

where $R^2$ is selected from hydrogen, esters, carbonates, carbamates, silyl ethers, phosphates or sulfates and X is an activated leaving group including, but not limited to, chloride, bromide, iodide, mesylate, tosylate, triflate and the like. In a further embodiment, a 1,4-dielectrophile is a compound of type vii-a where $R^2$ is hydrogen and X is bromide, mesylate or tosylate. In a further embodiment, a 1,4-dielectrophile is (R)-1,4-dibromo-butan-2-ol.

As used herein, the term "solvent" refers to non-polar, polar aprotic or polar protic solvents. Examples of non-polar solvents include, but are not limited to hexane, heptane, cyclohexane, toluene, trifluorotoluene, chlorobenzene, tert-butyl-methyl ether, tetrahydrofuran, 2-methyl tetrahydrofuran (THF), cyclopentylmethyl ether, dichloromethane and the like. Examples of polar aprotic solvents include, but are not limited to acetonitrile, dimethylformamide, dimethylacetamide, N-methylpyrrolidine, dimethyl sulfoxide. Examples of polar protic solvents include, but are not limited to water, methanol, ethanol, isopropanol, butanol, sec-butanol, trifluoroethanol, methoxy ethanol, ethylene glycol. Examples of a solvent include, but are not limited to, 1) alcohols, 2) amides, 3) aromatic solvents, 4) ethereal compounds and 5) halogenated alkanes. Examples of alcohols include, but are not limited to methanol, ethanol, isopropanol, butanol, trifluoroethanol, methoxy ethanol. Examples of amides include, but are not limited to dimethylformamide, dimethylacetamide, N-methylpyrrolidine. Examples of aromatic solvents include, but are not limited to toluene, trifluorotoluene. Examples of ethereal compounds include, but are not limited to tert-butyl-methyl ether, tetrahydrofuran, 2-methyl tetrahydrofuran, cyclopentylmethyl ether. Examples of halogenated alkanes include, but are not limited to trifluorotoluene, dichloromethane, chlorobenzene.

In an embodiment of the invention, a first solvent may be selected from non-polar and polar aprotic solvents. In a further embodiment, the first solvent is selected from toluene, trifluorotoluene, cyclopentylmethyl ether or 2-methyl-THF.

In an embodiment, a second solvent may be any solvent that is miscible with water. Examples of a second solvent include DMSO, DMAc, DMF, MeCN, THF, alcohols, ethylene glycol, and ethers of ethylene glycol. In a further embodiment, the second solvent is selected from DMSO, alcohols, ethylene glycol or ethers of ethylene glycol.

In an embodiment, a third solvent is any water immiscible solvent or a combination thereof. Examples of a water immiscible solvent include, but are not limited to, MTBE, $PhCH_3$, EtOAc and IPAc and the like. In a further embodiment, the third solvent is a mixture of IPA and MTBE.

In an embodiment, a fourth solvent is selected from polar protic solvents. In an embodiment, the fourth solvent is a polar protic solvent selected water, ethanol, or from the family of isomeric propanols, butanols and pentanols. In a further embodiment, the fourth solvent is selected from water, ethanol, isopropanol and sec-butanol.

In an embodiment, a fifth solvent is selected from polar protic solvents. In an embodiment, the fifth solvent is a polar protic solvent selected water, ethanol, or from the family of isomeric propanols, butanols and pentanols. In a further embodiment, the fifth solvent is selected from water, ethanol, isopropanol and sec-butanol.

In an embodiment, a sixth solvent is selected from apolar protic and aprotic solvents, including aromatics, alkyl nitriles, alkyl acetates, and alcohols. In an embodiment, a sixth solvent is selected from toluene, propionitrile, the family of isomeric butyl acetates, the family of isomeric propyl acetates, or the family of isomeric butanols. In an embodiment, a sixth solvent is selected from n-butyl acetate, isobutyl acetate, and n-propyl acetate. In a further embodiment, the sixth solvent is isobutyl acetate.

As used herein, the phrase "solvent switch" refers to an activity involving switching from one solvent to another by either removing the first solvent by distillation prior to adding the second solvent or by azetropically removing the first solvent in the presence of a second solvent.

As used herein, the term "acid" refers to organic or inorganic acids. The acid may be a Lewis acid or a protic acid. Examples of an organic acid include, but are not limited to, carboxylic acids such as stearic acid, acetic acid, formic acid, propionic acid, butyric acid, oxalic acid, pivalic acid, maleic acid and the like. Examples of inorganic acid include, but are not limited to, hydrochloric acid, sulfuric acid, nitric acid, phosphoric acid, boric acid, and the like. In an embodiment of the instant invention, the acid is selected from hydrochloric acid, sulfuric acid, oxalic acid, pivalic acid or maleic acid. In an embodiment, where hexamethyldisilazane (HMDS) is used to obtain a hydroxy succinimide (vi), a Lewis acid may also be used. In a further embodiment, the Lewis acid is zinc chloride, iron(II) chloride, lithium chloride, copper(II) trifluoromethanesulfonate, iron(III) chloride, iron(II) bromide, zinc bromide, zinc acetate or zinc trifluoromethanesulfonate. Preferably, the Lewis acid used with HMDS is zinc chloride.

As used herein, a metal hydride is any species of the formula $MH_t$ which is capable of donating a hydride, where M is a metal selected from sodium, lithium, magnesium, calcium, titanium, aluminum, boron, or silicon and the integer t is selected from 1 to 4. Examples include metal borohydrides and metal aluminum hydrides. In an embodiment, a metal borohydride is lithium or sodium borohydride.

As used herein, an additive is any species of the formula $BZ_3$ where $Z=C_1-C_6$ alkyl, aryl or alkoxy capable accepting an electron pair. In an embodiment, an additive is a trialkyl or triaryl borate. In a further embodiment, an additive is trimethyl borate.

As used herein, the acid used in conjunction with the additive may be a Lewis acid or protic acid. Examples of a Lewis acid include, but are not limited to $BF_3OEt_2$, $I_2$, $Br_2$.

Examples of a protic acid include, but are not limited to HCl, $H_2SO_4$, methanesulfonic acid or trifluoromethane sulfonic acid. In a further embodiment, a Lewis acid is $BF_3OEt_2$.

As used herein, the term "base" refers to an organic base, an inorganic base, and the like. Examples of a base include, but are not limited to, $K_2CO_3$, $Cs_2CO_3$, $Li_2CO_3$, $Na_2CO_3$, KOH, LiOH, NaOH, CsOH, $K_3PO_4$, KF, $Et_3N$ and other tertiary amines, diisopropylamine and other secondary amines, and butylamine, other primary amines and ammonia. In an embodiment of the instant invention, the base is $K_3PO_4$.

As used herein, a basic buffer is described as an aqueous solution of a weak base and its conjugate acid with a pH greater than 7 which reduces the change of pH upon addition of small amounts of acid or base, or upon dilution. Examples of a basic buffer include but are not limited to aqueous solutions of sodium or potassium bicarbonate, sodium or potassium acetate, sodium or potassium citrate or sodium or potassium phosphate, sodium or potassium tetraborate or organic amines. Examples of organic amines include, but are not limited to methylamine, isopropylamine, dimethylamine, triethylamine, diisopropylamine, pyridine, 2,6-lutidene, tetramethylguanidine, 1,8-diazabicyclo[5.4.0]undec-7-ene. In an embodiment of the invention, the basic buffer is selected from sodium tetraborate or ethanolamine.

As used herein, an amine, or primary amine, can be described as $R^*NH_2$ where "$R^*$" is selected from $C_1-C_6$ alkyl, $C_1-C_6$ alkoxy, $C_1-C_6$ acyl, $C_1-C_6$ carbamoyl, an alkylaryl group, or aryl group which is unsubstituted or substituted with one or more enzymatically non-inhibiting groups. In addition, "amino donor" or "amine donor" refers to an amino compound which donates an amino group to the amino acceptor, thereby becoming a carbonyl species. An "amino donor", "amine donor" and "amine" are used interchangeably. Amino donors are molecules of general formula shown below,

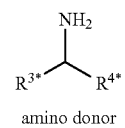

amino donor in which each of $R^{3*}$, $R^{4*}$, when taken independently, is an alkyl, an alkylaryl group, or aryl group which is unsubstituted or substituted with one or more enzymatically non-inhibiting groups. $R^{3*}$ can be the same or different from $R^4$ in structure or chirality. In some embodiments, $R^{3*}$ and $R^{4*}$, taken together, may form a ring that is unsubstituted, substituted, or fused to other rings. Typical amino donors that can be used with the embodiments of the present disclosure include chiral and achiral amino acids, and chiral and achiral amines.

Examples of amines, or amino donors, include, but are limited to isopropylamine (also referred to as 2-aminopropane, and referred to elsewhere herein as "IPM"), α-phenethylamine (also termed 1-phenylethanamine), and its enantiomers (S)-1-phenylethanamine and (R)-1-phenylethanamine, 2-amino-4-phenylbutane, glycine, L-glutamic acid, L-glutamate, monosodium glutamate, L-alanine, D-alanine, D,L-alanine, L-aspartic acid, L-lysine, D,L-ornithine, β-alanine, taurine, n-octylamine, cyclohexylamine, 1,4-butanediamine (also referred to as putrescine), 1,6-hexanediamine, 6-aminohexanoic acid, 4-aminobutyric acid, tyramine, and benzyl amine, 2-aminobutane, 2-amino-1-butanol, 1-amino-1-phenylethane, 1-amino-1-(2-methoxy-5-fluorophenyl)ethane, 1-amino-1-phenylpropane, hydroxyphenyl)propane, 1-amino-1-(4-bromophenyl)propane, nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, 3-methylcyclohexylamine, 1-aminotetralin, 2-aminotetralin, 2-amino-5-methoxytetralin, and 1-aminoindan, including both (R) and (5) single isomers where possible and including all possible salts of the amines. In an embodiment of the instant invention, an amine is selected from methylamine, ethylamine, isopropylamine and 2-aminoethanol. In an embodiment, the amine is isopropylamine.

"Chiral amine" refers to amines of general formula $R^{1*}-CH(NH_2)-R^{2*}$ and is employed herein in its broadest sense, including a wide variety of aliphatic and alicyclic compounds of different, and mixed, functional types, characterized by the presence of a primary amino group bound to a secondary carbon atom which, in addition to a hydrogen atom, carries either (i) a divalent group forming a chiral cyclic structure, or (ii) two substituents (other than hydrogen) differing from each other in structure or chirality. Divalent groups forming a chiral cyclic structure include, for example, 2-methylbutane-1,4-diyl, pentane-1,4-diyl,hexane-1,4-diyl, hexane-1,5-diyl, 2-methylpentane-1,5-diyl. The two different substituents on the secondary carbon atom ($R^{1*}$ and $R^{2*}$ above) also can vary widely and include alkyl, aralkyl, aryl, halo, hydroxy, lower alkyl, lower alkoxy, lower alkylthio, cycloalkyl, carboxy, carbalkoxy, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc., as well as alkyl, aralkyl, or aryl substituted by the foregoing.

As used herein, a secondary amine can be described as $R^3R^4NH$, where $R^3$ and $R^4$ are each independently selected from $C_1$-$C_6$ alkyl, $C_1$-$C_6$ alkoxy $C_1$-$C_6$ acyl, $C_1$-$C_6$ carbamoyl, or aryl, and where $R^3$ and $R^4$ can form a ring. Examples include but are not limited to, dimethyl amine, diethyl amine, pyrrolidine, morpholine, N-methyl benzyl amine, and N-methyl aniline. In an embodiment, the secondary amine is pyrrolidine. The process of the instant invention can also use a chiral secondary amine, such as 2-(S)-methoxymethylpyrrolidine, L-proline methyl ester, 2-(R)-diphenylmethylpyrrolidine, 2-(R)-(1',1'-diphenylhydroxylmethyl)pyrrolidine and the like. In an embodiment, the secondary amine is 2-(S)-methoxymethylpyrroldine. Using a chiral amine can afford a non-racemic alkoxy ketone (iii).

As used herein, a basic aqueous solution refers to an aqueous solution with a pH greater than 7. Examples of a basic aqueous solution include, but are not limited to, aqueous solutions of sodium or potassium bicarbonate, sodium or potassium acetate, sodium or potassium citrate or sodium or potassium phosphate, sodium or potassium tetraborate or organic amines. In an embodiment, a basic aqueous solution is selected from a solution of potassium phosphate or carbonate.

As used herein, an acidic aqueous solution refers to an aqueous solution with a pH less than 7. Examples of an acidic aqueous solution include, but are not limited to, aqueous solutions of hydrochloric acid, hydrobromic acid, sulfuric acid, acetic acid, glycolic acid, citric acid and the like.

As used herein, an acid activator is any electrophilic activating agent selected from, but not limited to, acyl halides, acid anhydrides, phosphonic anhydrides, phosphorous halides, carbodiomides, phosphorous oxy-halides, sulfonyl halides, boron halides, alkyl boronic acids or boronic acids. In an embodiment, the acid activator is an alkyl boronic acid, acetyl chloride, propionyl chloride, pivaloyl chloride, thionyl chloride or trifluoroacetic anhydride. In another embodiment, an acid activator is acetyl chloride, alkyl boronic acid or thionyl chloride. In a further embodiment, an acid activator is an alkyl boronic acid selected from methyl boronic acid or butyl boronic acid.

As used herein, the phrase "isolating the compound" or "reducing" refers to techniques known in the art by which one may obtain the final compound. Examples of such techniques include, but are not limited to, crystallization, filtration, distillation and the like. In one embodiment of the instant invention, the compound is isolated via crystallization.

As used herein, the phrase "biphasic mixture" refers to a mixture having an aqueous phase and an organic phase.

In the instant invention, unless otherwise defined, the terms "first", "second", "third", "fourth", etc. are utilized to demonstrate that an element of the process may be added more than once during the process. The first and second element (e.g. "first solvent" and "second solvent") may be different or the same. The terms are used to indicate that the element is being added a second time during the described step of the instant invention.

A "cofactor," as used herein, refers to a non-protein compound that operates in combination with an enzyme in catalyzing a reaction. Examples of a cofactor include, but are not limited to "Pyridoxal-5'-phosphate" or "PLP". "Pyridoxalphosphate," "PLP," "pyridoxal-5'-phosphate," "PYP," and "P5P" are used interchangeably herein to refer to the compound that acts as a cofactor in transaminase reactions. In some embodiments, pyridoxal phosphate is defined by the structure 1-(4'-formyl-3'-hydroxy-2'-methyl-5'-pyridyl) methoxyphosphonie acid, CAS number [54-47-7], Pyridoxal-5'-phosphate can be produced in vivo by phosphorylation and oxidation of pyridoxol (also known as Vitamin $B_6$). In transamination reactions using transaminase enzymes or polypeptides, the amine group of the amino donor is transferred to the cofactor to produce a keto byproduct, while pyridoxal-5'-phosphate is converted to pyridoxamine phosphate. Pyridoxal-5'-phosphate is regenerated by reaction with a different keto compound (the amino acceptor). The transfer of the amine group from pyridoxamine phosphate to the amino acceptor produces a chiral amine and regenerates the cofactor. In some embodiments, the pyridoxal-5'-phosphate can be replaced by other members of the vitamin $B_6$ family, including pyridoxine (PN), pyridoxal (PL), pyridoxamine (PM), and their phosphorylated counterparts; pyridoxine phosphate (PNP), and pyridoxamine phosphate (PMP). In an embodiment, the co-factor is selected from pyridoxal-5'-phosphate (PLP), pyridoxine (PN), pyridoxal (PL), pyridoxamine (PM), and their phosphorylated counterparts; pyridoxine phosphate (PNP), and pyridoxamine phosphate (PMP). In an embodiment, the co-factor is Pyridoxal-5'-phosphate (PLP).

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Aminotransferase" and "transaminase" are used interchangeably herein to refer to a polypeptide having an enzymatic capability of transferring an amino group ($NH_2$), a pair of electrons, and a proton from a primary amine to a carbonyl group (C=O) of an acceptor molecule. Transaminases as used herein include naturally occurring (wild type) transaminase as well as non-naturally occurring engineered polypeptides generated by human manipulation. As used herein, "transaminase polypeptide" and "transaminase enzyme" are used interchangeably. In an embodiment of the instant process, a transaminase polypeptide having amino acid sequence listing SEQ ID NO: 18 or SEQ ID NO: 206 is used. In an embodiment of the instant process, a transaminase polypeptide having polynucleotide sequence SEQ ID NO: 17 or SEQ ID NO: 205 is used.

The abbreviations used for the genetically encoded amino acids are conventional and are as follows:

| Amino Acid | Three-Letter Abbreviation | One-Letter Abbreviation |
|---|---|---|
| Alanine | Ala | A |
| Arginine | Arg | R |
| Asparagine | Asn | N |

| Amino Acid | Three-Letter Abbreviation | One-Letter Abbreviation |
|---|---|---|
| Aspartate | Asp | D |
| Cysteine | Cys | C |
| Glutamate | Glu | E |
| Glutamine | Gln | Q |
| Glycine | Gly | G |
| Histidine | HIS | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an "L" or a "D" or clear from the context in which the abbreviation is used, the amino acid may be in either the L- or D-configuration about α-carbon ($C_\alpha$). For example, whereas "Ala" designates alanine without specifying the configuration about the α-carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When polypeptide sequences are presented as a string of one-letter or three-letter abbreviations (or mixtures thereof), the sequences are presented in the amino (N) to carboxy (C) direction in accordance with common convention.

The abbreviations used for the genetically encoding nucleosides are conventional and are as follows: adenosine (A); guanosine (G); cytidine (C); thymidine (T); and uridine (U). Unless specifically delineated, the abbreviated nucleotides may be either ribonucleosides or 2'-deoxyribonucleosides. The nucleosides may be specified as being either ribonucleosides or 2'-deoxyribonucleosides on an individual basis or on an aggregate basis. When nucleic acid sequences are presented as a string of one-letter abbreviations, the sequences are presented in the 5' to 3' direction in accordance with common convention, and the phosphates are not indicated. In addition, the following terms are defined as:

"Amino acceptor" and "amine acceptor," "keto substrate," "keto," and "ketone" are used interchangeably herein to refer to a carbonyl (keto, or ketone) compound which accepts an amino group from a donor amine. Amino acceptors are molecules of general formula shown below,

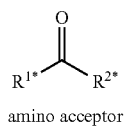

amino acceptor in which each of $R^{1*}$, $R^{2*}$, when taken independently, is an alkyl, an alkylaryl group, or aryl group which is unsubstituted or substituted with one or more enzymatically acceptable groups. $R^{1*}$ may be the same or different from $R^{2*}$ in structure or chirality. In some embodiments, $R^{1*}$ and $R^{2*}$, taken together, may form a ring that is unsubstituted, substituted, or fused to other rings. Amino acceptors include keto carboxylic acids and alkanones (ketones). Typical keto carboxylic acids are α-keto carboxylic acids such as glyoxalic acid, pyruvic acid, oxaloacetic acid, and the like, as well as salts of these acids. Amino acceptors also include substances which are converted to an amino acceptor by other enzymes or whole cell processes, such as fumaric acid (which can be converted to oxaloacetic acid), glucose (which can be converted to pyruvate), lactate, maleic acid, and others. Amino acceptors that can be used include, by way of example and not limitation, (R)-2-(3,4-dimethoxyphenethoxy)cyclohexanone, 3,4-dihydronaphthalen-1(2H)-one, 1-phenylbutan-2-one, 3,3-dimethylbutan-2-one, octan-2-one, ethyl 3-oxobutanoate, 4-phenylbutan-2-one, 1-(4-bromophenyl)ethanone, 2-methyl-cyclohexamone, 7-methoxy-2-tetralone, 1-hydroxybutan-2-one, pyruvic acid, acetophenone, (R)-2-(3,4-dimethoxyphenethoxy)cyclohexanone, 2-methoxy-5-fluoroacetophenone, levulinic acid, 1-phenylpropan-1-one, 1-(4-bromophenyl)propan-1-one, 1-(4-nitrophenyl)propan-1-one, 1-phenylpropan-2-one, 2-oxo-3-methylbutanoic acid, 1-(3-trifluoromethylphenyl)propan-1-one,hydroxypropanone, methoxyoxypropanone, 1-phenylbutan-1-one, 1-(2,5-dimethoxy-4-methylphenyl)butan-2-one, 1-(4-hydroxyphenyl)butan-3-one, 2-acetylnaphthalene, phenylpyruvic acid, 2-ketoglutaric acid, and 2-ketosuccinic acid, including both (R) and (S) single isomers where possible.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" or "engineered" or "non-naturally occurring" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. A "reference sequence" can be based on a primary amino acid sequence, where the reference sequence is a sequence that can have one or more changes in the primary sequence. For instance, a "reference sequence based on SEQ ID NO:2 having at the residue corresponding to X9 a threonine" refers to a reference sequence in which the corresponding residue at X9 in SEQ ID NO:2, which is a alanine, has been changed to threonine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered transaminase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" or "residue difference" refers to a change in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X3 as compared to SEQ ID NO: 2" refers to a change of the amino acid residue at the polypeptide position corresponding to position 3 of SEQ ID NO:2. Thus, if the reference polypeptide of SEQ ID NO: 2 has a glutamine at position 3, then a "residue difference at position X3 as compared to SEQ ID NO:2" an amino acid substitution of any residue other than glutamine at the position of the polypeptide corresponding to position 3 of SEQ ID NO: 2. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances (e.g., in Tables 2A, 2B, 2C and 2D), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide can include one or more amino acid residue differences relative to a reference sequence, which is indicated by a list of the specified positions where changes are made relative to the reference sequence. The present process may use engineered polypeptide sequences which comprise one or more amino acid differences that include either/or both conservative and non-conservative amino acid substitutions.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acids having aromatic side chains is substituted with another amino acid having an aromatic side chain, e.g., phenylalanine, tyrosine, tryptophan, and histidine; an amino acid with a basic side chain is substituted with another amino acid with a basis side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Exemplary conservative substitutions are provided in Table 1 below:

TABLE 1

| Residue | Possible Conservative Substitutions |
|---|---|
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | None |

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered transaminase enzyme or polypeptide. Deletions can be directed to the internal portions and/or terminal portions of the polypeptide. The deletion can comprise a continuous segment or can be discontinuous.

"Insertion" refers to modification to the polypeptide by addition of one or more amino acids from the reference polypeptide. The improved engineered transaminase enzymes comprise insertions of one or more amino acids to the naturally occurring transaminase polypeptide as well as insertions of one or more amino acids to other improved transaminase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length transaminase polypeptide, for example the polypeptide of SEQ ID NO:2 or engineered transaminase of SEQ ID NO:34.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Where a mixture contains more than two diastereomers it is common to report the ratio of diastereomers or "diastereomeric ratio" rather than diastereomeric excess. Enantiomeric excess and diastereomeric excess are types of stereomeric excess. "Highly stereoselective" refers to a transaminase polypeptide that is capable of converting the substrate to the corresponding chiral amine product with at least about 85% stereomeric excess.

"Improved enzyme property" refers to a transaminase polypeptide that exhibits an improvement in any enzyme property as compared to a reference transaminase. For the engineered transaminase polypeptides, the comparison is generally made to the wild-type transaminase enzyme, although in some embodiments, the reference transaminase can be another improved engineered transaminase. Enzyme properties for which improvement is desirable include, but are not limited to, enzymatic activity (which can be expressed in terms of percent conversion of the substrate), thermo stability, solvent stability, pH activity profile, cofactor requirements, refractoriness to inhibitors (e.g., substrate or product inhibition), stereospecificity, and stereoselectivity (including enantioselectivity).

"Increased enzymatic activity" refers to an improved property of the engineered transaminase polypeptides, which can be represented by an increase in specific activity (e.g., product produced/time/weight protein) or an increase in percent conversion of the substrate to the product (e.g., percent conversion of starting amount of substrate to product in a specified time period using a specified amount of transaminase) as compared to the reference transaminase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.1 times the enzymatic activity of the corresponding wild-type transaminase enzyme, to as much as 2 times, 5 times, 10 times, 20 times, 25 times, 50 times, 75 times, 100 times, or more enzymatic activity than the naturally occurring transaminase or another engineered transaminase from which the transaminase polypeptides were derived. In specific embodiments, the engineered transaminase enzyme exhibits improved enzymatic activity in the range of 1.5 to 50 times, 1.5 to 100 times greater than that of the parent transaminase enzyme. It is understood by the skilled artisan that the activity of any enzyme is diffusion limited such that the catalytic turnover rate cannot exceed the diffusion rate of the substrate, including any required cofactors. The theoretical maximum of the diffusion limit, or $k_{cat}/K_m$, is generally about $10^8$ to $10^9$ $(M^{-1} s^{-1})$. Hence, any improvements in the enzyme activity of the transaminase will have an upper limit related to the diffusion rate of the substrates acted on by the transaminase enzyme. Transaminase activity can be measured by any one of standard assays, such as by monitoring changes in spectrophotometric properties of reactants or products. The amount of products produced can be measured by High-Performance Liquid Chromatography (HPLC) separation combined with UV absorbance or fluorescent detection following o-phthaldialdehyde (OPA) derivatization. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic conversion of the substrate(s) to the corresponding product(s). "Percent conversion" refers to the percent of the substrate that is converted to the product within a period of time under specified conditions. Thus, the "enzymatic activity" or "activity" of a transaminase polypeptide can be expressed as "percent conversion" of the substrate to the product.

"Thermostable" refers to a transaminase polypeptide that maintains similar activity (more than 60% to 80% for example) after exposure to elevated temperatures (e.g., 40-80° C.) for a period of time (e.g., 0.5-24 hrs) compared to the wild-type enzyme.

"Solvent stable" refers to a transaminase polypeptide that maintains similar activity (more than e.g., 60% to 80%) after exposure to varying concentrations (e.g., 5-99%) of solvent (ethanol, isopropyl alcohol, dimethylsulfoxide (DMSO), tetrahydrofuran, 2-methyltetrahydrofuran, acetone, toluene, butyl acetate, methyl tert-butyl ether, etc.) for a period of time (e.g., 0.5-24 hrs) compared to the wild-type enzyme.

"Thermo- and solvent stable" refers to a transaminase polypeptide that is both thermostable and solvent stable.

"Derived from" as used herein in the context of engineered transaminase enzymes, identifies the originating transaminase enzyme, and/or the gene encoding such transaminase enzyme, upon which the engineering was based. For example, the engineered transaminase enzyme of SEQ ID NO:34 was obtained by artificially evolving, over multiple generations the gene encoding the *Arthrobacter* sp. KNK168 transaminase enzyme of SEQ ID NO:2. Thus, this engineered transaminase enzyme is "derived from" the wild-type transaminase of SEQ ID NO:2.

"Control sequence" is defined herein to include all components, which are necessary or advantageous for the expression of a polynucleotide and/or polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

The term "patient" includes mammals, especially humans, who use the instant active agent for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk for diseases and medical conditions affected by inhibition of cholesterol absorption.

The term "therapeutically effective amount" is intended to mean that amount of a pharmaceutical drug that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. Particularly, the dosage a patient receives can be selected so as to achieve the amount of LDL cholesterol lowering desired; the dosage a patient receives may also be titrated over time in order to reach a target LDL level. The dosage regimen utilizing the compound of the instant invention is selected in accordance with a variety of factors including type, species, age, weight, sex and medical condition of the patient; the severity of the condition to be treated; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition.

"Modulating" in connection with the activity of an ion channel means that the activity of the ion channel may be either increased or decreased in response to administration of a compound or composition or method of the present invention. Thus, the ion channel may be activated, so as to transport more ions, or may be blocked (inhibited), so that fewer or no ions are transported by the channel.

"Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. rd. at 1449. In addition, antioxidants and suspending agents may be used.

"Pharmaceutically acceptable salt" refers to salts of the compounds of the present invention derived from the combination of such compounds and an organic or inorganic acid (acid addition salts) or an organic or inorganic base (base addition salts). Examples of pharmaceutically acceptable salt include but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002. The compounds of the present invention may be used in either the free base or salt forms, with both forms being considered as being within the scope of the present invention.

Compound A may be administered to prevent or reduce the risk of occurrence, or recurrence where the potential exists, of a coronary heart disease event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

The aminocyclohexyl ether compounds of the present invention may be in the form of a solvate in a pharmaceutically acceptable solvent such as water or physiological saline. Alternatively, the compounds may be in the form of the free base or in the form of a pharmaceutically acceptable salt such as the hydrochloride, sulfate, phosphate, citrate, fumarate, methanesulfonate, acetate, tartrate, maleate, lactate, mandelate, salicylate, succinate and other salts known in the art. The appropriate salt would be chosen to enhance bioavailability or stability of the compound for the appropriate mode of employment (e.g., oral or parenteral routes of administration).

As used herein, "treating arrhythmia" refers to therapy for arrhythmia. An effective amount of a composition of the present invention is used to treat arrhythmia in a warm-blooded animal, such as a human. Methods of administering effective amounts of antiarrhythmic agents are well known in the art and include the administration of an oral or parenteral dosage form. Such dosage forms include, but are not limited to, parenteral dosage form. Such dosage forms include, but are not limited to, parenteral solutions, tablets, capsules, sustained release implants, and trans dermal delivery systems. Generally, oral or intravenous administration is preferred for some treatments. The dosage amount and frequency are selected to create an effective level of the agent without harmful effects. It will generally range from a dosage of from about 0.01 to about 100 mg/kg/day, and typically from about 0.1 to 10 mg/kg where administered orally or intravenously for antiarrhythmic effect or other therapeutic application.

A variety of chromatographic techniques may be employed in the preparation of Form I. These techniques include, but are not limited to: High Performance Liquid Chromatography (HPLC) including normal-reversed- and chiral-phase; Medium Pressure Liquid Chromatography (MPLC), Super Critical Fluid Chromatography; preparative Thin Layer Chromatography (prep TLC); Gas Chromatography (GC); flash chromatography with silica gel or reversed-phase silica gel; ion-exchange chromatography; and radial chromatography. All temperatures are degrees Celsius unless otherwise noted. Degrees Celsius may be noted in the examples as "C" without the degree symbol (e.g. 50 C) or "° C." with a degree symbol (e.g. 50° C.).

Transaminase Polypeptide

The transaminase polypeptide useful in the process of the present invention exhibits high stereoselectivity for the R-amine products of compound (2a) and compound (2e) relative to the corresponding S-amine products of compound (2d) and compound (2b), respectively, converting a racemic mixture of compound (1) to the R-amine products in an enantiomeric excess of at least 85% e.e., 90% e.e., 95% e.e., 98% e.e., 99% e.e., or more (see SCHEME A below).

SCHEME A

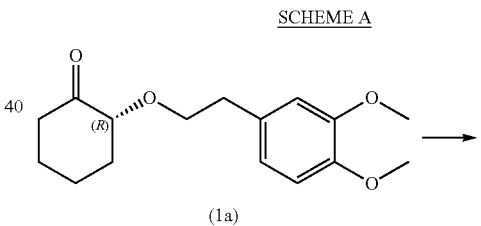

(1a)

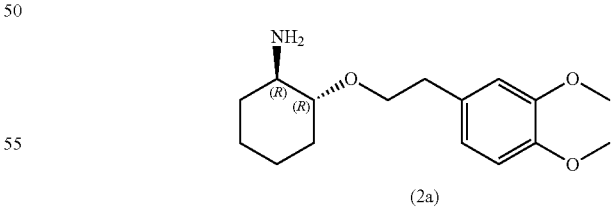

(2a)

Additionally, the engineered transaminase polypeptides exhibit diastereoselectivity for the trans R-amine product and are capable of converting a racemic mixture of compound (1) to the (1R, 2R)-trans amine product of compound (2a) in at least a 2:1 diastereomeric ratio relative to the (1R, 2S)-cis amine product of compound (2c) under suitable reaction conditions (see SCHEME B below).

SCHEME B
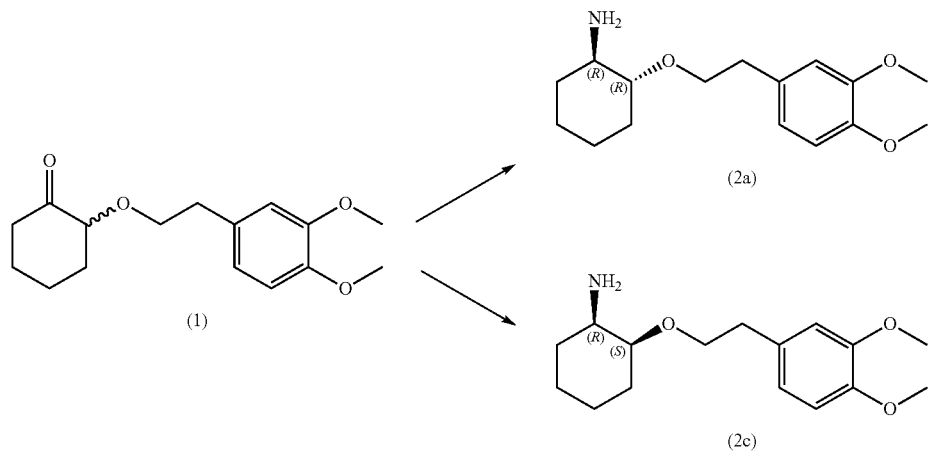
SCHEME C
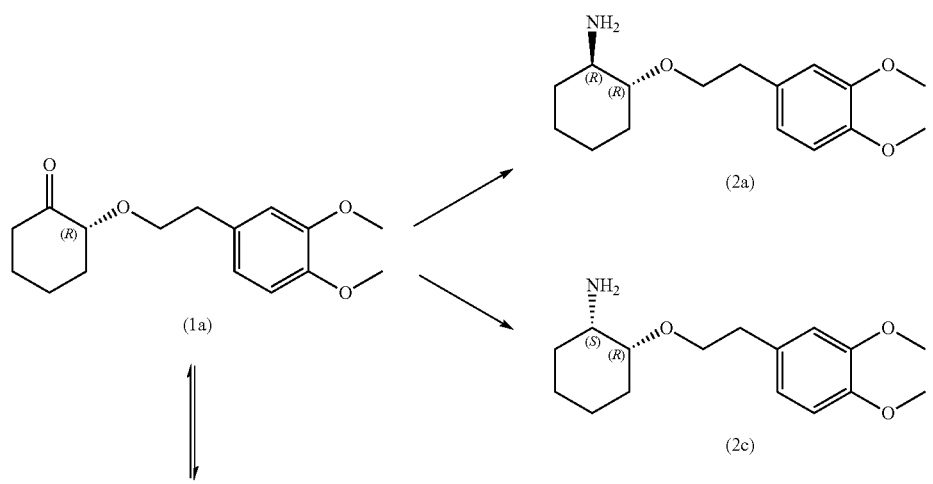
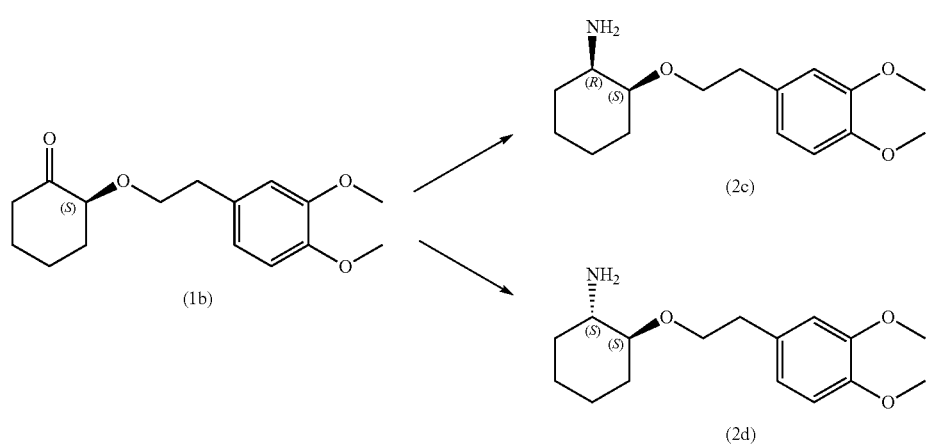

The transaminases are engineered with improved properties, such as increased stereoselectivity, as compared to the wild-type *Arthrobacter* sp. KNK168 polypeptide of SEQ ID NO:2, or the engineered polypeptide of SEQ ID NO:4, which has a single amino acid difference (I306V) relative to the wild-type. These engineered transaminase polypeptides are adapted for efficient conversion of compound (1) to the product of compound (2a) and have one or more residue differences as compared to the reference engineered transaminase polypeptide of SEQ ID NO: 6 (which has 24 amino acid differences relative to the wild-type). These residue differences are associated with improvements in enzyme properties, particularly increased stereoselectivity, increased activity, increased thermostability, and tolerance of increased substrate and/or product concentration (e.g., decreased product inhibition).

The engineered polypeptides described have both high enantioselectivity for R-amine products and high diastereoselectivity for the trans relative to the cis amine products. In some embodiments the transaminase polypeptides are capable of converting the substrate of compound (1a) to compound (2a) in the presence of a substrate concentration of at least about 20 g/L, about 30 g/L, about 40 g/L, about 50 g/L, about 70 g/L, about 100 g/L, with a percent conversion of at least about 40%, at least about 50%, at least about 60%, at least about 70%, at least about 80%, or at least about 90%, at least about 95%, at least about 98%, at least about 99%, in a reaction time of about 48 h, about 36 h, about 24 h, or even shorter length of time, under suitable reaction conditions. Diastereomeric ratio [(2a)]:[(2c)]≥2:1

The engineered transaminase polypeptides are capable of converting a racemic mixture of compound (1) to the R-amine products of compound (2a) and compound (2c) in at least 98% e.e. relative to the corresponding S-amine products of compound (2d) and (2b), respectively, and producing compound (2a) in at least a 2:1 diastereomeric ratio relative to compound (2c) are synthetic variants of a naturally occurring transaminase of *Arthrobacter* sp. KNK168 (polypeptide of SEQ ID NO: 2), and comprise amino acid sequences that have one or more residue differences as compared to the wild-type sequence or a reference sequence of SEQ ID NO:6. The residue differences occur at residue positions that affect functional properties of the enzyme including stereoselectivity, substrate and/or product binding (e.g., resistance to substrate and/or product inhibition), activity (e.g., percent conversion of substrate to product), thermostability, solvent stability, expression, or various combinations thereof.

In an embodiment of the instant process, transaminase polypeptides comprise amino acid sequences having at least 80% sequence identity to the reference polypeptide of SEQ ID NO: 6 and having amino acid residue differences as compared to SEQ ID NO: 6 at one or more of the following positions X2; X4; X5; X7; X8; X9; X10; X11; X14; X22; X28; X37; X38; X41; X42; X44; X52; X54; X55; X56; X58; X69; X94; X99; X108; X124; X126; X135; X136; X141; X142; X150; X155; X156; X157; X164; X165; X171; X182; X199; X209; X210; X213; X215; X217; X218; X223; X245; X257; X265; X267; X296; and X328. In some embodiments of the process, the amino acid residue differences of the transaminase polypeptide as compared to SEQ ID NO: 6 are selected from the following: X2K; X2Q; X2S; X4I; X4L; X5H; X5I; X5L; X5N; X5S; X5T; X5V; X7A; X8T; X9N; X9Q; X9S; X10V; X11K; X14R; X22I; X28P; X37R; X38G; X41F; X42A; X44Q; X44V; X52K; X54K; X54N; X54P; X54R; X55L; X56G; X56L; X56S; X58L; X69C; X69V; X69W; X94L; X99L; X108V; X124F; X124I; X124L; X124R; X124V; X126A; X126T; X135Q; X136W; X141L; X142R; X142T; X150A; X150F; X150N; X155A; X156A; X156F; X156G; X156S; X156T; X157L; X164A; X165N; X171A; X182T; X199F; X199R; X199Y; X209C; X209D; X209E; X210S; X213P; X215F; X215Y; X217S; X218M; X223I; X223L; X223M; X223N; X245S; X257F; X265T; X267V; X296S; and X328I.

In some embodiments of the instant process, the transaminase polypeptide amino acid sequences comprise one or more combinations of amino acid differences as compared to SEQ ID NO: 6 selected from the following: (a) X124V, and X210S; (b) X124V, X136W, and X210S; (c) X69V, and X136W; (d) X69V, and X215Y; (e) X69V, and X217S; (f) X69V, X124I, and X136W; (g) X69V; X136W, and X257F; (h) X44V, and X223N; (i) X56S, X69V, X136W, and X265T; and (j) X28P, X69V, and X136W.

Various other combinations of the disclosed amino acid differences can be combined in the engineered polypeptides as disclosed herein and provide various improved enzyme properties. Exemplary engineered polypeptides having various combinations of amino acid differences resulting in improved properties are disclosed in Tables 2A, 2B, 2C and 2D and Example A. The amino acid sequences are provided in the sequence listing incorporated by reference herein and include SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206.

Polynucleotides encoding the engineered transaminase polypeptides capable of converting a racemic mixture of compound (1) to compound (2a) have at least a 2:1 diastereomeric ratio relative to compound (2c). Exemplary polynucleotide sequences are provided in the sequence listing incorporated by reference herein and include SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, and 205.

Any of the transaminase polypeptides can be used in improved processes for the preparation of compound (2a) due to their improved enzymatic properties including, production of high enantiomeric excess of R-amine products (e.g., at least about 98% e.e.), high diastereomeric ratio of the trans R-amine product of compound (2a) (e.g., at least about 1.2 d.r.), increased activity (e.g., at least about 2-fold increased activity relative to SEQ ID NO:2), high percent conversion (e.g., at least about 90% conversion in 24 h), in the presence of high substrate loadings (e.g., at least about 40 g/L a racemic mixture of compound (1)), and using isopropylamine as the amino donor. Suitable reactions conditions for the conversion of compound (1a) to compound (2a), or its salts, hydrates, or solvates, using the transaminase polypeptides of the present process are described in greater detail below, including but not limited to ranges of pH, temperature, buffer, solvent system, substrate loading, mixture of substrate enantiomers racemic mixture of compound (1)), polypeptide loading, amino donor loading, atmosphere, and reaction time.

An analog of compound (2a) can be prepared in enantiomeric and diastereomeric excess from an analog of compound (1a) using engineered transaminase polypeptides in the above described process. Accordingly, in some embodiments of the instant process, the conversion of an analog of compound (1a) to an analog of compound (2a) can be carried out wherein the analog of compound (1a) is a compound of Formula I*

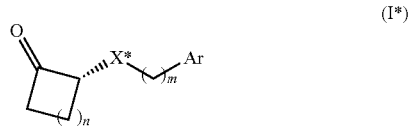

wherein, Ar is an optionally substituted aromatic ring selected from phenyl, fused phenyl, heteroaryl, or fused heteroaryl; X* is selected from N, O, $CH_2$, and S; m=1 to 6; n=1 to 6; and the analog of compound (2a) prepared is a compound of Formula II*

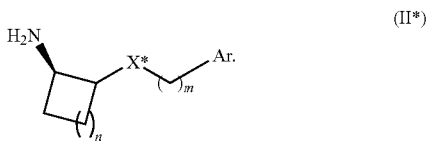

Additionally, the methods using the engineered transaminase polypeptides of the present disclosure to convert compound (1a) to compound (2a) can be used as a step in a process for the preparation of the pharmaceutical ingredient of Compound A, (IUPAC name: (3R)-1-[(1R,2R)-2-[2-(3,4-dimethoxyphenyl)ethoxy]cyclohexyl]pyrrolidin-3-ol), or its salts, hydrates, or solvates,

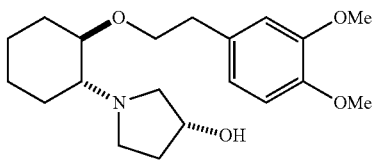

wherein, the step in the process comprises contacting compound (1a) with an engineered transaminase polypeptide of the present disclosure in the presence of an amino donor under reaction conditions suitable for conversion of compound (1a) to compound (2a) in enantiomeric and diastereomeric excess.

In some embodiments, the conversion of an analog of compound (1a) to an analog of compound (2a) can be carried out wherein Ar is phenyl, optionally substituted with one or two substituents selected from halogen or OR, where R is H, alkyl or aryl ether, alkyl or aryl ester, carbonate, sulfonate, or phosphate.

In some embodiments, the conversion of an analog of compound (1a) to an analog of compound (2a) can be carried out wherein Ar is selected from 3,4-dimethoxyphenyl, 3,4-dihydroxyphenyl, or 3,4-dihalophenyl.

In some embodiments, the conversion of an analog of compound (1a) to an analog of compound (2a) can be carried out wherein X is O; m=1 or 2; and n=2 or 3.

In some embodiments, the conversion of an analog of compound (1a) to an analog of compound (2a) can be carried out wherein Ar is phenyl, optionally substituted with one or two substituents selected from halogen or OR, where R is H, alkyl or aryl ether, alkyl or aryl ester, carbonate, sulfonate, or phosphate; X is O; m=1 or 2; and n=2 or 3.

In some embodiments, the conversion of an analog of compound (1a) to an analog of compound (2a) can be carried out wherein Ar is selected from 3,4-dimethoxyphenyl, 3,4-dihydroxyphenyl, or 3,4-dihalophenyl; X is N, O, or S; m=1 or 2; and n=2 or 3. In some embodiments, one or more of the hydroxy groups on the aryl group are protected with a hydroxyl protecting group selected from the group consisting of acetyl, benzyl, benzoyl, methyl, methoxy, tert-butyloxycarbonyl, para-methoxybenzyl, benzylidine, dimethylacetal, silyl, tert-butyl-diphenylsilyl, and trimethylsilyl. Other examples of hydroxyl protecting groups that may be the R group of compounds of Formula II* undergoing the biocatalytic methods of the present disclosure can be found in P. G. M. Wuts and T. W. Greene, "Greene's Protective Groups in Organic Synthesis—Fourth Edition," John Wiley and Sons, New York, N.Y., 2007, Chapter 7 ("Greene").

In some embodiments, the conversion of an analog of compound (1a) to an analog of compound (2a) can be carried out wherein the analog of compound (1a) is a deuterated version of the compound (1a) (i.e., a molecule have the same structure as compound (1a) but with one or more the hydrogen atoms of compound (1a) substituted with a deuterium atom). Similarly, the methods for the conversion of an analog of compound (1a) to an analog of compound (2a) can be carried out with the deuterated version of any of the above described analog compounds of Formula I*.

The suitable reaction conditions under which the above-described improved properties of the engineered polypeptides can be determined can comprise concentrations or amounts of polypeptide, substrate, amine donor, cofactor, buffer, co-solvent, pH, and/or conditions including temperature and reaction time. In some embodiments, the suitable reaction conditions comprise 200 μL total volume, 5 g/L of the racemic mixture of compound (1), 100 μL cell lysate comprising the polypeptide, 1 M isopropylamine (IPM), 1 mM PLP, 100 mM TEA, pH 10.0, 45° C. and 2 h reaction time. In some embodiments, the suitable reaction conditions comprise 10 g/L substrate of the racemic mixture of compound (1), 1 g/L SFP powder of the polypeptide, 1.5 M isopropylamine, 1 g/L PLP, 0.2 M borate buffer, 20% (v/v) DMSO, pH 10.5, 45° C. and 20-24 h reaction time.

Structure and function information for exemplary non-naturally occurring (or engineered) transaminase polypeptides useful in the process of the present disclosure are shown below in Tables 2A, 2B, 2C and 2D. The odd numbered sequence identifiers (i.e., SEQ ID NO) refer to the nucleotide sequence encoding the amino acid sequence provided by the even numbered SEQ ID NOs, and the sequences are provided in the electronic sequence listing file accompanying this disclosure, which is hereby incorporated by reference herein. The amino acid residue differences are based on comparison to the reference polypeptide sequence of SEQ ID NO: 6, which is an engineered transaminase polypeptide having the following 24 amino acid differences relative to the naturally occurring transaminase of Arthrobacter sp. KNK168 (SEQ ID NO: 2): S8P; Y60F; L61Y; H62T; V65A; V69T; D81O; M94I; I96L; F122I; G136F; A169L; V199I; A209L; G215C; G217N; S223P; L269P; L273Y; T282S; A284O; P297S; I306V; and S321P.

The "trans:cis diastereomeric ratio" referenced in Tables 2A 2B and 2D (also referred to herein as "d.r.") refers to the ratio of the two possible trans diastereomer products (e.g., compound (2a) and compound (2d)) to the two possible cis diastereomer products (e.g., compound (2b) and compound (2c)). The trans: cis ratio can be calculated from the formula,

[(2a)+(2d)]/[(2b)+(2c)]. However, the engineered transaminase polypeptides of the present disclosure are highly stereoselective for the R-amine products of compound (2a) and compound (2c) and produce little or none of the S-amine compounds of (2b) or (2d). Chiral HPLC analysis of selected engineered polypeptides of the present disclosure showed that the R-amine products produced in at least 98% e.e, which is to be expected because the original wild-type transaminase from which they are derived is R-selective. Consequently, the trans: cis diastereomeric ratio measured herein closely approximates the diastereomeric ratio of compound (2a) to compound (2c). Values for diastereomeric excess ("d.e.") could also be calculated using the trans to cis ratio based on the assumption of high enantioselectivity for R-amine (e.e. of >98%) as follows: {[(2a)]+[(2d)]) ([(2b)]+[(2c)])}/{[(2a)]+ [(2b)]+[(2c)]+[(2d)]}.

Initial screening assays of transaminases showed that the engineered polypeptide of SEQ ID NO: 6 converted the substrate racemic mixture of compound (1) to the trans R-amine product of compound (2a) in nearly a 1:1 ratio (0.9 d.r.,-5.2% d.e.) with the cis R-amine product of compound (2c). The wild-type transaminase polypeptide of SEQ ID NO: 2 and engineered transaminase of SEQ ID NO: 4, were found to convert the substrate racemic mixture of compound (1) to the undesired cis isomer, (1R,2S)-2-(3,4-dimethoxyphenethoxy) cyclohexanamine (compound (2c)) in a significantly greater ratio than the desired trans R-amine product of compound (2a) (0.08 d.r.,-86% d.e.). Consequently, the engineered polypeptide of SEQ ID NO: 6 was used as the starting point for the further evolution of engineered polypeptides capable of providing the trans R-amine product of compound (2a) in at least a 2:1 ratio to the cis R-amine product of compound (2c) described herein.

The stereoselectivity (trans:cis d.r. and/or % d.e.), relative activity, and/or percent conversion, of each engineered polypeptide was determined relative to the positive control reference polypeptide of SEQ ID NO: 6 by measuring conversion of a racemic substrate mixture of compound (1) (i.e., a racemate of the (R)- and (S)-enantiomers of 2-(3,4-dimethoxyphenethoxy)cyclohexanone) to the trans R-amine and cis R-amine products of compound (2a) and compound (2c), respectively using a high-throughput (HTP) assay (as primary screen), and, in some cases, a secondary shake-flask powder (SFP) assay. The HTP assay values in Tables 2A, 2B, 2C and 2D were determined using *E. coli* clear cell lysates in 96 well-plate format of ~200 μL volume per well following assay reaction conditions as noted in the Tables.

Further details of and modifications to the HTP assay made for improved screening of engineered polypeptides are noted in Tables 2A, 2B, 2C and 2D and described in Example A. The SFP preparations are approximately 30% total protein and provide a more purified preparation of the engineered polypeptide. The SFP assay values in Table 2B were determined using SFP preparations of the engineered polypeptides in a 2.0 mL vial format following assays reaction conditions noted in Table 2B. Further details of and modifications to the SFP assay made for improved screening of engineered polypeptides are described in Example A.

TABLE 2A

| SEQ ID NO: (nt/aa) | Amino Acid Differences (relative to SEQ ID NO: 6) | Trans:Cis Ratio[2] (HTP assay[1]) | % d.e.[2] (HTP assay[1]) | Activity[2] relative to SEQ ID NO: 6 (HTP assay[1]) | % Conversion[5] (SFP assay[3,4]) |
|---|---|---|---|---|---|
| 5/6 | N/A | 0.9 | −5.2 | 1.00 | 99[4] |
| 7/8 | S124V; F136W; P210S; | 30.9 | 93.7 | 0.18 | 73[3] |
| 9/10 | T69V; F136W; S257F; | 25.3 | 92.4 | 0.47 | |
| 11/12 | L28P; T69V; F136W; | 22.9 | 91.6 | 0.59 | 92[3] |
| 13/14 | F56S; T69V; F136W; A265T; | 19.7 | 90.4 | 0.21 | |
| 15/16 | T69V; F136W; | 19.4 | 89.5 | 0.55 | 91[3] |
| 17/18 | T69V; S124I; F136W; | 17.0 | 88.1 | 0.60 | 89[3] |
| 19/20 | A38G; T69V; F136W; | 16.1 | 88.3 | 0.58 | |
| 21/22 | I10V; H14R; T69V; F136W; | 13.8 | 86.5 | 0.53 | |
| 23/24 | S124I; F136W; S181G; | 13.0 | 85.7 | 0.63 | |
| 25/26 | T69V; F136W; A265T; | 10.8 | 83.1 | 0.41 | |
| 27/28 | S124I; F136W; | 10.4 | 82.5 | 0.47 | |
| 29/30 | T69V; P99L; F136W; K142R; | 9.9 | 81.6 | 0.52 | |
| 31/32 | T69V; S124I; | 9.3 | 80.5 | 0.40 | |
| 33/34 | S124V; F136W; | 9.2 | 80.4 | 0.57 | |
| 35/36 | T69V; F136W; P210S; | 8.7 | 79.5 | 0.35 | |
| 37/38 | F136W; L209E; P210S; | 8.1 | 78.0 | 0.64 | |
| 39/40 | S124V; P210S; | 4.0 | 60.2 | 0.45 | 75[3] |
| 41/42 | T69V; | 3.9 | 58.7 | 0.49 | |
| 43/44 | T69V; C215Y; | 3.7 | 57.7 | 0.51 | |
| 45/46 | L209E; | 3.6 | 56.3 | 0.51 | 83[4] |
| 47/48 | T69V; N217S; | 3.6 | 56.6 | 0.50 | |
| 49/50 | A44V; P223N; | 3.6 | 56.0 | 0.18 | |
| 51/52 | P223N; | 3.5 | 55.0 | 0.23 | 39[4] |
| 53/54 | P223L; | 3.3 | 53.8 | 0.17 | |
| 55/56 | F56L; S124I; | 3.1 | 51.5 | 0.70 | |
| 57/58 | P223I; | 3.1 | 50.9 | 0.33 | 42[4] |
| 59/60 | T7A; S124L; | 3.0 | 49.9 | 0.72 | |
| 61/62 | I199Y; | 2.6 | 44.9 | 0.28 | |
| 63/64 | T69W; | 2.5 | 42.1 | 0.26 | |
| 65/66 | F136W; V171A; | 2.4 | 41.3 | 1.24 | 99[4] |
| 67/68 | S124F; G245S; | 2.4 | 40.9 | 0.47 | |
| 69/70 | L209D; | 2.3 | 40.2 | 0.33 | |
| 71/72 | S124F; L213P; | 2.3 | 40.1 | 0.37 | |
| 73/74 | P135Q; | 2.3 | 39.3 | 0.38 | |
| 75/76 | T69C; | 2.2 | 38.2 | 0.57 | |
| 77/78 | L209C; A242T; | 2.2 | 37.5 | 0.08 | |
| 79/80 | S124L; | 2.2 | 37.4 | 0.81 | |

TABLE 2A-continued

| SEQ ID NO: (nt/aa) | Amino Acid Differences (relative to SEQ ID NO: 6) | Trans:Cis Ratio[2] (HTP assay[1]) | % d.e.[2] (HTP assay[1]) | Activity[2] relative to SEQ ID NO: 6 (HTP assay[1]) | % Conversion[5] (SFP assay[3,4]) |
|---|---|---|---|---|---|
| 81/82 | F136W; | 2.1 | 36.3 | 1.25 | 99[4] |
| 83/84 | S124V; | 2.1 | 35.4 | 0.75 | |
| 85/86 | I199F; | 2.1 | 35.1 | 0.64 | |
| 87/88 | I199R; | 2.0 | 33.9 | 0.65 | |
| 89/90 | P223M; | 2.0 | 32.9 | 0.27 | |

[1] HTP assay conditions: a total HTP assay volume of 200 μL, 5 g/L of a racemic substrate mixture of compound (1), 100 μL clear cell lysate containing the engineered transaminase polypeptide, 1M isopropylamine (IPM), 1 mM PLP, 100 mM TEA, pH 10.0, 45° C. and 2 h reaction time with 245 rpm shaking. Cells were lysed by shaking for 0.5 to 1 hour at 250 rpm and 37° C. in 1 mL of lysis buffer containing 100 mM triethanolamine, 0.5 g/L lysozyme, and 0.4 g/L polymyxin B sulfate at pH 9.0.
[2] Stereoselectivity and Activity analysis: "Trans-Cis Ratio," "% d.e." and "Activity" were measured using achiral HPLC on either a Luna C18 or Ascentis C18 column as detailed in Example A. Activity relative to positive control (i.e., SEQ ID NO: 6) was determined as the ratio of percent conversion to the R-amine products (i.e., compound (2a) and (2c)) measured for the engineered polypeptide relative to the positive control polypeptide on the same HTP assay plate after 2 h reaction. Production of the R-amine products relative to S-amine products of 99% e.e. was confirmed using chiral HPLC analysis of polypeptide SFP samples from at least the following: SEQ ID NO: 6, 8, 12, 16, 18, 40, 42, 44, 46, 48, 50, 52, 58, 66, and 82.
[3] SFP assay conditions: 10 g/L substrate mixture of compound (1), 1.0 g/L of the engineered transaminase polypeptide SFP, 1.0 g/L PLP, 1M IPM, in an aqueous co-solvent solution of 0.2M borate buffer, 20% (v/v) DMSO, pH 10.5, 45° C. reaction temperature and overnight (15-18 h) reaction time.
[4] SFP assay conditions: 10 g/L substrate mixture of compound (1), 1.0 g/L of the engineered transaminase polypeptide SFP, 1.0 g/L PLP, 1M IPM, in an aqueous co-solvent solution of 0.1M triethanolamine buffer, 20% (v/v) DMSO, pH 10.0, 45° C. reaction temperature and 4.5 h reaction time.
[5] % Conversion analysis: Percent conversion was determined using achiral HPLC on an Ascentis C18 column as detailed in Example A by measuring the percent of the R-amine products (i.e., compound (2a) and (2c)) produced relative to the amount of racemic mixture of compound (1) for after the stated reaction time for the SFP assay.

TABLE 2B

| SEQ ID NO: (nt/aa) | Amino Acid Differences (relative to SEQ ID NO: 6) | Trans:Cis Ratio[3] (SFP Assay[1]) | Activity[4] relative to SEQ ID NO: 18 (HTP Assay[2]) |
|---|---|---|---|
| SFP Batch 1 | | | |
| 17/18 | T69V; S124I; F136W; | 12.7 | 1.00 |
| 91/92 | T69V; S124I; F136W; C215F | 18.9 | 1.73 |
| 93/94 | T69V; S124I; F136W; W156S; I267V; | 27.5 | 1.49 |
| SFP Batch 2 | | | |
| 17/18 | T69V; S124I; F136W; | 8 | 1.00 |
| 95/96 | T69V; S124I; S126T; F136W; Y150N; | 10.1 | 1.29 |
| 97/98 | T69V; S124I; F136W; Y150A; | 10.1 | 1.50 |
| 99/100 | T69V; S124I; S126T; F136W; | 7.5 | 1.19 |
| 101/102 | T69V; S124I; S126A; F136W; | 10.9 | 1.30 |

[1] SFP assay conditions: 100 g/L substrate mixture of compound (1), 1.0 g/L of the engineered transaminase polypeptide SFP, 1.0 g/L PLP, 1M IPM, in an aqueous co-solvent solution of 0.2M borate buffer, 40% (v/v) DMSO, pH 10.5, 45° C. reaction temperature and 24 h reaction time (with 400 rpm shaking).
[2] HTP assay conditions: 200 μL total volume, 50 g/L substrate mixture of compound (1), 40 μL of clear cell lysate containing the engineered transaminase polypeptide, 1 g/L PLP, 1M IPM, in an aqueous co-solvent solution of 0.2M borate buffer, 40% (v/v) DMSO, pH 10.5, 45° C. reaction temperature and 4 h reaction time (with 200 rpm shaking).
[3] Stereoselectivity analysis: "Trans-Cis Ratio" was measured using achiral HPLC on either a Zorbax column after running according to SFP assay conditions, further detailed in Example A.
[4] Activity analysis: Activity relative to positive control (i.e., SEQ ID NO: 6) was determined as the ratio of percent conversion to the R-amine products (i.e., compound (2a) and (2c)) measured for the engineered polypeptide relative to the positive control polypeptide on the same HTP assay plate after running according to HTP assay conditions, further detailed in Example A.

TABLE 2C

| SEQ ID NO: (nt/aa) | Amino Acid Differences (relative to SEQ ID NO: 6) | Fold-Improved Activity[1,2] (relative to SEQ ID NO: 92) | Fold-Improved Stability[3,4] (relative to SEQ ID NO: 92) |
|---|---|---|---|
| 103/104 | I41F; T69V; S124I; F136W; C215F; | 1.68 | — |
| 105/106 | S4L; T69V; S124I; F136W; D165N; C215F; | 2.23 | — |
| 107/108 | S124I; F136W; C215F; | 2.19 | — |
| 109/110 | T69V; S124I; F136W; T141L; C215F; | 1.66 | — |
| 111/112 | T69V; S124I; F136W; K142T; C215F; | 1.89 | — |
| 113/114 | F56G; T69V; S124I; F136W; C215F; | 2.02 | — |
| 115/116 | I55L; T69V; S124I; F136W; C215F; | 1.21 | — |
| 117/118 | T69V; I94L; S124I; F136W; C215F; | 1.23 | — |
| 119/120 | T69V; S124I; F136W; S182T; C215F; | 1.20 | — |
| 121/122 | Q58L; T69V; S124I; F136W; C215F; | 1.82 | — |
| 123/124 | S54P; T69V; S124I; F136W; C215F; | 1.48 | — |
| 125/126 | S54R; T69V; S124I; F136W; C215F; | 1.95 | — |
| 127/128 | S54N; T69V; S124I; F136W; C215F; | 1.41 | — |
| 129/130 | S54K; T69V; S124I; F136W; C215F; | 1.84 | — |
| 131/132 | T69V; S124I; F136W; C215F; I267V; | 1.85 | — |
| 133/134 | T69V; S124I; F136W; W156S; C215F; L218M; | 1.53 | — |
| 135/136 | A5N; A44Q; T69V; I108V; S124I; S126A; F136W; Y150A; C215F; L218M; V328I; | 2.12 | — |

TABLE 2C-continued

| SEQ ID NO: (nt/aa) | Amino Acid Differences (relative to SEQ ID NO: 6) | Fold-Improved Activity[1,2] (relative to SEQ ID NO: 92) | Fold-Improved Stability[3,4] (relative to SEQ ID NO: 92) |
|---|---|---|---|
| 137/138 | T69V; S124I; F136W; W156F; C215F; | 1.11 | — |
| 139/140 | T69V; S124I; F136W; W156T; C215F; | 1.19 | — |
| 141/142 | A2K; T69V; S124I; F136W; C215F; | 1.91 | — |
| 143/144 | A2Q; T69V; S124I; F136W; C215F; | 1.93 | — |
| 145/146 | A2S; T69V; S124I; F136W; C215F; | 2.13 | — |
| 147/148 | A2Q; T69V; S124I; F136W; C215F; | 1.81 | — |
| 149/150 | A5S; T69V; S124I; F136W; C215F; | 2.86 | — |
| 151/152 | A5T; T69V; S124I; F136W; C215F; | 3.42 | — |
| 153/154 | A5I; T69V; S124I; F136W; C215F; | 3.13 | — |
| 155/156 | A5H; T69V; S124I; F136W; C215F; | 3.20 | — |
| 157/158 | A5L; T69V; S124I; F136W; C215F; | 1.93 | — |
| 159/160 | A5V; T69V; S124I; F136W; C215F; | 2.52 | — |
| 161/162 | A5L; T69V; S124I; F136W; C215F; | 3.52 | — |
| 163/164 | E9Q; T69V; S124I; F136W; C215F; N296S; | 1.70 | — |
| 165/166 | S4I; T69V; S124I; F136W; C215F; | 2.33 | — |
| 167/168 | E9S; T69V; S124I; F136W; C215F; | 1.57 | — |
| 169/170 | P8T; T69V; S124I; F136W; C215F; | 2.02 | — |
| 171/172 | E9N; T69V; S124I; F136W; C215F; | 1.82 | — |
| 173/174 | S4L; T69V; S124I; F136W; C215F; | 1.76 | — |
| 175/176 | V11K; T69V; S124I; F136W; C215F; | 1.88 | — |
| 177/178 | A2S; A5H; T69V; S124I; S126A; F136W; W156S; C215F; I267V; | individual construct | — |
| 179/180 | A2S; A5H; T69V; S124I; F136W; C215F; | individual construct | — |
| 181/182 | A2S; A5N; A44Q; T69V; I108V; S124I; S126A; F136W; Y150A; C215F; L218M; V328I; | individual construct | — |
| 183/184 | G37R; T69V; S124I; F136W; C215F; | — | 2.26 |
| 185/186 | T22I; T69V; S124I; F136W; C215F; | — | 1.93 |
| 187/188 | E42A; T69V; S124I; F136W; C215F; | — | 3.04 |
| 189/190 | R52K; T69V; S124I; F136W; C215F; | — | 1.67 |
| 191/192 | T69V; S124I; F136W; R164A; C215F; | — | 1.75 |
| 193/194 | T69V; S124I; F136W; Q155A; C215F; | — | 2.00 |
| 195/196 | T69V; S124I; F136W; Y150F; C215F; | — | 1.71 |
| 197/198 | T69V; S124I; F136W; W156G; C215F; | — | 2.68 |
| 199/200 | T69V; S124I; F136W; W156A; C215F; | — | 1.78 |
| 201/202 | T69V; S124I; F136W; W156S; C215F; | — | 2.20 |
| 203/204 | T69V; S124I; F136W; I157L; C215F; | — | 1.83 |
| 205/206 | A5H; F56G; T69V; I94L; S124I; F136W; C215F; | 1.11 | — |

[1] Activity HTP Assay Conditions: a total HTP assay volume of 200 μL, 50 g/L of a racemic substrate mixture of compound (1), 20 μL clear cell lysate containing the engineered transaminase polypeptide, 1M isopropylamine (IPM), 1 g/L PLP, 40% DMSO, 0.2M borate buffer, pH 10.5, 45° C. and 4 h reaction time with 250 rpm shaking. Cells were lysed by shaking for 1 hour at 800 rpm and room temperature in 300 μL of lysis buffer containing 0.2M borate buffer, 0.5 g/L lysozyme, and 0.4 g/L polymyxin B sulfate at pH 10.5.
[2] Activity Analysis: "Activity" was measured using achiral HPLC on a Ascentis C18 column as detailed in Example 1. Activity relative to positive control (i.e., SEQ ID NO: 92) was determined as the ratio of percent conversion to the R-amine products (i.e., compound (2a) and (2c)) measured for the engineered polypeptide relative to the positive control polypeptide on the same HTP assay plate after 4 h reaction.
[3] Stability HTP assay conditions: a total HTP assay volume of 200 μL, 40 μL clear cell lysate containing the engineered transaminase polypeptide were incubated in 1M isopropylamine (IPM), 1 g/L PLP, 40% DMSO, 0.2M berate buffer, pH 10.5, 45° C. for 24 h. After incubation the reaction was started with the addition of a racemic substrate mixture of compound (1) to a reaction concentration of 50 g/L. The reaction was let to proceed for 4 h at 45° C. with 250 rpm shaking. Cells were lysed by shaking for 1 hour at 800 rpm and room temperature in 300 μL of lysis buffer containing 0.2M borate buffer, 0.5 g/L lysozyme, and 0.4 g/L polymyxin B sulfate at pH 10.5.
[4] Stability analysis: "Stability" was measured using achiral HPLC on a Ascentis C18 column as detailed in Example 1. Stability relative to positive control (i.e., SEQ ED NO: 92) was determined as the ratio of percent conversion to the R-amine products (i.e., compound (2a) and (2c)) measured for the engineered polypeptide relative to the positive control polypeptide on the same HTP assay plate after 24 h incubation followed by 4 h reaction.

TABLE 2D

| SEQ ID NO: (nt/aa) | Amino Acid Differences (relative to SEQ ID NO: 6) | Trans:Cis Ratio [1,2] | Activity [3,4] (relative to SEQ ID NO: 18) |
|---|---|---|---|
| 17/18 | T69V; S124I; F136W; | 38 | 1.00 |
| 125/126 | S54R; T69V; S124I; F136W; C215F; | 34 | 4.34 |
| 131/132 | T69V; S124I; F136W; C215F; I267V; | 19 | 3.63 |
| 155/156 | A5H; T69V; S124I; F136W; C215F; | 18 | 4.41 |
| 179/180 | A2S; A5H; T69V; S124I; F136W; C215F; | 19 | 4.98 |
| 205/206 | A5H; F56G; T69V; I94L; S124I; F136W; C215F; | 37 | 4.37 |

TABLE 2D-continued

| SEQ ID NO: (nt/aa) | Amino Acid Differences (relative to SEQ ID NO: 6) | Trans:Cis Ratio [1,2] | Activity [3,4] (relative to SEQ ID NO: 18) |
|---|---|---|---|
| 135/136 | A5N; A44Q; T69V; I108V; S124I; S126A; F136W; Y150A; C215F; L218M; V328I; | 44 | 2.07 |

[1] DSP specificity assay conditions: 100 g/L substrate mixture of compound (1), 5.0 g/L of a DSP powder of the engineered transaminase polypeptide, 1.0 g/L PLP, 1M IPM, in an aqueous co-solvent solution of 0.2M borate buffer, 40% (v/v) DMSO, pH 10.5, 45° C. reaction temperature and 24 h reaction time (with 400 rpm stirring).
[2] Stereoselectivity analysis: "Trans-Cis Ratio" was measured using achiral HPLC after running according to DSP specificity assay conditions.
[3] DSP activity assay conditions: 100 g/L substrate mixture of compound (1), 0.5 g/L of a DSP powder of the engineered transaminase polypeptide, 1.0 g/L PLP, 1M IPM, in an aqueous co-solvent solution of 0.2M borate buffer, 40% (v/v) DMSO, pH 10.5, 45° C. reaction temperature and 24 h reaction time (with 400 rpm stirring).
[4] Activity analysis: Activity relative to positive control (i.e., SEQ ID NO: 18) was determined as the ratio of percent conversion to the R-amine products (i.e., compound (2a) and (2c)) measured for the engineered polypeptide relative to the positive control polypeptide on the same DSP assay conditions.

The transaminase polypeptides useful in the process which are capable of converting compound (1a) to compound (2a) comprise an amino acid sequence selected from any one of SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206. As shown above in Tables 2A, 2B, 2C, and 2D, each of these exemplary engineered polypeptides comprises one or more amino acid residue differences as compared to SEQ ID NO: 6, and capable of converting a racemic mixture of compound (1) to the (1R, 2R)-trans amine product of compound (2a) in at least a 2:1 diastereomeric ratio relative to the (1R, 2S)-cis amine product of compound (2c) under suitable reaction conditions. The engineered transaminase polypeptides are capable of converting the racemic mixture of compound (1) to compound (2a) in even higher diastereomeric ratio relative to compound (2c) of at least about 3:1, at least about 4:1, at least about 8:1, at least about 10:1, at least about 15:1, at least about 20:1, or at least about 30:1, under suitable reaction conditions. In contrast, engineered transaminase reference polypeptide of SEQ ID NO: 6 is capable of converting a racemic mixture of compound (1) to the (1R, 2R)-trans amine product of compound (2a) in only about 0.9:1 diastereomeric ratio relative to the (1R, 2S)-cis amine product of compound (2c).

The amino acid differences of the exemplary engineered polypeptides associated with their improved properties are shown in Tables 2A, 2B, 2C and 2D and include one or more residue differences as compared to SEQ ID NO:6 at the following residue positions: X2; X4; X5; X7; X8; X9; X10; X11; X14; X22; X28; X37; X38; X41; X42; X44; X52; X54; X55; X56; X58; X69; X94; X99; X108; X124; X126; X135; X136; X141; X142; X150; X155; X156; X157; X164; X165; X171; X182; X199; X209; X210; X213; X215; X217; X218; X223; X245; X257; X265; X267; X296; and X328. The specific amino acid differences as compared to SEQ ID NO:6 at each of these positions that are associated with the improved properties of the exemplary polypeptides of Tables 2A, 2B, 2C, and 2D include: X2K; X2Q; X2S; X4I; X4L; X5H; X5I; X5L; X5N; X5S; X5T; X5V; X7A; X8T; X9N; X9Q; X9S; X10V; X11K; X14R; X22I; X28P; X37R; X38G; X41F; X42A; X44Q; X44V; X52K; X54L; X54N; X54P; X54R; X55L; X56G; X56L; X56S; X58L; X69C; X69V; X69W; X94L; X99L; X108V; X124F; X124I; X124L; X124R; X124V; X126A; X126T; X135Q; X136W; X141L; X142R; X142T; X150A; X150F; X150N; X155A; X156A; X156F; X156G; X156S; X156T; X157L; X164A; X165N; X171A; X182T; X199F; X199R; X199Y; X209C; X209D; X209E; X210S; X213P; X215F; X215Y; X217S; X218M; X223I; X223L; X223M; X223N; X245S; X257F; X265T; X267V; X296S; and X328.

Additionally, certain combinations of amino acid differences of the exemplary engineered polypeptides of Tables 2A, 2B, 2C and 2D and are associated with their improved properties including the combinations of amino acid differences as compared to SEQ ID NO: 6 selected from: (a) X124V, and X210S; (b) X124V, X136W, and X210S; (c) X69V, and X136W; (d) X69V, and X215Y; (e) X69V, and X217S; (f) X69V, X124I, and X136W; (g) X69V, X136W, and X257F; (h) X44V, and X223N; (i) X56S, X69V, X136W, and X265T; and (j) X28P, X69V, and X136W.

In addition to the exemplary engineered polypeptides of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206, the process of the present disclosure can be carried out using engineered transaminase polypeptides having improved enzymatic properties (e.g., as disclosed above) and comprising further modifications of the amino acid sequence. Such engineered polypeptides can be derived from the exemplary polypeptides and have amino acid sequences retaining some percent identity to the exemplary engineered polypeptides and one or more of the amino acid differences relative to SEQ ID NO: 6 that are associated with the improved enzymatic property. Techniques and methods for deriving further engineered polypeptides are known in the art and include the methods of directed evolution as described herein.

Any of the exemplary engineered polypeptides of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206 can be used as the starting amino acid sequence (i.e., the "backbone" sequence) for subsequent rounds of evolution in which a library of genes having encoding additional amino acid differences in the backbone (e.g., adding in new combinations of various amino acid differences from other polypeptides in Tables 2A, 2B, 2C and 2D) is synthesized, expressed, and screened in high-throughput for particular improved properties (e.g., thermostability, total substrate conversion, stereoselectivity, etc.). The design of the libraries can be controlled such that only certain amino acid positions are allowed to change, while others are not. Thus, a backbone set of amino acid differences that are associated with improved properties can be maintained throughout the directed evolution process. The most improved engineered polypeptides from each round could then be used as the parent "backbone" sequence for subsequent rounds of evolution. The resulting engineered transaminase polypeptides having further improvements in its properties will retain some or all of the starting backbone amino acid differences and include new amino acid differences, typically while retaining an overall sequence identity to the starting backbone of at least 80%. It is contemplated, however, that one or more of the backbone amino acid differences can be changed during the directed evolution process leading to further improved properties in the engineered polypeptides. Further improvements at later rounds of evolution such as "fine tuning" an engineered polypeptide for certain process conditions (e.g., solvent conditions/concentrations, increased substrate and/or cofactor loading, pH, and temperature changes) may be generated by including amino acid differences at positions that had been maintained as unchanged throughout earlier rounds of evolution.

In some embodiments, the engineered transaminase polypeptides useful in the process of the instant invention are capable of converting a racemic mixture of compound (1) to the (1R, 2R)-trans amine product of compound (2a) in at least a 2:1 diastereomeric ratio relative to the (1R,2S)-cis amine product of compound (2c) under suitable reaction conditions, and comprises an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206. The amino acid sequence can include one or more residue differences as compared to SEQ ID NO:6 at the following residue positions: X2; X4; X5; X7; X8; X9; X10; X11; X14; X22; X28; X37; X38; X41; X42; X44; X52; X54; X55; X56; X58; X69; X94; X99; X108; X124; X126; X135; X136; X141; X142; X150; X155; X156; X157; X164; X165; X171; X182; X199; X209; X210; X213; X215; X217; X218; X223; X245; X257; X265; X267; X296; and X328. The amino acid sequence can include one or more residue differences as compared to SEQ ID NO:6 selected from the following: X2K; X2Q; X2S; X4I; X4L; X5H; X5I; X5L; X5N; X5S; X5T; X5V; X7A; X8T; X9N; X9Q; X9S; X10V; X11K; X14R; X22I; X28P; X37R; X38G; X41F; X42A; X44Q; X44V; X52K; X54K; X54N; X54P; X54R; X55L; X56G; X56L; X56S; X58L; X69C; X69V; X69W; X94L; X99L; X108V; X124F; X124I; X124L; X124R; X124V; X126A; X126T; X135Q; X136W; X141L; X142R; X142T; X150A; X150F; X150N; X155A; X156A; X156F; X156G; X156S; X156T; X157L; X164A; X165N; X171A; X182T; X199F; X199R; X199Y; X209C; X209D; X209E; X210S; X213P; X215F; X215Y; X217S; X218M; X223I; X223L; X223M; X223N; X245S; X257F; X265T; X267V; X296S; and X328I.

In some embodiments, the engineered transaminase polypeptides useful in the process of the instant invention are capable of converting a racemic mixture of compound (1) to the (1R,2R)-trans amine product of compound (2a) in at least a 2:1 diastereomeric ratio relative to the (1R,2S)-cis amine product of compound (2c) under suitable reaction conditions and comprising an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206, further comprises one or more combinations of amino acid differences as compared to SEQ ID NO: 6 selected from the following: (a) X124V, and X210S; (b) X124V, X136W, and X210S; (c) X69V, and X136W; (d) X69V, and X215Y; (e) X69V, and X217S; (f) X69V, X124I, and X136W; (g) X69V; X136W, and X257F; (h) X44V, and X223N; (i) X56S, X69V, X136W, and X265T; and (j) X28P, X69V, and X136W. In addition to one or more of the above combinations, the engineered polypeptide amino acid sequence can further comprise one or more amino acid residue differences as compared to SEQ ID NO: 6 selected from the following: X2K; X2Q; X2S; X4I; X4L; X5H; X5I; X5L; X5N; X5S; X5T; X5V; X54K; X54N; X54P; X54R; X56G; X94L; X124I; X126A; X126T; X150A; X150N; X156S; X215F; and X267V.

In some embodiments, the engineered transaminase polypeptides useful in the process of the instant invention are capable of converting a racemic mixture of compound (1) to the (1R, 2R)-trans amine product of compound (2a) in at least a 2:1 diastereomeric ratio relative to the (1R,2S)-cis amine product of compound (2c) under suitable reaction conditions and comprising an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206, comprises an amino acid difference as compared to SEQ ID NO: 6 at one or more of the following positions: X28; X69; X124; X126; X136; X150; X156; X199; X209; X215; X217; and X223; and further comprises an amino acid difference as compared to SEQ ID NO: 6 at one or more of the following positions: X2; X4; X5; X7; X8; X9; X10; X11; X14; X22; X37; X38; X41; X42; X44; X52; X54; X55; X56; X58; X94; X99; X108; X126; X135; X141; X142; X155; X157; X164; X165; X171; X182; X210; X213; X218; X245; X257; X265; X267; X296; and X328. In some embodiments, the amino acid differences as compared to SEQ ID NO: 6 at positions X28; X69; X124; X126; X136; X150; X156; X199; X209; X215; X217; and/or X223, are selected from the following: X28P; X69C; X69V; X69W; X124F; X124I; X124L; X124R; X124V; X126A; X126T; X136W; X150A; X150N; X156S; X199F; X199R; X199Y; X209C; X209D; X209E; X215F; X215Y; X217S; X223I; X223L; X223M; and X223N. The amino acid differences of the transaminase polypeptide as compared to SEQ ID NO: 6 at positions X28; X69; X124; X126; X136; X150; X156; X199; X209; X215; X217; and/or X223 are selected from the following: X28P; X69C; X136W; X150N; X156S; X199F; X199Y; and X217S. In some embodiments of the process, the amino acid differences as compared to SEQ ID NO: 6 at positions X2; X4; X5; X7; X8; X9; X10; X11; X14; X22; X37; X38; X41; X42; X44; X52; X54; X55; X56; X58; X94; X99; X108; X135; X141; X142; X155; X157; X164; X165; X171; X182; X210; X213; X218; X245; X257; X265; X267; X296; and X328 are selected from: X2K; X2Q; X2S; X4I; X4L; X5H; X5I; X5L; X5N; X5S; X5T; X5V; X7A; X8T; X9N; X9Q; X9S; X10V; X11K; X14R; X22I; X37R; X380; X41F; X42A; X44Q; X44V; X52K; X54K; X54N; X54P; X54R; X55L; X56G; X56L; X56S; X58L; X94L; X99L; X108V; X135Q; X141L; X142R; X142T; X155A; X156A; X156F;

X156G; X156S; X156T; X157L; X164A; X165N; X171A; X182T; X210S; X213P; X218M; X245S; X257F; X265T; X267V; X296S; and X328I.

As mentioned above, the polypeptide sequence of SEQ ID NO: 6 used as the starting backbone for the generation of the exemplary engineered transaminase polypeptides is also an engineered transaminase polypeptide having the following 24 amino acid differences relative to the naturally occurring transaminase of *Arthrobacter* sp. KNK168 (SEQ ID NO: 2): S8P; Y60F; L61Y; H62T; V65A; V69T; D81G; M94I; 196L; F122I; G136F; A169L; V199I; A209L; G215C; G217N; 5223P; L269P; L273Y; T282S; A284G; P297S; I306V; and S321P. Thus, in some embodiments, the engineered transaminase polypeptides useful in the process of the instant invention are capable of converting a racemic mixture of compound (1) to the (1R, 2R)-trans amine product of compound (2a) in at least a 2:1 diastereomeric ratio relative to the (1R, 2S)-cis amine product of compound (2c) under suitable reaction conditions and comprising an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206, further comprises a polypeptide amino acid sequence that does not include an amino acid difference as compared to SEQ ID NO: 6 at one or more of the following positions: X8; X60; X61; X62; X65; X81; X94; X96; X122; X169; X269; X273; X282; X284; X297; X306; and X321. In some embodiments of the process, the amino acid sequence that does not include an amino acid difference as compared to SEQ ID NO: 6 at any of the following positions: X8; X60; X61; X62; X65; X81; X94; X96; X122; X169; X269; X273; X282; X284; X297; X306; and X321.

In some embodiments, the present process uses a non-naturally occurring polypeptide capable of converting a racemic mixture of compound (1) to the (1R,2R)-trans amine product of compound (2a) in at least a 2:1 diastereomeric ratio relative to the (1R,2S)-cis amine product of compound (2c) under suitable reaction conditions, comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206, and further comprises the set of one or more amino acid residue differences as compared to SEQ ID NO:6 found in any one of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206.

In addition to the residue positions specified above, any of the engineered transaminase polypeptides useful in the process disclosed herein can further comprise other residue differences relative to the reference polypeptide sequence of SEQ ID NO: 6 at other residue positions i.e., residue positions other than X2; X4; X5; X7; X8; X9; X10; X11; X14; X22; X28; X37; X38; X41; X42; X44; X52; X54; X55; X56; X58; X69; X94; X99; X108; X124; X126; X135; X136; X141; X142; X150; X155; X156; X157; X164; X165; X171; X182; X199; X209; X210; X213; X215; X217; X218; X223; X245; X257; X265; X267; X296; and X328. Residue differences at these other residue positions provide for additional variations in the amino acid sequence without altering the polypeptide's ability to convert a racemic mixture of compound (1) to the (1R,2R)-trans amine product of compound (2a) in at least a 2:1 diastereomeric ratio relative to the (1R,2S)-cis amine product of compound (2c) under suitable reaction conditions. Accordingly, in some embodiments of the instant process, in addition to the set of amino acid residue differences of any one of the engineered transaminase polypeptides of any one of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206, the sequence can further comprise one or several residue differences at other amino acid residue positions as compared to the SEQ ID NO: 6, or 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40 residue differences at other amino acid residue positions as compared to the SEQ ID NO: 6. The number of differences as compared to the reference sequence can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, 50, 55, or 60 residue positions. The residue differences at other amino acid residue positions can comprise conservative substitutions and/or non-conservative substitutions as compared to a reference polypeptide of the wild-type polypeptide of SEQ ID NO: 2 or the engineered polypeptides of SEQ ID NO: 4 or 6.

Amino acid residue differences at other positions relative to the wild-type sequence of SEQ ID NO: 2 and the affect of these differences on enzyme function are provide by other engineered transaminase polypeptides disclosed in U.S. application Ser. No. 12/714,397, filed Feb. 26, 2010, which is hereby incorporated by reference herein. One or more of the amino acid differences as compared to the wild-type sequence of SEQ ID NO: 2, provided in the engineered transaminase polypeptide amino acid sequences of U.S. application Ser. No. 12/714,397, filed Feb. 26, 2010 (see e.g., Table 2 of U.S. application Ser. No. 12/714,397), could also be introduced into a engineered transaminase polypeptide of the present disclosure. Any of the engineered polypeptide disclosed herein can comprise an amino acid sequence with the further proviso that the sequence does not comprise an amino acid residue differences as compared to SEQ ID NO: 6 at one or more of the following positions: X28; X69; X124; X126; X136; X150; X156; X199; X209; X215; X217; and X223 Any of the engineered polypeptide disclosed herein can comprise an amino acid sequence with the further proviso that the sequence does not comprise one or more amino acid residue differences as compared to SEQ ID NO: 6 selected from the following: X28P; X69C; X136W; X150N; X156S; X199F; X199Y; and X217S.

In some embodiments, the present process uses engineered transaminase polypeptides that comprise a fragment of any of the engineered transaminase polypeptides described herein that retains the functional activity and/or improved property of that engineered transaminase. A polypeptide fragment capable of converting a racemic mixture of compound (1) to the (1R,2R)-trans amine product of compound (2a) in at least a 2:1 diastereomeric ratio relative to the (1R,2S)-cis amine product of compound (2c) under suitable reaction conditions, wherein the fragment comprises at least about 80%, 90%, 95%, 98%, or 99% of a full-length amino acid sequence of a engineered transaminase polypeptide of the present disclosure, may include an exemplary engineered polypeptide of SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206.

In some embodiments, the process of the instant invention uses an engineered transaminase polypeptide having an amino acid sequence comprising a deletion as compared to any one of the engineered transaminase polypeptides described herein, such as the exemplary engineered polypeptides of SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206. Thus, for each and every embodiment of the engineered transaminase polypeptides of the present process, the amino acid sequence can comprise deletions of one or more amino acids, 2 or more amino acids, 3 or more amino acids, 4 or more amino acids, 5 or more amino acids, 6 or more amino acids, 8 or more amino acids, 10 or more amino acids, 15 or more amino acids, or or more amino acids, up to 10% of the total number of amino acids, up to 10% of the total number of amino acids, up to 20% of the total number of amino acids, or up to 30% of the total number of amino acids of the transaminase polypeptides, where the associated functional activity and/or improved properties of the engineered transaminase described herein is maintained. The deletions can comprise, 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, 1-50, 1-55, or 1-60 amino acid residues. The number of deletions can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, 50, 55, or 60 amino acids. In some embodiments, the deletions can comprise deletions of 1, 2, 3, 4, 5, 6, 7, 8, 9, 10, 11, 12, 13, 14, 15, 16, 18, 20, 21, 22, 23, 24, 25 or 30 amino acid residues.

In some embodiments, the process uses an engineered transaminase polypeptide having an amino acid sequence comprising an insertion as compared to any one of the engineered transaminase polypeptides described herein, such as the exemplary engineered polypeptides of SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206. Thus, for each and every embodiment of the transaminase polypeptides of utilized in the instant process, the insertions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, where the associated functional activity and/or improved properties of the engineered transaminase described herein is maintained. The insertions can be to amino or carboxy terminus of the transaminase, or internal portions of the transaminase polypeptide.

In some embodiments, the present process uses a non-naturally occurring polypeptide capable of converting a racemic mixture of compound (1) to the (1R,2R)-trans amine product of compound (2a) in at least a 2:1 diastereomeric ratio relative to the (1R, 2S)-cis amine product of compound (2e) under suitable reaction conditions, which comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 6, with the proviso that the amino acid sequence is not identical to any one or more of the engineered transaminase polypeptides amino acid sequences disclosed in U.S. application Ser. No. 12/714,397, filed Feb. 26, 2010. In some embodiments, the polypeptides of the instant process can be in the form of fusion polypeptides in which the engineered polypeptides are fused to other polypeptides, such as, by way of example and not limitation, antibody tags (e.g., myc epitope), purification sequences (e.g., His tags for binding to metals), and cell localization signals (e.g., secretion signals). Thus, the engineered polypeptides described herein can be used with or without fusions to other polypeptides.

The engineered transaminase polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminehexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (NaI); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (PM); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys (methylbenzyl), Cys (nitropyridinesulfenyl), Glu(δ-benzylester), Gln(xanthyl), Asn(N-δ-xanthyl), His(bom), His(benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid. As described above the various modifications introduced into the naturally occurring polypeptide to generate an engineered transaminase enzyme can be targeted to a specific property of the enzyme.

In some embodiments, the transaminase polypeptides used in the instant process are bound to a substrate. The transaminase polypeptide can be bound non-covalently or covalently. Various methods for conjugation to substrates, e.g., membranes, beads, glass, etc. are described in, among others, Hermanson, G. T., Bioconjugate Techniques, Second Edition, Academic Press; (2008), and Bioconjugation Protocols: Strategies and Methods, In Methods in Molecular Biology, C. M. Niemeyer ed., Humana Press (2004); the disclosures of which are incorporated herein by reference.

Description of Polynucleotides, Control Sequences, Expression Vectors, and Host Cells Useful for Preparing Engineered Transaminase Polypeptides The polynucleotides encoding the exemplary engineered transaminases useful in the present process are selected from SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, and 205. These polynucleotides may be manipulated in a variety of ways well-known in the art to provide for expression of the engineered polypeptides, including further sequence alteration by codon-optimization to improve expression, insertion in a suitable expression with or without further control sequences, and transformation into a host cell suitable for expression and production of the polypeptide.

The polynucleotides may be operatively linked to one or more heterologous regulatory sequences that control gene expression to create a recombinant polynucleotide capable of expressing the polypeptide. Expression constructs containing a heterologous polynucleotide encoding the engineered transaminase can be introduced into appropriate host cells to express the corresponding transaminase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be polynucleotides can be made, all of which encode the improved transaminase enzymes disclosed herein. Thus, having identified a particular based on the amino acid sequences of the engineered transaminase polypeptides disclosed herein, those skilled in the art could make any number of different nucleic acids by simply modifying the sequence of one or more codons in a way which does not change the amino acid sequence of the protein. Each and every possible variation of polynucleotides that could be made by selecting combinations based on the possible codon choices is contemplated, and all such variations are to be considered specifically disclosed for any polypeptide disclosed herein, including the amino acid sequences of the exemplary engineered polypeptides summarized in Tables 2A, 2B, 2C and 2D and disclosed in the sequence listing incorporated by reference herein as SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206.

Codons can be selected to fit the host cell in which the protein is being produced. For example, preferred codons used in bacteria are used to express the gene in bacteria; preferred codons used in yeast are used for expression in yeast; and preferred codons used in mammals are used for expression in mammalian cells.

All codons need not be replaced to optimize the codon usage of the transaminases since the natural sequence will comprise preferred codons and because use of preferred codons may not be required for all amino acid residues. Consequently, codon optimized polynucleotides encoding the transaminase enzymes may contain preferred codons at about 40%, 50%, 60%, 70%, 80%, or greater than 90% of codon positions of the full length coding region.

A host cell useful for expressing a transaminase can comprise a polynucleotide encoding an improved transaminase polypeptide of the present disclosure, the polynucleotide being operatively linked to one or more control sequences for expression of the transaminase enzyme in the host cell. Host cells for use in expressing the polypeptides encoded by the expression vectors of the present disclosure are well known in the art and include but are not limited to, bacterial cells, such as *E. coli., Arthrobacter* sp. KNK168, *Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the transaminase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

An exemplary host cell is *Escherichia coli* W3110 (AfhuA). The expression vector was created by operatively linking a polynucleotide encoding an improved transaminase into the plasmid pCK110900I operatively linked to the lac promoter under control of the lad repressor. The expression vector also contained the P15a origin of replication and the chloramphenicol resistance gene.

Methods of Generating Engineered Transaminase Polypeptides

To make the improved polynucleotides and polypeptides for use in the present process, the naturally-occurring transaminase enzyme that catalyzes the transamination reaction is obtained (or derived) from *Arthrobacter* sp. KNK168. In some embodiments, the parent polynucleotide sequence is codon optimized to enhance expression of the transaminase in a specified host cell. The parental polynucleotide sequence encoding the wild-type polypeptide of *Arthrobacter* sp. KNK168 has been described (see e.g., Iwasaki et al., *Appl. Microbiol. Biotechnol.*, 2006, 69: 499-505). Preparation of engineered transaminases based on this parental sequence are also described in U.S. application Ser. No. 12/714,397, filed Feb. 26, 2010 and International application PCT/US2010/025685, filed Feb. 26, 2010.

The engineered transaminases can be obtained by subjecting the polynucleotide encoding the naturally occurring transaminase to mutagenesis and/or directed evolution methods, as discussed above. An exemplary directed evolution technique is mutagenesis and/or DNA shuffling as described in Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529). Mutagenesis and directed evolution techniques useful for the purposes herein are also described in e.g., Ling, et al., 1997, Anal. Biochem. 254(2):157-78; Dale et al., 1996, "Oligonucleotide-directed random mutagenesis using the phosphorothioate method," in Methods Mol. Biol. 57:369-74; Smith, 1985, Ann. Rev. Genet. 19:423-462; Botstein et al., 1985, Science 229:1193-1201; Carter, 1986, Biochem. J. 237:1-7; Kramer et al., 1984, Cell, 38:879-887; Wells et al., 1985, Gene 34:315-323; Minshull et al., 1999, Curr Opin Chem Biol 3:284-290; Christians et al., 1999, Nature Biotech 17:259-264; Crameri et al., 1998, Nature 391:288-291; Crameri et al., 1997, Nature Biotech 15:436-438; Zhang et al., 1997, Proc Natl Acad Sci USA 94:45-4-4509; Crameri et al., 1996, Nature Biotech 14:315-319; Stemmer, 1994, Nature 370:389-391; Stemmer, 1994, Proc Natl Acad Sci USA 91:10747-10751; PCT Publ. Nos. WO 95/22625, WO 97/0078, WO 97/35966, WO 98/27230, WO 00/42651, and WO 01/75767; and U.S. Pat. No. 6,537,746. All publications and patent are hereby incorporated by reference herein.

The clones obtained following mutagenesis treatment can be screened for engineered transaminases having a desired improved enzyme property. Measuring enzyme activity from the expression libraries can be performed using the standard biochemistry techniques, such as HPLC analysis following OPA derivatization of the product amine. Where the improved enzyme property desired is thermostability, enzyme activity may be measured after subjecting the enzyme preparations to a defined temperature and measuring the amount of enzyme activity remaining after heat treatments. Clones containing a polynucleotide encoding a transaminase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the disclosure can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources.

Methods of Using the Engineered Transaminase Enzymes and Compounds Prepared Therewith Any of the engineered transaminase polypeptides disclosed herein capable of converting a racemic mixture of compound (1) to the (1R,2R)-trans amine product of compound (2a) in at least a 2:1 diastereomeric ratio relative to the (1R,2S)-cis amine product of compound (2c) under suitable reaction conditions can be used in a method for the conversion of the substrate compound (1a), (R)-2-(3,4-dimethoxyphenethoxy)cyclohexanone, to the product of compound (2a), (1R,2R)-2-(3,4-dimethoxyphenethoxy)cyclohexanamine. The method for preparing compound (2a) can comprise contacting compound (1a) with an engineered transaminase polypeptide of the present disclosure in the presence of an amino donor under suitable reaction conditions.

As described further below, and illustrated in the Examples, the present process contemplates ranges of suitable reaction conditions that can be used in the process, particularly the enzymatic step, including but not limited to ranges of pH, temperature, buffer, solvent system, substrate loading, mixture of substrate compound enantiomers (e.g., a racemic mixture), polypeptide loading, cofactor loading, atmosphere, and reaction time. Further suitable reaction conditions for carrying out the method for enzymatic conversion of compound (1a) to compound (2a) using an engineered transaminase polypeptide described herein can be readily optimized by routine experimentation that includes, but is not limited to, contacting the engineered transaminase polypeptide and substrate (1a) under experimental reaction conditions of concentration, pH, temperature, solvent conditions, and detecting the production of compound (2a), for example, using the methods described in the Examples provided herein.

The combination of improved enantioselectivity and diastereoselectivity of the engineered transaminase polypeptides of the present disclosure provides for a method capable of converting a racemic mixture of compound (1) to compound (2a) in a diastereomeric ratio relative to cis R-amine compound (2c) of at least about 2:1 and with high conversion yields (e.g., 85% or greater).

Accordingly, in some embodiments the high enantioselectivity for the R-amine products provides for a process wherein a mixture of compound (1a) and compound (1b) may be used and the method results in the R-amine products of compound (2a) and (2c) in an enantiomeric excess relative to the S-amine products of compound (2d) and (2b) of at least about 95% e.e., at least about 96% e.e., at least about 97% e.e., at least about 98% e.e., at least about 99% e.e., or at least about 99.9% e.e.

Similarly, the high diastereoselectivity for the trans R-amine product of compound (2a) provides for a method wherein a mixture of compound (1a) and compound (1b) may be used and the method results in the trans R-amine product of compound (2a) in a diastereomeric ratio relative to cis R-amine compound (2c) of at least about 2:1, at least about 3:1, at least about 4:1, at least about 8:1, at least about 10:1, at least about 15:1, at least about 20:1, or at least about 30:1.

In some embodiments, the engineered transaminase polypeptide is present at sufficient amounts to carry out the conversion of the substrate to product to the desired percent conversion of substrate to product in a defined time period under a defined process condition. In some embodiments, conversion yields of the product of compound (2a) generated in the reaction mixture are generally greater than about 50%, may also be greater than about 60%, may also be greater than about 70%, may also be greater than about 80%, may also be greater than 90%, and are often greater than about 97%.

The improved stereoselectivity and activity of the engineered transaminase polypeptides used for the conversion of compound (1a) to compound (2a) provides for methods wherein higher percentage conversion can be achieved with lower concentrations of the engineered polypeptide. The use of lower concentration of the engineered polypeptide in a process comprising a conversion of compound (1a) to compound (2a) also reduces the amount of residual protein that may need to be removed in subsequent steps for purification of compound (2a). In some embodiments of the process, the suitable reaction conditions comprise an engineered polypeptide concentration of about 0.1 to about 15 g/L, about 0.5 to about 10 g/L, about 1.0 to about 5 g/L, about 2 to about 5 g/L, about 15 g/L, about 10 g/L, about 5 g/L, about 3 g/L, about 2 g/L, about 1.5 g/L, about 1.0 g/L, about 0.75 g/L, or even lower concentration.

In some embodiments of the process, the amino donor comprises a compound of Formula II, selected from isopropylamine (also referred to herein as "IPM"), putrescine, L-lysine, α-phenethylamine, D-alanine, L-alanine, or D,L-alanine, or D,L-ornithine. In some embodiments, the amino donor is selected from the group consisting of IPM, putrescine, L-lysine, D- or L-alanine. In some embodiments, the amino donor is IPM. In some embodiments, the suitable reaction conditions comprise the amino donor at a concentration of at least about 0.5 M, at least about 1.0 M, at least about 2.5 M, at least about 5.0 M, at least about 7.5 M, at least about 10.0 M, or more.

Suitable reaction conditions using the engineered transaminase polypeptides also typically require a cofactor, although in many embodiments the engineered transaminases disclosed herein require far less cofactor than reactions catalyzed with wild-type transaminase enzymes. Cofactors useful in the methods using the engineered transaminase enzymes described herein include, but are not limited to, pyridoxal-5'-phosphate (also known as pyridoxal-phosphate, PLP, P5P). In some embodiments, the cofactor is a member of the vitamin B6 family, selected from PLP, pyridoxine (PN), pyridoxal (PL), pyridoxamine (PM), and their phosphorylated counterparts; pyridoxine phosphate (PNP), and pyridoxamine phosphate (PMP). In some embodiments, the cofactor is PLP. In some embodiments, the cofactor is present naturally in the cell extract and does not need to be supplemented. In embodiments of the methods, using partially purified, or purified transaminase enzyme, the suitable reaction conditions comprise cofactor added to the enzyme reaction mixture. In some embodiments, the cofactor is added either at the beginning of the reaction and/or additional cofactor is added during the reaction.

In some embodiments of the process, the suitable reaction conditions can further comprise the presence of the reduced cofactor, nicotinamide adenine dinucleotide (NADH), which can act to limit the inactivation of the transaminase enzyme (see e.g., van Ophem et al., 1998, Biochemistry 37(9):2879-88). In such embodiments where NADH is present, a cofactor regeneration system, such as glucose dehydrogenase (GDH) and glucose or formate dehydrogenase and formate can be used to regenerate the NADH in the reaction medium. Generally, the method of converting compound (1a) to compound (2a) using the engineering transaminase polypeptides of the present disclosure can be carried out wherein the suitable reaction conditions comprise a mixture of the substrate compound (1a) and its opposite enantiomer of compound (1b). Accordingly, in some embodiments, the suitable reaction conditions comprise that the mixture of compound (1a) and compound (1b) at the start of the reaction is a racemic mixture of compound (1).

As mentioned above, compounds (1a) and compound (1b) are opposite enantiomers that are capable of undergoing an epimerization reaction that provides an equilibrium between them (see Scheme C above) under certain conditions (e.g., preferably pH>9 and temperature >50° C.). Because the engineered transaminase polypeptides of the present disclosure exhibit a highly stereoselective preference for the substrate of compound (1a), this equilibrium between the two enantiomers provides for the ability to carry out a dynamic kinetic resolution of the two enantiomers. Accordingly, in some embodiments of the suitable reaction conditions comprise a mixture of an initial amount of the substrate compound (1a) with its opposite enantiomer of compound (1b) in the reaction solution in contact with the polypeptide, and the amount of product of compound (2a) formed by the reaction is greater than the starting amount (i.e., initial substrate loading) of compound (1a). In some embodiments, where the suitable reaction conditions comprise a racemic mixture of compound (1) in the reaction solution, the yield of product of compound (2a) formed by the reaction relative to the starting amount of the compound (1) is greater than 50%, greater than 60%, greater than 70%, greater than 80%, greater than 90%, greater than 95%, or more.

In some embodiments of the process, the suitable reaction conditions comprise a substrate compound (1a) loading of at least about 5 g/L, at least about 10 g/L, at least about 15 g/L, at least about 20 g/L, at least about 30 g/L, at least about 50 g/L, at least about 75 g/L, at least about 100 g/L, or even greater. In embodiments of the process wherein a racemic mixture of compound (1) is used, the suitable reaction conditions comprise a substrate of compound (1) loading of at least about 10 g/L, at least about 20 g/L, at least about 30 g/L, at least about 40 g/L, at least about 60 g/L, at least about 100 g/L, at least about 150 g/L, at least about 200 g/L, or even greater. The values for substrate loadings provided herein are based on the molecular weight of compound (1a), however it also contemplated that the equivalent molar amounts of various hydrates and salts of compound (1a) also can be used in the methods.

As noted above, in some embodiments the process is carried out in which the amino donor is IPM, and the suitable reaction conditions comprise an IPM concentration of at least about 0.5 M, at least about 1.0 M, at least about 2.5 M, at least about 5.0 M, at least about 7.5 M, at least about 10.0 M, or more. In some embodiments, when IPM is used as the amino donor, the process further comprises removal of the carbonyl by-product acetone which is formed from the isopropylamine.

In certain embodiments of the process, the temperature of the suitable reaction conditions can be chosen to maximize the reaction rate at higher temperatures while maintaining the activity of the enzyme for sufficient duration for efficient conversion of the substrate to the product. Higher temperatures increase the rate of epimerization of compound (1b) to compound (1a), and thereby allow for a dynamic kinetic resolution process that provides increased product of compound (2a) yield from mixture of the substrate compound (1a) with it opposite enantiomer, compound (1b). Where higher temperatures are used, polypeptides with increased thermostability can be selected to carry out the process. The engineered polypeptides of the present disclosure have increased thermal stability relative to naturally occurring transaminase polypeptide e.g., the wild type polypeptide of SEQ ID NO: 2. This allows the engineered polypeptides to be used in methods for converting compound (1a) to compound (2a) at higher temperatures which can result in increased conversion rates and improved substrate solubility characteristics for the reaction, although substrate or product degradation at higher temperatures can contribute to decreased process yields. In some embodiments of the method the suitable reaction conditions comprise a temperature of between about 25° C. and about 75° C., between about 35° C. and about 65° C., between about 40° C. and about 60° C., at least about 30° C., at least about 35° C., at least about 40° C., at least about 45° C., or at least about 50° C., or about 60° C., or more. In certain embodiments, the temperature during the enzymatic reaction can be maintained at a temperature throughout the course of the reaction. In some embodiments, the temperature during the enzymatic reaction can be adjusted over a temperature profile during the course of the reaction.

The methods for preparing compound (2a) of the present disclosure are generally carried out in a solvent. Suitable solvents include water, aqueous buffer solutions, organic solvents, and/or co-solvent systems, which generally comprise aqueous solvents and organic solvents. The aqueous solvent (water or aqueous co-solvent system) may be pH-buffered or unbuffered.

In certain embodiments, the process for preparing compound (2a) using the engineered transaminase polypeptides of the present disclosure can be carried out with the pH of the reaction mixture may be maintained at a desired pH or within a desired pH range by the addition of an acid or a base during the course of the reaction. In certain embodiments of the process, the pH of the reaction mixture may be allowed to change, or be changed during the course of the reaction. Thus, it is contemplated that in some embodiments the pH may be controlled by using an aqueous solvent that comprises a buffer. Suitable buffers to maintain desired pH ranges are known in the art and include, for example, phosphate buffer, triethanolamine buffer, and the like. Combinations of buffering and acid or base addition may also be used. In some embodiments of the method the suitable reaction conditions comprise a solution pH of between about pH 8.5 and about pH 11.5, between about pH 9.0 and about pH 11.5, between about pH 9.5 and about pH 11.0, at least about pH 8.5, at least about pH 9.0, at least about pH 9.5, at least about pH 10.0, or at least about pH 10.5.

During the course of the transamination reactions, the pH of the reaction mixture may change. The pH of the reaction mixture may be maintained at a desired pH or within a desired pH range by the addition of an acid or a base during the course of the reaction. Alternatively, the pH may be controlled by using an aqueous solvent that comprises a buffer, Suitable buffers to maintain desired pH ranges are known in the art and include, for example, phosphate buffer, triethanolamine buffer, and the like. Combinations of buffering and acid or base addition may also be used. In some embodiments, the buffer is TEA (e.g., about 0.025 M to about 0.25 M TEA). In some embodiments of the process the suitable reaction conditions comprise a buffer solution of about 0.05 M borate to about 0.25 M borate, or about 0.1 M borate. In some embodiments, the reaction conditions comprise water as a suitable solvent with no buffer present.

In some embodiments, the process for preparing compound (2a) using an engineered transaminase polypeptide described are generally carried out in an aqueous co-solvent system comprising an organic solvent (e.g., ethanol, isopropanol (IPA), dimethyl sulfoxide (DMSO), ethyl acetate, butyl acetate, 1-octanol, heptane, octane, methyl t-butyl ether (MTBE), toluene, and the like), ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like). The organic solvent component of an aqueous co-solvent system may be miscible with the aqueous component, providing a single liquid phase, or may be partly miscible or immiscible with the aqueous component, providing two liquid phases. Exemplary aqueous co-solvent systems comprises water and one or more organic solvent. In general, an organic solvent component of an aqueous co-solvent system is selected such that it does not completely inactivate the transaminase enzyme. Appropriate co-solvent systems can be readily identified by measuring the enzymatic activity of the specified engineered transaminase enzyme with a defined substrate of interest in the candidate solvent system, utilizing an enzyme activity assay, such as those described herein. In some embodiments of the process, the suitable reaction conditions comprise an aqueous co-solvent comprising DMSO at a concentration of at least about 5% (v/v), at least about 10% (v/v), at least about 20% (v/v), at least about 30% (v/v), or at least about 40% (v/v).

The suitable reaction conditions used in the process can comprise a combination of reaction parameters that provide for the biocatalytic conversion of compound (1a) to compound (2a) in a higher diastereomeric ratio relative to compound (2c) and in a higher percentage conversion. Accordingly, in some embodiments of the process, the combination of reaction parameters comprises: (a) substrate loading of about 10-100 g/L compound (1a); (b) polypeptide concentration of about 1.0-20 g/L; (e) IPM concentration of about 0.1-10 M; (d) PLP cofactor at a concentration of about 0.1-1.0 g/L; (e) about pH 8.5-11.0; and (f) temperature of about 30-60° C. In some embodiments, the combination of reaction parameters comprises: (a) at least about 10 g/L compound (1a); (b) at least about 1 g/L polypeptide; (c) at least about 1 M isopropylamine; (d) at least about 1 g/L PLP; (e) about 0.2 M borate; (f) at least about 20% (v/v) DMSO; (g) about pH 10.5; and (h) a temperature of about 45° C.

The engineered transaminase polypeptides used in the present process have improved properties in the biocatalytic conversion of compound (1a) to compound (2a) and can provide increased yields of the product in higher diastereomeric ratio in a shorter time periods with a smaller amount of enzyme than the wild type polypeptide of SEQ ID NO: 2 or the engineered polypeptides SEQ ID NO: 4 or 6. Accordingly, in some embodiments of the method, the suitable reaction conditions comprise a substrate loading of compound (1a) of at least about 20 g/L, 30 g/L, 40 g/L, 50 g/L, 60 g/L, 70 g/L, 100 g/L, or more, and wherein the method results in at least about 90%, 91%, 92%, 93%, 94%, 95%, 96%, 97%, 98%, 99% or greater conversion of compound (1a) to compound (2a) in about 48 h or less, in about 36 h or less, or in about 24 h or less.

In some embodiments of the process, the suitable reaction conditions comprise a substrate loading of compound (1a) of at least about 20 g/L, 30 g/L, 40 g/L, 50 g/L, 60 g/L, 70 g/L, 100 g/L, or more, and the method results in the conversion of the racemic mixture of compound (1) to the product compound (2a) in a diastereomeric ratio relative to compound (2c) of at least about 2:1, at least about 3:1, at least about 4:1, at least about 8:1, at least about 10:1, at least about 15:1, at least about 20:1, or at least about 30:1, in about 48 h or less, in about 36 h or less, or in about 24 h or less. Further, in embodiments where the suitable reaction conditions suitable that allow for the epimerization of compound (1b) to compound (1a), the method can provide a dynamic kinetic resolution and the yield of product of compound (2a) formed by the reaction relative to the starting amount of the compound (1) is greater than 50%, greater than 60%, greater than 70%, greater than 80%, greater than 90%, greater than 95%, or more.

In carrying out the transamination reactions described in the process of the instant invention, the engineered transaminase polypeptide may be added to the reaction mixture in the form of a purified enzyme, whole cells transformed with gene(s) encoding the enzyme, and/or as cell extracts and/or lysates of such cells. Whole cells transformed with gene(s) encoding the engineered transaminase enzyme or cell extracts, lysates thereof, and isolated enzymes may be employed in a variety of different forms, including solid (e.g., lyophilized, spray-dried, and the like) or semisolid (e.g., a crude paste). The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like). In some embodiments where the engineered polypeptide can be expressed in the form of a secreted polypeptide and the culture medium containing the secreted polypeptides can be used in the method of converting compound (1a) to compound (2a).

In some embodiments, solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a pre-chilled lyophilization chamber, followed by the application of a vacuum.

In some embodiments, the order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor, transaminase, and transaminase substrate may be added first to the solvent. For improved mixing efficiency when an aqueous co-solvent system is used, the transaminase, and cofactor may be added and mixed into the aqueous phase first. The organic phase may then be added and mixed in, followed by addition of the transaminase substrate. Alternatively, the transaminase substrate may be premixed in the organic phase, prior to addition to the aqueous phase.

The quantities of reactants used in the transamination reaction will generally vary depending on the quantities of product desired, and concomitantly the amount of transaminase substrate employed. Those having ordinary skill in the art will readily understand how to vary these quantities to tailor them to the desired level of productivity and scale of production. In general, the transaminase substrates are kept at levels that achieve essentially complete or near complete conversion of the substrates into products. Generally, the transamination reaction is generally allowed to proceed until essentially complete, or near complete, transformation of substrate is obtained. Transformation of substrate to product can be monitored using known methods by detecting substrate and/or product. Suitable methods include gas chromatography, HPLC, and the like.

In some embodiments, the process can further comprise a step of removal of the carbonyl by-product formed from the amino group donor when the amino group is transferred to the substrate of compound (1a). Such removal in situ can reduce the rate of the reverse reaction such that the forward reaction dominates and more substrate is then converted to product. Removal of the carbonyl by-product can be carried in a number of ways. Where the amino group donor is an amino acid, such as alanine, the carbonyl by product, a keto acid, can be removed by reaction with a peroxide (see, e.g., US 2008/0213845, incorporated herein by reference). Peroxides which can be used include, among others, hydrogen peroxide; peroxyacids (peracids) such as peracetic acid ($CH_3CO_3H$), trifluoroperacetic acid and metachloroperoxybenzoic acid; organic peroxides such as t-butyl peroxide (($CH_3)_3COOH$), or other selective oxidants such as tetrapropylammonium perruthenate, $MnO_2$, $KMnO_4$, ruthenium tetroxide and related compounds. Alternatively, pyruvate removal can be achieved via its reduction to lactate by employing lactate dehydrogenase to shift equilibrium to the product amine (see, e.g., Koszelewski et al., 2008, Adv. Syn. Catal. 350: 2761-2766). Pyruvate removal can also be achieved via its decarboxylation to carbon dioxide acetaldehyde by employing pyruvate decarboxylase (see, e.g., Höhne et al., 2008, Chem BioChem 9: 363-365).

In some embodiments of the process, where the choice of the amino donor results in a carbonyl by-product that has a vapor pressure higher than water (e.g., a low boiling co-product such as a volatile organic carbonyl compound), the carbonyl by-product can be removed by sparging the reaction solution with a non-reactive gas or by applying a vacuum to lower the reaction pressure and removing the carbonyl by-product present in the gas phase. A non-reactive gas is any gas that does not react with the reaction components. Various non-reactive gases include nitrogen and noble gases (e.g., inert gases). In some embodiments, the non-reactive gas is nitrogen gas.

In some embodiments, the amino donor used in the process is isopropylamine (IPM), which forms the carbonyl by-product acetone upon transfer of the amino group to the amino group acceptor. The acetone can be removed by sparging with nitrogen gas or applying a vacuum to the reaction solution and removing the acetone from the gas phase by an acetone trap, such as a condenser or other cold trap. Alternatively, the acetone can be removed by reduction to isopropanol using a ketoreductase.

In some embodiments of the process where the carbonyl by-product is removed, the corresponding amino group donor can be added during the transamination reaction to replenish the amino group donor and/or maintain the pH of the reaction. Replenishing the amino group donor also shifts the equilibrium towards product formation, thereby increasing the conversion of substrate to product. Thus, in some embodiments wherein the amino group donor is IPM and the acetone product is removed in situ, the method can further comprise a step of adding IPM to the reaction solution to replenish the amino group donor lost during the acetone removal and to maintain the pH of the reaction (e.g., at about 8.5).

Alternatively, in embodiments where an amino acid is used as amino group donor, the keto acid carbonyl by-product can be recycled back to the amino acid by reaction with ammonia and NADH using an appropriate amino acid dehydrogenase enzyme, thereby replenishing the amino group donor.

In some embodiments, the process comprises the step of an enzymatic conversion of compound (1a) to compound (2a) using an engineered transaminase polypeptide can further comprise chemical steps of compound (2a) product work-up, extraction, isolation, purification, and/or crystallization, each of which can be carried out under a range of conditions.

In some embodiments, the present disclosure also contemplates that the process comprising the step of an enzymatic conversion of compound (1a) to compound (2a) using an engineered transaminase polypeptide can further comprise one or more further chemical steps for converting compound (2a) to the pharmaceutical ingredient of Compound A (IUPAC name: (3R)-1-[(1R,2R)-2-[2-(3,4-dimethoxyphenyl)ethoxy]cyclohexyl]pyrrolidin-3-ol), or its salts, hydrates, or solvates In some embodiments, the present process for the preparation of the compound (A) comprises contacting (R)-2-(3,4-dimethoxyphenethoxy)cyclohexanone with a transaminase polypeptide described herein in the presence of an amino donor under reaction conditions suitable for conversion of the (R)-2-(3,4-dimethoxyphenethoxy)cyclohexanone to (1R,2R)-2-(3,4-dimethoxyphenethoxy)cyclohexanamine in enantiomeric and diastereomeric excess. Any of the conditions described above can be used in the step of the process.

In some embodiments, the conversion of compound (1a) to compound (2a) can be carried out wherein the method comprises contacting an analog of compound (1a) with an engineered transaminase polypeptide (e.g., as described in Tables 2A, 2B, 2C and 2D and elsewhere herein) in the presence of an amino donor under suitable reaction conditions, thereby resulting in the preparation of the chiral amine of the corresponding analog of product compound (2a) in diastereomeric excess. Suitable reactions conditions for the conversion of analogs of compound (1a) to the chiral amine of the corresponding analogs of compound (2a) can be the same as used for compound (1a) or determined by the ordinary artisan based on the known properties of the analog compounds and routine experimentation.

Some abbreviations that may be used herein include:
Ac Acyl (CH$_3$C(O)—)
ACN Acetonitrile
Aq. Aqueous
Bn Benzyl
C. Celsius
calc. Calculated
DCM dichloromethane
DIPEA N,N-diisopropylethylamine
DMAc N,N-dimethylacetamide
DMF N,N-dimethylformamide
DMSO Dimethyl Sulfoxide
equiv. Equivalent(s)
Et ethyl
EtOAc Ethyl acetate
h Hour(s)
HMDS Hexamethyldisilazane
HPLC High performance liquid chromatography
IPA Isopropyl Alcohol
IPAC Isopropyl Acetate
IPM Isopropylamine
LCAP Liquid Chromatography Area Percent
MeCN Acetonitrile
mp Melting point
MS Mass Spectrum
MTBE Methyl tert-butyl ether
Ph Phenyl
Prep. Preparative
r.t. (or rt or RT) Room temperature
TEA Triethyl amine
TFA Trifluoroacetic acid
THF Tetrahydrofuran
TLC Thin layer chromatography Outline of Method of Preparation of Compounds of the Invention The aminocyclohexyl ether compounds of the present invention contain amino and ether functional groups disposed in a 1,2 arrangement on a cyclohexane ring. Accordingly, the amino and ether functional groups may be disposed in either a cis or trans relationship, relative to one another and the plane of the cyclohexane ring as shown on the page in a two dimensional representation.

The present invention provides synthetic methodology for the preparation of the aminocyclohexyl ether compounds according to the present invention as described herein. The aminocyclohexyl ether compounds described herein may be prepared from aminoalcohols and alcohols by following the general methods described below, and as illustrated in the examples. Some general synthetic processes for aminocyclohexyl ethers have been described in WO 99/50225 and references cited therein.

The invention is illustrated in the following generic schemes and the examples in the Experimental Details Section that follows. The substituents and integers used in the follow schemes are as defined in the embodiments of the instant invention, unless otherwise indicated. This section is set forth to aid in an understanding of the invention but is not intended to, and should not be construed to limit in any way the invention as set forth in the claims which follow thereafter.

SCHEME 1
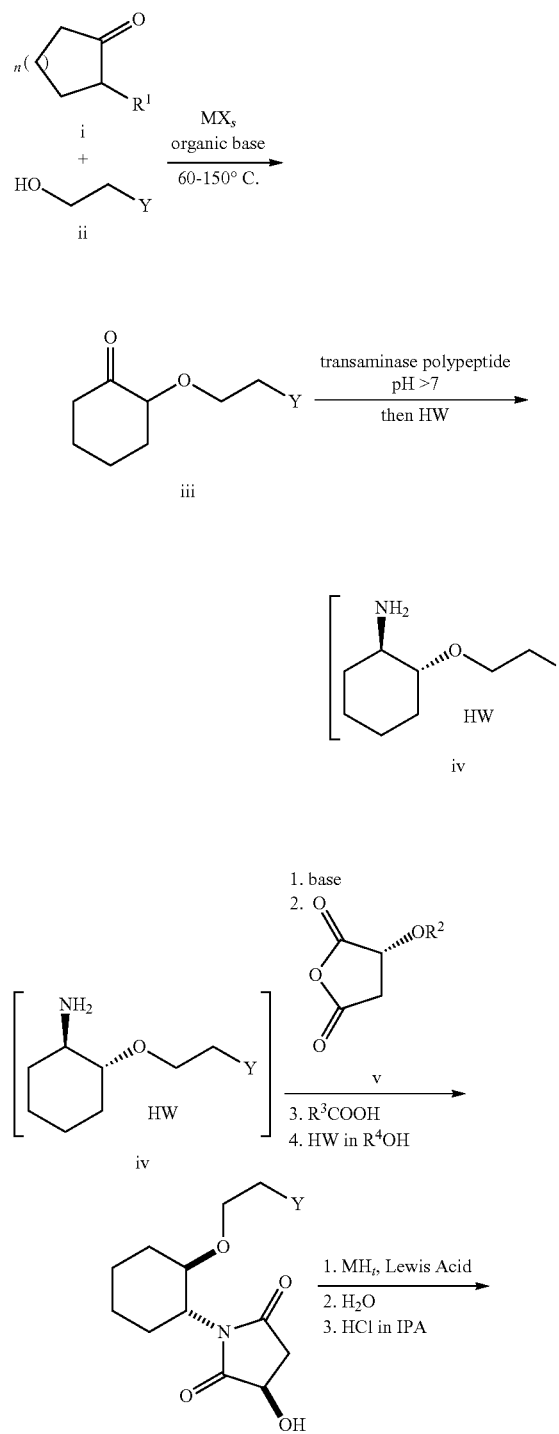
HW represents an acid, where W may be selected from a halide, sulfonate, malate, maleate, oxalate, and other carboxylates, phosphate, perchlorate and the like.
SCHEME 2
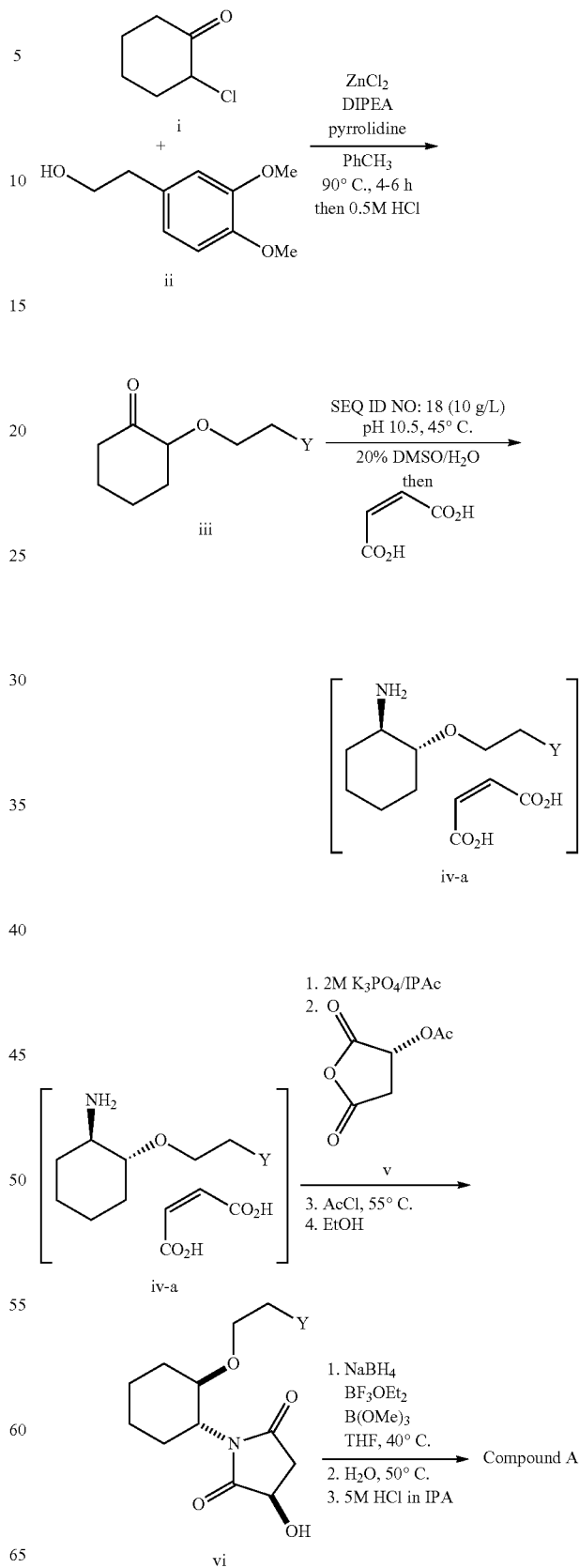

SCHEME 2A

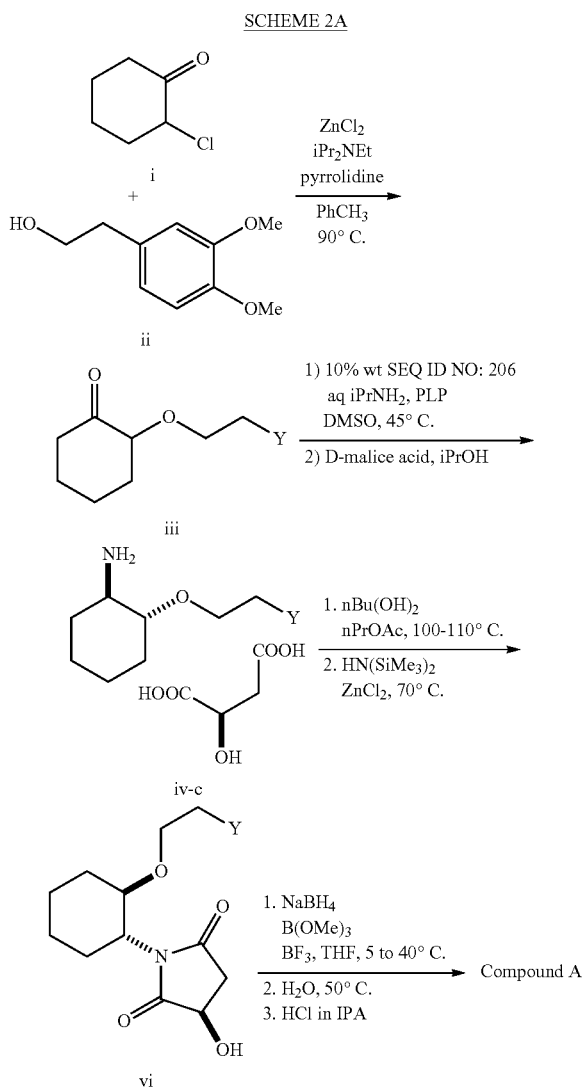

Experimental Details Section

The compounds of the present invention were prepared by the general methods outlined in the synthetic schemes above.

EXAMPLE A

Synthesis, Optimization, and Screening of Engineered Transaminase Polypeptides

A. Gene synthesis and optimization: The polynucleotide sequence encoding the reported wild-type omega transaminase polypeptide from *Arthrobacter* sp. KNK168 of SEQ ID NO: 2 with a single amino acid change (I306V) was codon optimized and synthesized as the gene of SEQ ID NO: 3. The synthetic gene of SEQ ID NO: 3 was cloned into a pCK110900 vector system (see e.g., US Patent Application Publication 20060195947, which is hereby incorporated by reference herein) and subsequently expressed in *E. coli* W3110fhuA. The *E. coli* W3110 expresses the transaminase polypeptides as an intracellular protein under the control of the lac promoter. The polypeptide accumulates primarily as a soluble cytosolic active enzyme. HTP assays used for primary screening were carried out using the cleared cell-lysate from expression of these *E. coli* W3110 cells (see below). The synthetic gene of SEQ ID NO: 3 was optimized for increased expression and thermostability by inserting active and silent mutations which are described in U.S. application Ser. No. 12/714,397, filed Feb. 26, 2010, which is incorporated herein by reference. This optimization resulted in the synthetic gene of SEQ ID NO: 5 encoding the engineered polypeptide of SEQ ID NO: 6, which has the following 24 amino acid differences relative to the naturally occurring transaminase of *Arthrobacter* sp. KNK168 (SEQ ID NO: 2): S8P; Y60F; L61Y; H62T; V65A; V69T; D81G; M94I; I96L; F122I; G136F; A169L; V199I; A209L; G215C; G217N; S223P; L269P; L273Y; T282S; A284G; P297S; I306V; and S321P.

The engineered polypeptide of SEQ ID NO: 6 was used as the starting backbone for further optimization to generate genes encoding the engineered transaminase polypeptides of SEQ ID NOs: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, and 206, each of which is capable of converting compound (1a) to compound (2a) with improved enzyme properties relative to it and/or the reference polypeptides SEQ ID NOs: 6. Further optimization of the gene of SEQ ID NO: 5 was carried out using the standard methods of directed evolution via iterative variant library generation by gene synthesis followed by screening and sequencing of hits.

B. Production of shake flask powders (SFP): A shake-flask procedure was used to generate engineered transaminase polypeptide powders used in secondary screening assays or in the biocatalytic methods of converting compound (1a) to compound (2a) disclosed herein. Shake flask powder (SFP) include approximately 30% total protein and accordingly provide a more purified preparation of an engineered enzyme as compared to the cell lysate used in HTP assays. A single microbial colony of *E. coli* containing a plasmid encoding an engineered transaminase of interest is inoculated into 50 mL Luria Bertani broth containing 30 μg/ml chloramphenicol and 1% glucose. Cells are grown overnight (at least 16 hours) in an incubator at 30° C. with shaking at 250 rpm. The culture is diluted into 250 mL Terrific Broth (12 g/L bacto-tryptone, 24 g/L yeast extract, 4 mL/L glycerol, 65 mM potassium phosphate, pH 7.0, 1 mM MgSO$_4$) containing 30 μg/ml chloramphenicol, in a 1 liter flask to an optical density at 600 nm (OD600) of 0.2 and allowed to grow at 30° C. Expression of the transaminase gene is induced by addition of isopropyl-β-D-thiogalactoside ("IPTG") to a final concentration of 1 mM when the OD600 of the culture is 0.6 to 0.8 and incubation is then continued overnight (at least 16 hours). Cells are harvested by centrifugation (5000 rpm, 15 min, 4° C.) and the supernatant discarded. The cell pellet is resuspended with an equal volume of cold (4° C.) 100 mM triethanolamine (chloride) buffer, pH 7.0 (optionally including 2 mM MgSO$_4$), and harvested by centrifugation as above. The washed cells are resuspended in two volumes of the cold triethanolamine (chloride) buffer and passed through a French Press twice at 12,000 psi while maintained at 4° C. Cell debris is removed by centrifugation (9000 rpm, 45 minutes, 4° C.). The clear lysate supernatant was collected and stored at −20° C. Lyophilization of frozen clear lysate provides a dry shake-flask powder of crude transaminase polypeptide. Alternatively, the cell pellet (before or after washing) can be stored at 4° C. or −80° C.

C. HTP Assay: Primary screening used to guide optimization was carried out in a ~200 μL at volume in 96-well plate high-throughput (HTP) assay protocol using cell lysates. For the HTP assay data provided in Table 2B, the general HTP assay conditions were: 50 g/L substrate mixture of compound (1), 40 μL of clear cell lysate containing the engineered transaminase polypeptide, 1 g/L PLP, 1 M IPM, in an aqueous co-solvent solution of 0.2 M borate buffer, 40% (v/v) DMSO, pH 10.5, 45° C. reaction temperature and 4 h reaction time (with 200 rpm shaking).

The details of the HTP assay protocol are as follows. The stock assay solution was prepared by mixing the following: 4.00 mL of 5 M isopropylamine (IPM) in 0.2 M boric acid; 2.00 mL of 10 g/L PLP in sterile water; 7.00 mL of DMSO; and 2.00 mL of 0.2 M boric acid. This stock assay solution was adjusted to pH 10.5 (with concentrated HCl or 10 M NaOH) upon stirring and 150 μL/well of the solution were dispensed into a 96 deep well plate. The plate was heat sealed and incubated at 45° C. while shaking (200 rpm) for at least 15 minutes. Clear cell lysate containing the engineered polypeptide variant to be screened was prepared by shaking cells in 0.5 mg/mL Lysozyme, 0.4 mg/mL PMBS, 0.2 M borate, pH 10.5, for 1 h at room temperature, followed by centrifugation at 5000 rpm and 4° C. for 10 min. A 40 μL volume of the clear cell lysate (taken from a total 300 μL/well volume of lysate) was then added to each well containing the 150 μL of the stock assay solution. A substrate stock solution was prepared in DMSO as follows: 28.7 g/L of 87 wt % racemic substrate mixture of compound (1) dissolved in 25 mL DMSO along with 2.5 g of biphenyl to provide a final solution volume of 52 mL. The HTP assay reaction was then initiated by the addition of 21 μL/well of the substrate stock solution to the plate, which then was heat sealed and shaken (200 rpm) at 45° C. for 4 h. After 4 h, the reaction was quenched by addition of 800 μL/well of MeOH followed by heat sealing and a quick further shaking to ensure homogeneity. After centrifugation, a 20 μL/well sample was diluted into 180 μL/well of MeOH for achiral HPLC analysis as described below.

For the HTP assay data provided in Table 2A, the HTP assays were carried out as above but with the following slightly modified general reaction conditions: 5 g/L of a racemic substrate mixture of compound (1), 100 μL clear cell lysate containing the engineered transaminase polypeptide, 1 M isopropylamine (IPM), 1 mM PLP, 100 mM TEA, pH 10.0, 45° C. and 2 h reaction time with 245 rpm shaking. Cells were lysed by shaking for 0.5 to 1 hour at 250 rpm and 37° C. in 1 mL of lysis buffer containing 100 mM triethanolamine, 0.5 g/L lysozyme, and 0.4 g/L polymyxin B sulfate at pH 9.0. Rather than quenching with MeOH, a 50 μL aliquot was removed and added to 100 μL acetonitrile, and 10 μl, of this is injected onto an achiral HPLC column for analysis as described below.

D. SFP Assay: In addition to the HTP assay for primary screening, in some cases a secondary screening was carried out on a 2.00 mL scale using shake-flask powder (SFP) preparations of the engineered transaminase polypeptides. The general SFP assay reaction conditions (specific conditions are noted in Tables 2A and 2B), were as follows: 10 g/L or 100 g/L substrate mixture of compound (1), 1.0 g/L of the engineered transaminase polypeptide SFP, 1.0 g/L PLP, 1 M IPM, in an aqueous co-solvent solution of 0.2 M borate buffer or 0.1 M TEA buffer, 20% or 40% (v/v) DMSO (as noted in Tables 2A and 2B), pH 10.0 or pH 10.5, 45° C. reaction temperature and 4.5 h, 15-18 h, or 24 h reaction time (with 400 rpm shaking). The details of the SFP assay protocol are as follows.

The stock assay solution was prepared as follows: to 4.00 mL of 5M IPM in 0.2 M boric acid (pH not adjusted) was added 2.00 mL of 10 g/L PLP in sterile water followed by 6.00 mL of DMSO and 4.00 mL of 0.2 M boric acid (pH not adjusted). The stock assay solution was then adjusted to pH 10.5 using concentrated HCl. For each experiment 1.60 mL of stock assay solution was added into a screw cap vial, which was then tightly closed and heated to 45° C. with magnetic stirring (400 rpm). Stock enzyme solution was prepared by dissolving 20 mg of engineered polypeptide SFP in 2.00 mL of 0.2 M borate, pH 10.5 buffer (0.2 M boric acid solution adjusted to pH 10.5 using 10M NaOH). After 15 min, 200 μL of a 10.0 g/L enzyme stock solution was added to the reaction mixture at 45° C. Immediately after addition of the enzyme stock solution, 420 μL of a substrate stock solution was then added to start the reaction (substrate stock solution: 28.7 g/L of 87 wt % racemic substrate mixture of compound (1) in 25 mL DMSO with 2.5 g of biphenyl to provide a final volume of 52 mL). The vial was tightly closed and the reaction was left to proceed upon stirring (400 rpm) at 45° C. for 48 h with the 24 h time point used for comparison of SEP assay results. The course of the SEP assay reaction was monitored over the 48 h time course by taking 5 μL samples, diluting in 1.00 mL of MeOH, and then directly injecting into the HPLC for analysis.

E. HPLC analysis of assay samples: After running the HTP or SFP assays, as described above, samples from the quenched assay reaction solutions were analyzed using achiral HPLC to determine the conversion of the racemic mixture of compound (1) to the product of compound (2a), and/or to determine the diastereomeric ratio of the products. Additionally, SEP assay samples were analyzed using chiral HPLC to confirm that the engineered polypeptides were producing >99% e.e. of the R-amine products (i.e., compound (2a) and compound (2c)) relative to the S-amine products.

Analysis of the HTP assay reaction samples to provide results for trans:cis ratio and % conversion as summarized in Table 2A were carried using achiral HPLC on either a Phenomenex Luna C18 or an Ascentis C18 column. Samples were prepared as follows: after reaction remove 50 μL aliquot and add to 100 μL of acetonitrile in a shallow well plate; centrifuge plate at 4000 rpm for 10 min; inject 10 μL into HPLC. The HPLC conditions and instrumental parameters are shown below in Tables 3 and 4.

TABLE 3

Achiral HPLC on Phenomenex Luna C18 column

Column: Phenomenex Luna C18(2), 10 cm × 4.6 mm, 5 μm, cat 00D-4252-E0
Flow rate: 2.0 mL/min
Column temp: 40° C.
Solvents A: 0.1% TFA in DI water; B: neat MeCN
Solvent program:

| Step | Time | Module | Action | Value |
|---|---|---|---|---|
| 1 | 0.01 | Pumps | Pump B Conc. | 25.0 |
| 2 | 1.10 | Pumps | Pump B Conc. | 25.0 |
| 3 | 1.35 | Pumps | Pump B Conc. | 100.0 |
| 4 | 2.25 | Pumps | Pump B Conc. | 100.0 |
| 5 | 2.26 | Pumps | Pump B Conc. | 25.0 |
| 6 | 2.70 | Controller | Stop | |

Total program time: 2.7 min
Detector wavelength: 275 nm
Retention times: trans isomer = 1.8 min; cis isomer = 2.2 min; ketone substrate = 2.4 min

TABLE 4

Achiral HPLC on Ascentis Express C18 column

Column: Ascentis Express C18, 15 cm × 4.6 mm, 2.7 μm, cat 53829-U
Flow rate: 1.0 mL/min
Column temp: 40° C.
Solvents A: 20 mM NH$_4$OAc in DI water; B: neat MeCN
Solvent program:

| Step | Time | Module | Action | Value |
|---|---|---|---|---|
| 1 | 0.01 | Pumps | Pump B Conc. | 30.0 |
| 2 | 1.00 | Pumps | Pump B Conc. | 30.0 |
| 3 | 2.50 | Pumps | Pump B Conc. | 100.0 |
| 4 | 3.00 | Pumps | Pump B Conc. | 100.0 |
| 5 | 3.01 | Pumps | Pump B Conc. | 30.0 |
| 6 | 4.75 | Controller | Stop | |

Total program time: 4.75 min
Detector wavelength: 275 nm
Retention times: trans isomer = 3.2 min; cis isomer = 3.3 min; ketone substrate = 4.3 min Analysis of the HTP assay reaction samples to provide results for trans: cis ratio as summarized in Table 2B were carried out using achiral HPLC on a Zorbax SB-C18 column according to the conditions and instrumental parameters shown in Table 5.

TABLE 5

Achiral HPLC on Zorbax SB-C18 for HTP Assay

Column: Zorbax SB-C18 (75 × 4, 6 mm, 3.5 μm)
Flow rate: 1.5 mL/min
Column temp: 30° C.
Solvents A: 85% MeOH, 15% DI Water, 0.05% Diethylamine
Solvent program: isocratic
Total program time: 1.40 min
Detector wavelength: 280 nm
Retention times: ketone substrate = 0.7 min; trans isomer = 0.8 min; cis isomer = 1.0 min Analysis of the HTP assay reaction samples to provide results for % conversion used to determine relative activity as summarized in Table 2B were carried out using achiral HPLC on an Ascentis Express C18 column according to the conditions and instrumental parameters shown in Table 6.

TABLE 6

Achiral HPLC on Ascentis Express C18 column for SFP testing

Column: Ascentis express C18 (100 × 4.6, 2.7 um)
Flow rate: see program
Column temp: 25° C.
Solvents A: 0.05% H$_3$PO$_4$ (pH = 2.25) in DI water; B: neat MeCN
Program:

| Step | Time | Module | Action | Value | Action | Value |
|---|---|---|---|---|---|---|
| 1 | 0.01 | Pumps | Pump B Conc. | 25.0 | Flow rate | 1.6 mL/min |
| 2 | 2.00 | Pumps | Pump B Conc. | 36.0 | Flow rate | 1.6 mL/min |
| 3 | 2.05 | Pumps | Pump B Conc. | 50.0 | Flow rate | 2.0 mL/min |
| 4 | 4.00 | Pumps | Pump B Conc. | 50.0 | Flow rate | 2.0 mL/min |
| 5 | 4.05 | Pumps | Pump B Conc. | 100.0 | Flow rate | 2.0 mL/min |
| 6 | 5.50 | Pumps | Pump B Conc. | 100.0 | Flow rate | 2.0 mL/min |
| 7 | 5.51 | Pumps | Pump B Conc. | 25.0 | Flow rate | 1.6 mL/min |
| 8 | 6.5 | Controller | Stop | | | |

Total program time: 6.5 min
Detector wavelength: 280 nm
Retention times: trans isomer = 1.2 min; cis isomer = 1.4 min; ketone substrate = 3.6 min Additionally, as noted in Table 2A, the production of the R-amine products relative to S-amine products in enantiomeric excess of 99% e.e. was confirmed using chiral HPLC analysis of polypeptide SEP assay samples from the following engineered polypeptides: SEQ ID NO: 6, 8, 12, 16, 18, 40, 42, 44, 46, 48, 50, 52, 58, 66, and 82. Chiral HPLC was carried out according to the following sample derivatization protocol and using a Diacel Chiralcel OT-RH column according to the conditions and instrumental parameters shown in Table 7.

F. Derivitization: SFP assay samples were transferred to vials. Saturated potassium carbonate (200 μL) was added followed by ethyl acetate (1 mL). The vials were vortexed, and the phases were allowed to separate. The organic layer (700 μL) was transferred to a fresh vial and evaporated under nitrogen purge (removes any extracted isopropylamine). To each vial was added 100 mL of derivatizing solution (5 mL ethyl acetate+250 μL triethylamine+125 μL acetic anhydride). After 5 to 10 min of reaction, the solution was evaporated under nitrogen purge, and 200 μL acetonitrile was added to resuspend the sample.

TABLE 7

Chiral HPLC on Diacel Chiralcel OJ-RH column

Column: Diacel Chiralcel OJ-RH, 150 mm × 4.6 mm, 5 μm
Temp: 40° C.
Flow rate: 1.5 ml/min
Solvents: A: 0.1% H$_3$PO$_4$ in DI water
B: neat MeCN
Solvent program

| Step | Time | Module | Action | Value |
|---|---|---|---|---|
| 1 | 0.01 | Pumps | Pump B Conc. | 20.0 |
| 2 | 10.00 | Pumps | Pump B Conc. | 20.0 |
| 3 | 12.00 | Pumps | Pump B Conc. | 70.0 |
| 4 | 14.00 | Pumps | Pump B Conc. | 70.0 |
| 5 | 16.00 | Pumps | Pump B Conc. | 20.0 |
| 6 | 20.00 | Controller | Stop | |

Total program time: 20 min
Detector wavelength: 275 nm
Retention times: (R)-trans isomer = 6.0 min; (S)-trans isomer = 6.5 min; (R)-cis isomer = 12.4 min; (S)-cis isomer = 13.4 min.

EXAMPLE 1

Preparation of Alkoxy Ketone iii

To a solution of dimethoxyphenyl ethanol ii (250 g, 1.37 mol), zinc chloride (224 g, 1.2 equiv), diisopropylethylamine (358 mL, 1.5 equiv), and pyrrolidine (34.0 mL, 0.3 equiv) in toluene (1.25 L, 5 vol) at 90° C. was added chlorocyclohexanone i (220 mL, 1.4 equiv) at a controlled rate over 2 hours. The resulting biphasic mixture was maintained at 90° C. for an additional 2 hours, at which time 97% conversion was observed by HPLC. The biphasic mixture was then allowed to cool to 70° C.), and 1.0 M aqueous hydrochloric acid (2.5 L, 10 vol) was added. The mixture was allowed to cool to 32° C., after which the lower aqueous phase was removed. The upper organic phase was concentrated at 40° C./5 mmHg until the toluene content was below 10 wt %. The resulting oil was used in the next step without further purification. The assay yield of the alkoxy ketone was 92%.

EXAMPLE 2

Preparation of Cyclohexyl Amine Maleate Salt (iv-a)

The transaminase polypeptide (SEQ ID NO: 18) (8 g, 20 wt % relative to alkoxy ketone iii) and pyridoxal phosphate (800 mg, 2 wt %) were charged to 2000 mL RB flask. Borate buffer (0.2 M, 640 mL, 16 vol) with 1M iPrNH$_2$ at pH 10.5 was added. The slurry was stirred at ambient temperature (20-25° C.) with a magnetic stir bar, to allow as much transaminase polypeptide to dissolve as possible. Dimethyl sulfoxide (80 mL, 2 vol) was added, and the resulting slurry was heated to 45° C. Once at 45° C., the pH of the slurry was adjusted to exactly 10.5 using 4 M isopropyl amine and a free standing titrating unit.

Alkoxy ketone iii (40.0 g, 142 mmol) was dissolved in dimethyl sulfoxide (80 mL, 2 vol). The alkoxy ketone solution was added to the hot transaminase polypeptide slurry at a controlled rate over 30 minutes. The resulting milky yellow slurry was aged 16 hours with the pH controlled at 10.5 by addition of isopropyl amine.

The reaction solution was sampled and examined by HPLC. 90% conversion was observed. The reaction solution was aged another 5 hours at 45° C. without pH control. The reaction was sampled and examined by HPLC to have >94% conversion. The mixture was then allowed to cool to ambient temperature, after which the slurry was extracted three times with 1:1 isopropanol:tert-butyl methyl ether (800 mL/20 vol for each extraction). The lower aqueous phase was discarded. The combined organic extracts were concentrated to a low volume at 30-40° C./5-25 mmHg. The resulting mixture was diluted with tert-butyl methyl ether (400 mL, 10 vol) then washed with 1 M potassium carbonate that had been saturated with potassium chloride (400 mL, 10 vol). The lower aqueous phase was discarded.

The upper organic layer was solvent switched to 2-butanol. The resulting solution was filtered through CELITE (diatomaceous earth), then diluted with 2-butanol to a total volume of 125 mL (3.125 vol relative to starting alkoxy ketone) and cooled below 5° C. A solution of maleic acid (13.2 g) in 2-butanol (120 mL, 3 vol) was added at a controlled rate over 1 hour below 5° C. When half of the maleic acid solution had been added, the mixture was seeded with cyclohexyl amine maleate salt iv-a (400 mg, 1 wt %). After complete addition of the maleic acid solution, the slurry was allowed to warm to ambient temperature. tert-Butyl methyl ether (60 mL) was added at a controlled rate over 1 hour, after which the slurry was aged at ambient temperature for an additional 3 hours. The crystalline product was then collected by filtration. The filter cake was washed twice with tert-butyl methyl ether (60 mL), after which the cake was dried under nitrogen flow-through. The cyclohexyl amine maleate salt iv-a (40.4 g, 71% yield) was obtained as an off-white powder.

EXAMPLE 3

Preparation of Hydroxy Succinimide vi

A suspension of R-Malic acid (100 g) in acetyl chloride (265 mL, 5 equiv) was heated to 50° C. under nitrogen for 16 h or until >95% conversion to the anhydride was observed by GC. At this point, the volatiles were distilled off. The resulting oil was dissolved in iPrOAc (200 mL), filtered. The filtrate was concentrated, dissolved in iPrOAc (290 mL). MTBE (750 mL) was slowly added to induce crystallization of the R-acetoxy malic acid anhydride (v). After cooling to 0° C. in an ice bath, the slurry was filtered and dried under N$_2$/vacuum sweep to give 95 g (80% yield) of the R-acetoxy malic acid anhydride(v) as a colorless, crystalline solid.

The maleate salt iv-a (20 g) was added to a vigorously stirred mixture of isopropyl acetate (iPrOAc, 100 mL) and aqueous 2M potassium phosphate (K$_3$PO$_4$, 100 mL). The lower aqueous layer was discarded. The organic layer was washed with 15% brine (100 mL) and concentrated. The residue was dissolved in iPrOAc (141 mL) and R-acetoxy malic acid anhydride (v) (8.8 g, 1.1 equiv) was added. The resulting mixture was stirred at 55° C. until >95% conversion to the malic acid amide was observed by HPLC (typically 1-3 h).

To this slurry of malic acid amide in IPAc was then added acetyl chloride (36 mL, 10 equiv) and the resulting mixture was heated at 55° C. until greater than 95% conversion to the acetoxy succinimide was observed by HPLC (typically 5 h). The resulting solution was then cooled back to 0° C. for addition of ethanol (141 mL) before heated back to 55° C. The mixture was aged until greater than 95% conversion to the hydroxy succinimide (vi) was observed by HPLC (typically 6-24 h). The solution was again cooled to 0° C. for addition of aqueous 1M solution of K$_2$CO$_3$ (400 mL). The organic layer was concentrated, the residue was combined with ethanol (38 mL), heated to 70° C., and crystallized by cooling to 5° C. to provide 16.2 g (84% yield) of vi from iv-a.

[Alternatively, maleate salt iv-a (5.0 g) was added to a vigorously stirred mixture of isopropyl acetate (iPrOAc, 25 mL) and aqueous 2M potassium phosphate (K$_3$PO$_4$, 25 mL). The organic layer was washed with 15% brine (25 mL) and concentrated. The residue was dissolved in iPrOAc (25 mL) and R-acetoxy malic acid anhydride (v) (2.2 g, 1.1 equiv) was added. The resulting mixture was stirred at ambient temperature until >95% conversion to the malic acid amide was observed by HPLC (typically 1-3 days). To the slurry of malic acid amide in IPAc was added thionyl chloride (SOCl$_2$, 1.3 mL, 1.4 equiv) and the mixture was stirred at ambient temperature until greater than 95% conversion to the acetoxy succinimide was observed by HPLC (typically for 5-24 h). The resulting solution was then combined with ethanol (25 mL) and concentrated sulfuric acid (H$_2$SO$_4$, 2.0 mL, 3 equiv) and aged at ambient temperature until greater than 95% conversion to the hydroxy succinimide (vi) was observed by HPLC (typically 25 h). The solution was cooled to 0° C. for addition water (10 mL) and 10 M aqueous solution of sodium hydroxide (10 mL) to neutral pH. The organic layer was washed with 15% brine (30 mL) and concentrated with toluene to a low volume (approximately 25 mL) for crystallization to give 3.7 g (77% isolated yield) of vi from iv-a.]

EXAMPLE 4

Preparation of the HCl Salt of Compound A

To a mixture of hydroxy succinimide vi (5 g) and sodium borohydride (1.5 g, 3 equiv) in tetrahydrofuran (THF, 25 mL)

at C was slowly added trimethylborate (B(OMe)$_3$, 1.5 mL, 1 equiv) over 5 min. After stirring at ambient temperature for 1.5 h, boron trifluoride etherate (BF$_3$OEt$_2$, 6.5 mL, 4 equiv) was added over 1 h at 0° C. This slurry was aged at ambient temperature for 4 h prior to heating at 40° C. until >95% complete reaction was observed by HPLC (typically 12-24 h). The resulting slurry was then cooled to 0° C. for addition of water (5 mL/g with respect to yl). This solution was then heated at 50° C. until >98% conversion to Compound A was observed by HPLC (typically 12-24 h). The resulting solution was then diluted with iPrOAc and aqueous sodium hydroxide to pH of approximately 10. The aqueous layer was discarded and the organic layer was washed with 15% brine followed by a small amount of water and concentrated to a low volume for crystallization. To this iPrOAc solution of Compound A was added iPrOH followed by HCl in iPrOH. The resulting slurry was aged at room temperature overnight, cooled to 0° C. and then filtered to give the HCl salt of Compound A in 85-90% yield.

EXAMPLE 5

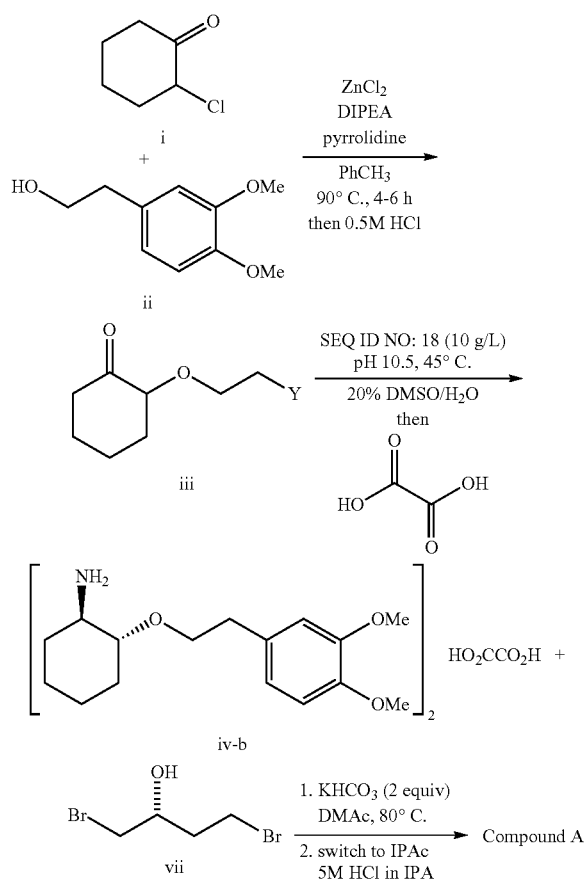

A. Preparation of Cyclohexyl Amine Oxalate Salt (iv-b)

The transaminase polypeptide (SEQ ID NO: 18) (2.66 g, 20 wt % relative to alkoxy ketone iii) and pyridoxal phosphate (267 mg, 2 wt %) were charged to 1000 mL RB flask. Borate buffer (0.2 M, 212 mL, 16 vol) with 1M iPrNH$_2$ at pH 10.5 was added. The slurry was stirred at ambient temperature (20-25° C.) with a magnetic stir bar, to allow as much transaminase polypeptide to dissolve as possible. Dimethyl sulfoxide (25 mL, 2 vol) was added, and the resulting slurry was heated to 45° C. Once at 45° C., the pH of the slurry was adjusted to exactly 10.5 using 4 M isopropyl amine and a free standing titrating unit.

Alkoxy ketone iii, as described in Example 1, (13.3 g, 47.7 mmol) was dissolved in dimethyl sulfoxide (25 mL, 2 vol). The alkoxy ketone solution was added to the hot transaminase polypeptide slurry at a controlled rate over 30 minutes. The resulting milky yellow slurry was aged 16 hours with the pH controlled at 10.5 by addition of isopropyl amine.

The reaction solution was sampled and examined by HPLC. 90% conversion was observed. The reaction solution was aged another 5 hours at 45° C. without pH control. The reaction was sampled and examined by HPLC to have >94% conversion. The mixture was then allowed to cool to ambient temperature, after which the slurry was extracted three times with 1:1 isopropanol:tert-butyl methyl ether (250 mL/20 vol for each extraction). The lower aqueous phase was discarded. The combined organic extracts were concentrated to a low volume at 30-40° C./5-25 mmHg. The resulting mixture was diluted with tert-butyl methyl ether (140 mL, 10 vol) then washed with 1 M potassium carbonate that had been saturated with potassium chloride (140 mL, 10 vol). The lower aqueous phase was discarded.

The upper organic layer was solvent switched to 100 mL IPA. The resulting solution was filtered through CELITE (diatomaceous earth) and cooled below 5° C. A solution of oxalic acid (1.27 g, 0.46 equiv) in IPA (10 mL, 1 vol) was added at a controlled rate over 1 hour below 5° C. When half of the oxalic acid solution had been added, the mixture was seeded with cyclohexyl amine oxalate salt iv-b (50 mg, 1 wt %). After complete addition of the oxalic acid solution, the slurry was allowed to warm to ambient temperature. The crystalline product was then collected by filtration. The filter cake was washed twice with tert-butyl methyl ether (20 mL), after which the cake was dried under nitrogen flow-through. The cyclohexyl amine oxalate salt iv-b (8.5 g, 85% yield) was obtained as a white powder.

B. Preparation of the HCl Salt of Compound A

To a slurry of potassium bicarbonate g, 4.0 equiv) in N,N-dimethylacetamide (DMAc, 10 mL) was added the cyclohexyl amine oxalate salt iv-b (811 mg, 1.25 mmol, 0.5 equiv). The resulting suspension was stirred at RT for 1 h before addition of the (R)-1,4-dibromo-butan-2-ol vii (580 mg, 1 equiv). The suspension was then heated to 80° C. for 12 h or until >98% conversion to Compound A was observed by HPLC. The suspension was then allowed to cool to RT and was diluted 20 mL IPAc, and 20 mL of saturated sodium bicarbonate was added. The aqueous layer was separated and extracted a second time with 20 mL IPAc. The aqueous layer was then discarded and the combined organic layers were concentrated to a low volume. To this concentrated IPAc solution of Compound A was added iPrOH followed by HCl in iPrOH. The resulting slurry was aged at room temperature overnight, cooled to C and then filtered to give the HCl salt of Compound A in 50-60% yield.

EXAMPLE 6

Step —A

Preparation of the Crystalline Amine D-Malate Salt

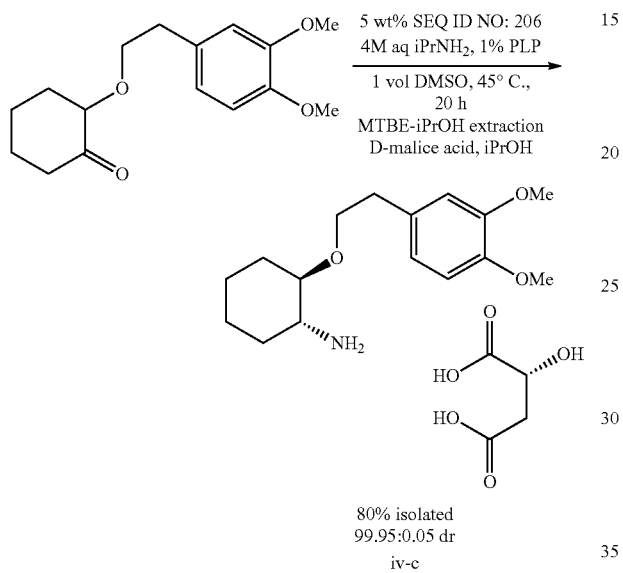

The transaminase polypeptide SEQ ID NO: 206 (1.25 g, 5 wt % relative to alkoxy ketone) and pyridoxal 5'-phosphate (250 mg, 1 wt %) were charged to a 3-neck RB flask. Borate buffer (0.2 M, 225 mL, 9 vol) with 1M iPrNH$_2$ at pH 10.5 was added. Dimethyl sulfoxide (12.5 mL, 0.5 vol) was added, and the resulting slurry was heated to 45° C. in a closed system. Once at 45° C., the pH of the slurry was adjusted to 10.5 using 4 M isopropylamine and a free standing titrating unit.

Alkoxyketone, which was prepared as described in Example 1, (26.6 g, 89 wt %, 85 mmol) was dissolved in dimethyl sulfoxide (12.5 mL, 0.5 vol). The alkoxy ketone solution was added to the hot transaminase polypeptide slurry over 3 minutes. The resulting milky yellow slurry was aged 20 h while the pH was maintained at 10.5 by addition of isopropylamine (95% conversion by HPLC).

The mixture was then allowed to cool to ambient temperature, after which the slurry was extracted with a mixture of 107 mL tert-butyl methyl ether and 80 mL isopropanol. The aqueous phase was extracted with a mixture of 80 mL tert-butyl methyl ether and 53 mL isopropanol followed by the third extraction using 80 mL tert-butyl methyl ether and 40 mL isopropanol. The combined organic extracts (83% assay, 99.2:0.8 dr) were concentrated, diluted with isopropyl acetate (133 mL) and washed with 1 M K$_3$PO$_4$/KCl (133 mL). Organic layer was concentrated and diluted with isopropanol (67 mL).

Solution of D-(+)-malic acid (10.3 g, 77 mmol) in isopropanol (67 ml) was prepared. A 500 mL flask was charged with isopropanol (20 ml) and D-malic acid salt of product (200 mg, 1.0 wt %) as seed. The resulting suspension was warmed to 35° C. D-Malic acid and primary amine solutions were added simultaneously to the suspension in the 500 mL flask. The slurry was allowed to stir to room temperature, filtered and the cake was washed with 1:2 isopropanol:tert-butyl methyl ether (90 mL) followed by tert-butyl methyl ether (90 mL). After drying under N$_2$, 28.35 g of white crystals of the product were obtained (80% isolated yield from alkoxyketone, 99.95:0.05 dr, 99.8 LCAP by HPLC).

Step B: Preparation of Hydroxysuccinimide

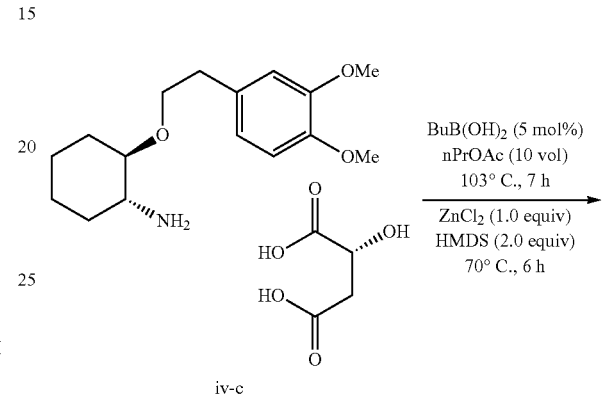

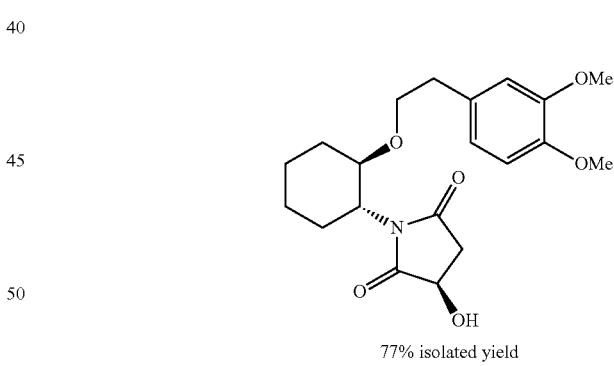

77% isolated yield

To a 50 mL 3-neck flask equipped with overhead stirring, a reflux condenser, a nitrogen inlet, and a thermocouple were added primary amine D-malate salt (3.00 g, 7.07 mmol), n-butylboronic acid (0.036 g, 0.353 mmol, 5 mol %), and n-propyl acetate (30.0 ml, 10 vol). The reaction was heated to reflux over 15 min (bath temperature 110° C.). After 7 hours, a distillation head was connected to the reaction flask. 15 mL of solvent was removed by distillation over 30 minutes to affect removal of water. The distillation head was then removed.

After an additional 3 hours, the temperature was set to 70° C. At this time HPLC analysis showed 96% conversion of the malic acid salt to a 7:1.5:1 mixture of the amido acids and the succinimide. Hexamethyldisilazane (HMDS) (2.95 ml, 14.13 mmol, 2.0 equiv) was added (note: gas evolution and a mild exotherm were observed), followed by anhydrous zinc chloride (0.963 g, 7.07 mmol, 1.0 equiv) (note: a mild exotherm was observed). The temperature was maintained at 70° C. for 6 hours, after which HPLC analysis showed 98.2% conversion of the amides to the succinimide.

The mixture was then allowed to cool to 50° C. 1 M aqueous hydrochloric acid (15 mL, 5 vol) was added over 5 minutes, forming a clear biphasic solution. The phases were cut at 50° C. Subsequently, the organics were washed with additional 1 M aqueous hydrochloric acid (6 mL, 2 vol), with the cut again performed at 50° C. Total aqueous losses were 3.1%, and the assay yield of succinimide in the organics was 85%.

The organics were concentrated twice from n-propyl acetate (15 mL, 5 vol) to remove water. The resulting solid was suspended in n-propyl acetate to a total volume of 15 mL. The mixture was warmed to 60° C. to affect dissolution, then cooled to 45° C., at which point seed crystals (1 wt %) were added. The mixture was cooled to 22° C. over 3 hours. Heptane (18 mL, 6 vol) was added over 6 hours. The mixture was cooled to 2° C. over 4 hours, and the crystals were collected by filtration. The filter cake was washed with heptane (12 mL, 4 vol) and dried to constant weight by nitrogen flowthrough. 2.23 g (77% yield) of white plates were obtained with 94 wt % purity and 94.9 LCAP. Combined liquor losses were 3.1%.

Step C: Reduction and Isolation of the HCl Salt of Compound A

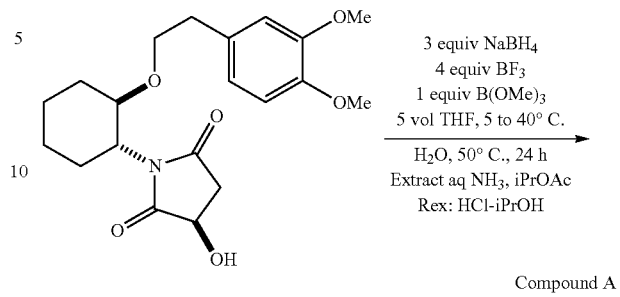

Compound A

To a mixture of hydroxysuccinimide (10.0 g) and sodium borohydride (2.89 g, 3.0 equiv) in tetrahydrofuran (50 mL, 5 vol) at 0° C. in a 200 mL 3-neck flask was added trimethylborate (B(OMe)$_3$, 2.8 mL, 1.0 equiv) over 5 min. After stirring at ambient temperature for 30 min, boron trifluoride etherate (BF$_3$OEt$_2$, 12.6 mL, 4.0 equiv) was added over 1 h at 0° C. This slurry was aged at ambient temperature for 2 h prior to heating at 40° C. for 17 h (~99% cony already after 2 h at 40° C.).

The resulting slurry was then cooled to 0° C. and quenched with water (50 mL, 5 vol) below +10° C. This solution was then heated at 50° C. for 24 h (>99% cony). The resulting solution was diluted with iPrOAc (100 mL, 10 vol) and 28% aqueous ammonia (25 mL, 2.5 vol). After a 50° C. phase cut, the organic layer was washed with water (20 ml, 2 vol) and concentrated to 3 vol iPrOAc. iPrOH (30 mL, 3 vol) was added followed by 5 M HCl in iPrOH (4.1 mL, 1.0 equiv) over 1 h at 20° C. The resulting slurry was aged at room temperature for 14 h, cooled to 0° C. for 4 h and then filtered. Cake was washed with iPAc (50 mL, 5 vol) and dried under nitrogen to give 9.58 g of Compound A HCl salt (98% yield, 99.5 LCAP).

What is claimed is:

1. A process for preparing compounds of Formula I:

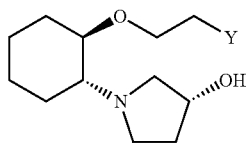

where Y is selected from 3,4-dimethoxyphenyl, 3,4-dihydroxyphenyl or a 3,4-dihalophenyl, comprising the steps of:

a) Mixing a cyclohexyl amine (iv)

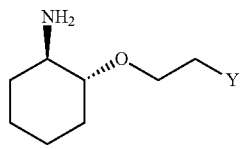

with a malic acid derivative (v)

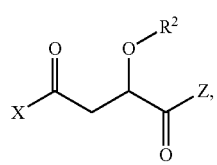

where $R^2$ is selected from hydrogen, esters, carbonates, carbamates, silyl ethers, phosphates or sulfates and where X and Z are independently selected from OH, $C_1$-$C_6$ alkoxy, esters, halides or O-acyl, said X and Z may ontionally be ioined to form a ring (v-a)

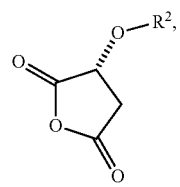

to obtain a hydroxy succinimide (vi)

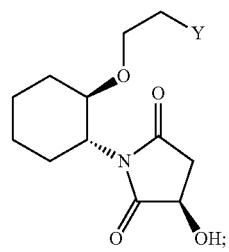

b) isolating the hydroxy succinimide (vi) to provide an isolated hydroxy succinimide (vi); and c) reducing the isolated hydroxy succinimide (vi) to obtain a compound of Formula I.

2. The process of claim 1 comprising the steps of:

a) mixing an alkoxy ketone (iii)

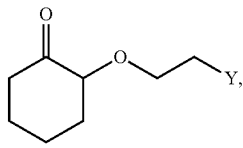

where Y is selected from 3,4-dimethoxyphenyl, 3,4-dihydroxyphenyl or a 3,4-dihalophenyl, with a co-factor, a transaminase polypeptide and an amine to produce a cyclohexyl amine (iv)

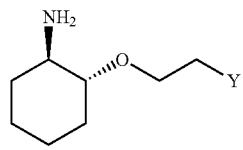

b) mixing the cyclohexyl amine (iv) with a malic acid derivative (v)

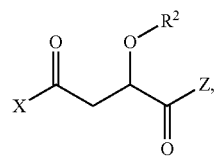

where $R^2$ is selected from hydrogen, esters, carbonates, carbamates, silyl ethers, phosphates or sulfates, and where X and Z are independently selected from OH, $C_1$-$C_6$ alkoxy, esters, halides or O-acyl, said X and Z may optionally be joined to form a ring (v-a)

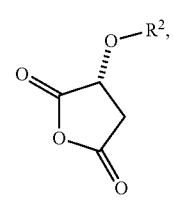

to obtain a hydroxy succinimide (vi)

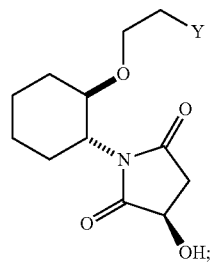

and c) reducing the isolated hydroxy succinimide (vi) to obtain a compound of Formula I.

3. The process of claim 1 comprising the steps of:

a) mixing a substituted cycloalkanone (i)

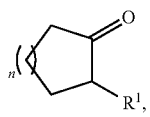

where $R^1$ is an activated leaving group and integer n is selected from 1, 2, or 3 b) with a substituted ethanol (ii)

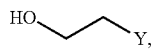

where Y is selected from 3,4-dimethoxyphenyl, 3,4-dihydroxyphenyl or a 3,4-dihalophenyl, in the presence of a metal salt and an organic base to form a cycloalkanone of structure

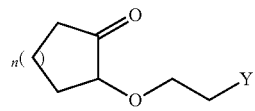

where when n is 1 the cycloalkanone is ring expanded and when n is 3 the cycloalkanone is ring contacted, to provide an alkoxy ketone (iii)

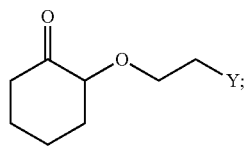

c) mixing the alkoxy ketone (iii) with a co-factor, a transaminase polypeptide and an amine to produce a cyclohexyl amine (iv)

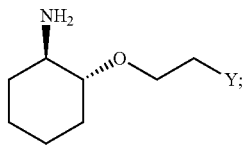

d) mixing the cyclohexyl amine (iv) with a malic acid derivative (v)

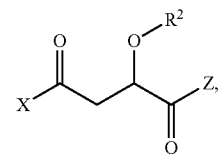

where $R^2$ is selected from hydrogen, esters, carbonates, carbamates, silyl ethers, phosphates or sulfates, and where X and Z are independently selected from OH, C1-C6 alkoxy, esters, halides or O-acyl, said X and Z may optionally be joined to form a ring (v-a)

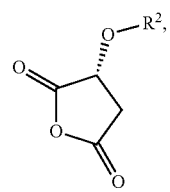

to obtain a hydroxy succinimide (vi)

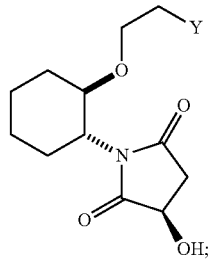

and e) reducing the isolated hydroxy succinimide (vi) to obtain a compound of Formula I.

4. The process of claim 3 which further comprises in step b) mixing the alkoxy ketone (iii) with the co-factor, and a slurry containing the transaminase polypeptide in a basic buffer and an amine.

5. The process of claim 4, which further comprises adding an acid activator to step c.

6. The process of claim 5, which further comprises adding a metal hydride to the hydroxy succinimide (vi) to obtain a compound of Formula I.

7. The process of claim 1, comprising the steps of:
a) Mixing a substituted ethanol (ii)

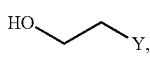

where Y is selected from 3,4-dimethoxyphenyl, 3,4-dihydroxyphenyl or a 3,4-dihalophenyl, with a zinc salt, a secondary amine and an organic base in a first solvent;
b) Adding a solution of a substituted cycloalkanone (i)

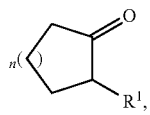

where R$^1$ is an activated leaving group and integer n is 2, to obtain a mixture;
c) Heating the mixture to about 60 to about 150° C. and then cooling the mixture to less than about 60° C.;
d) Adding an acidic aqueous solution to create a biphasic mixture and discarding the aqueous phase;
e) Adding a second solvent to obtain an alkoxy ketone (iii)

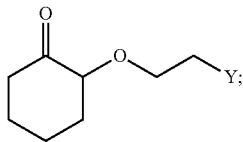

f) Mixing a co-factor with a slurry of a transaminase polypeptide in a basic buffer and a primary amine to produce a solution;
g) Adding the alkoxy ketone (iii) in a second solvent to the solution of step f);
h) Adding a third solvent to create a biphasic mixture and discarding the aqueous layer;
i) Washing the organic layer from step h) with a basic aqueous solution and discarding the aqueous layer;
j) Performing a solvent switch from the third solvent to a fourth solvent;
k) Adding an acid to create a slurry;
l) Filtering the slurry to obtain cyclohexyl amine salt (iv-a);
m) Adding the cyclohexyl amine salt (iv-a) to a mixture of a first solvent and a basic aqueous solution and discarding the aqueous layer;
n) Adding a malic acid derivative, which is selected from malic acid or (v-a)

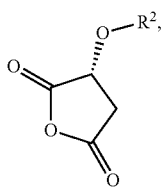

in a first solvent to the cyclohexyl amine (iv-a) in a first solvent;

o) Adding an acid activator;
p) Adding a fourth solvent to obtain hydroxy succinimide (vi)

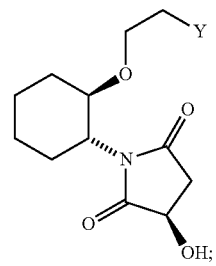

q) Mixing a metal hydride, an additive and an acid, which is selected from a Lewis acid or a protic acid, with a solution of the isolated hydroxy succinimide (vi);
r) Adding a fifth solvent and a basic aqueous solution to obtain a biphasic mixture and discarding the aqueous layer to obtain Compound A

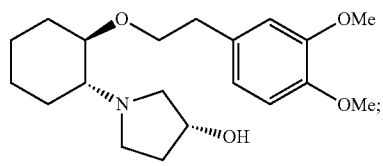

and
s) Adding an acid to obtain the salt of Compound A.
8. The process of claim 1, where a transaminase polypeptide having an amino acid sequence of SEQ ID NO: 18 or SEQ ID NO: 206 is used.
9. The process of claim 1, where a transaminase polypeptide having a polynucleotide sequence of SEQ ID NO: 17 or SEQ ID NO: 205 is used.
10. The process of claim 1, comprising the steps of:
a) Mixing 3,4-dimethoxyphenyl ethanol with zinc chloride, diisopropylethylamine and pyrrolidine in toluene;
b) Adding 2-chlorocyclohexanone to obtain a mixture;
c) Adding aqueous hydrochloric acid and discarding the aqueous layer to obtain 2-(3,4-dimethoxyphenyl ethoxy)-cyclohexanone;
d) Adding PLP to a slurry of a transaminase polypeptide having SEQ ID NO: 18 or SEQ ID NO: 206, in sodium tetraborate and isopropylamine to produce a solution;
e) Mixing 2-(3,4-dimethoxyphenyl ethoxy)-cyclohexanone with the solution of step d);
f) Adding a mixture of IPA and MTBE to create a biphasic mixture and discarding the aqueous layer;
g) Performing a solvent switch on the organic layer from the mixture of IPA and MTBE to a fourth solvent, which is selected from sec-butanol or isopropanol, to obtain a solution;
h) Adding a solution of maleic acid in a fourth solvent to the solution of step g) to obtain 2-(3,4-dimethoxyphenylethoxy)-cyclohexylammonium maleate;
i) Mixing 2-(3,4-dimethoxyphenylethoxy)-cyclohexylammonium maleate with a first solvent and a basic aqueous solution and discarding the aqueous layer to obtain 2-(3,4-dimethoxyphenylethoxy)-cyclohexylamine;
j) Adding R-acetoxy malic acid anhydride to 2-(3,4-dimethoxyphenylethoxy)-cyclohexylamine;
k) Adding acetyl chloride;

l) Adding the fourth solvent, which is selected from ethanol or isopropanol, to obtain 1-{2-[2-(3,4-dimethoxyphenyl)-ethoxy]-cyclohexyl}-3-hydroxypyrrolidine-2,5-dione;

m) Mixing 1-{2-[2-(3,4-dimethoxyphenyl)-ethoxy]-cyclohexyl}-3-hydroxypyrrolidine-2,5-dione with sodium borohydride, trimethylborate and an acid, which is selected from BF$_3$OEt$_2$ or BF$_3$THF, in THF;

n) Adding water;

o) Adding a basic aqueous solution, which is selected from sodium hydroxide or ammonia, and IPAc, to obtain a biphasic mixture and discarding the aqueous layer to obtain

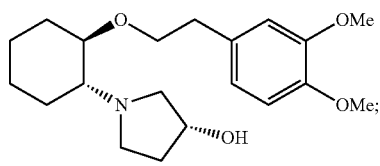 [SMILES: COc1ccc(CCO[C@@H]2CCCC[C@H]2N2CC[C@@H](O)C2)cc1OC]

Compound A and p) Adding hydrochloric acid to obtain the salt of Compound A.

11. The process of claim 10, which further comprises in step e), mixing 2-(3,4-dimethoxyphenyl ethoxy)-cyclohexanone in a second solvent, which is selected from DMSO, ethanol or isopropanol, with the solution of step d).

12. The process of claim 1, comprising the steps of:

a) Mixing a substituted ethanol (ii)

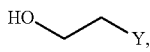

where Y is selected from 3,4-dimethoxyphenyl, 3,4-dihydroxyphenyl or a 3,4-dihalophenyl, with a zinc salt, a secondary amine and an organic base in a first solvent;

b) Adding a solution of a substituted cycloalkanone (i)

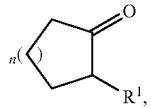

where R$^1$ is an activated leaving group and integer n is 2, to obtain a mixture;

c) Adding an acidic aqueous solution and discarding the aqueous phase to obtain an alkoxy ketone (iii)

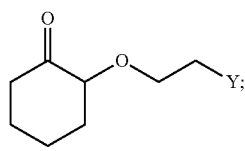

d) Mixing a co-factor with a slurry of a transaminase polypeptide in a basic buffer and a primary amine to produce a solution;

e) Adding the alkoxy ketone (iii) in a second solvent to the solution of step d);

f) Adding a third solvent to create a biphasic mixture and discarding the aqueous layer;

g) Washing the organic layer from step f) with a basic aqueous solution and discarding the aqueous layer;

h) Performing a solvent switch from the third solvent to a fourth solvent;

i) Adding D-malic acid in a fourth solvent to obtain cyclohexyl amine D-malate salt (iv-c)

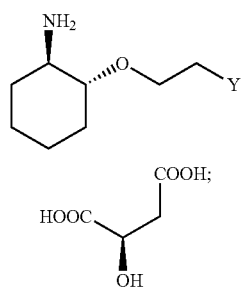

j) Mixing the cyclohexyl amine D-malate salt (iv-c) with a sixth solvent and adding a catalytic amount of an acid activator;

k) Adding HMDS and a Lewis acid to obtain hydroxy succinimide (vi)

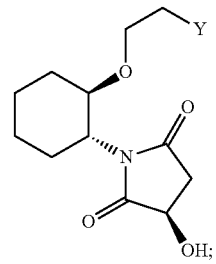

l) Mixing a metal hydride, an additive and an acid, which is selected from a Lewis acid or a protic acid, with a solution of the isolated hydroxy succinimide (vi);

m) Adding a fifth solvent and a basic aqueous solution to obtain a biphasic mixture and discarding the aqueous layer to obtain Compound A

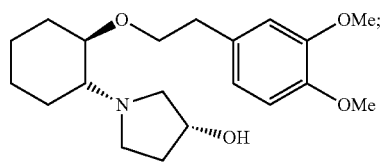

and n) Adding an acid to obtain the salt of Compound A.

13. The process of claim 12, where the cyclohexyl amine D-malate salt (iv-c)

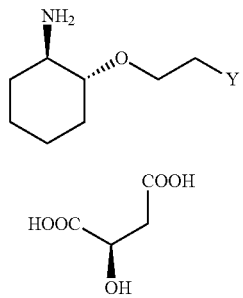

iv-c is isolated as the crystalline form.

14. The process of claim 12, where a transaminase polypeptide having an amino acid sequence of SEQ ID NO: 18 or SEQ ID NO: 206 is used.

15. The process of claim 12, comprising the steps of:
   a) Mixing 3,4-dimethoxyphenyl ethanol with zinc chloride, diisopropylethylamine and pyrrolidine in toluene;
   b) Adding 2-chlorocyclohexanone to obtain a mixture;
   c) Adding aqueous hydrochloric acid and discarding the aqueous layer to obtain 2-(3,4-dimethoxyphenyl ethoxy)-cyclohexanone;
   d) Adding PLP to a slurry of a transaminase polypeptide having SEQ ID NO: 206, in sodium tetraborate and isopropylamine to produce a solution;
   e) Mixing 2-(3,4-dimethoxyphenyl ethoxy)-cyclohexanone with the solution of step d);
   f) Adding a mixture of IPA and MTBE to create a biphasic mixture and discarding the aqueous layer;
   g) Performing a solvent switch on the organic layer from the mixture of IPA and MTBE to a fourth solvent, which is selected from sec-butanol or isopropanol, to obtain a solution;
   h) Adding a solution of D-malic acid in a fourth solvent to the solution of step g) to obtain 2-(3,4-dimethoxyphenylethoxy)-cyclohexylammonium malate;
   i) Mixing 2-(3,4-dimethoxyphenylethoxy)-cyclohexylammonium malate with an ester solvent and adding a catalytic amount of an alkyl boronic acid;
   j) Heating to about 90 to about 125° C., then cooling to about 70° C.;
   k) Adding HMDS and a Lewis acid to obtain 1-{2-[2-(3,4-dimethoxyphenyl)-ethoxy]-cyclohexyl}-3-hydroxy-pyrrolidine-2,5-dione, where said Lewis acid is zinc chloride, iron(II) chloride, lithium chloride, copper(II) trifluoromethanesulfonate, iron(III) chloride, iron(II) bromide, zinc bromide, zinc acetate or zinc trifluoromethanesulfonate;
   l) Mixing 1-{2-[2-(3,4-dimethoxyphenyl)-ethoxy]-cyclohexyl}-3-hydroxypyrrolidine-2,5-dione with sodium borohydride, trimethylborate and an acid, which is selected from BF$_3$OEt$_2$ or BF$_3$THF, in THF;
   m) Adding water;
   n) Adding a basic aqueous solution, which is selected from sodium hydroxide or ammonia, and IPAc, to obtain a biphasic mixture and discarding the aqueous layer to obtain

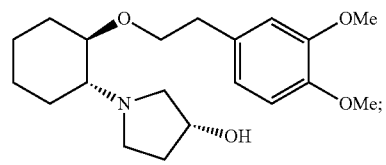

Compound A and
   o) Adding hydrochloric acid to obtain the salt of Compound A.

16. The process of claim 15, where the alkyl boronic acid is methyl boronic acid or butyl boronic acid.

17. The process of claim 15, where the Lewis acid in step k) is zinc chloride.

18. The process of claim 1 comprising the steps of:
   a) Mixing 3,4-dimethoxyphenyl ethanol with zinc chloride, diisopropylethylamine and pyrrolidine in toluene;
   b) Adding 2-chlorocyclohexanone to obtain a mixture;
   c) Adding aqueous hydrochloric acid and discarding the aqueous layer to obtain 2-(3,4-dimethoxyphenyl ethoxy)-cyclohexanone;
   d) Adding PLP to a slurry of a transaminase polypeptide, said transaminase polypeptide having SEQ ID NO: 18 or SEQ ID NO: 206, in sodium tetraborate and isopropylamine to produce a solution;
   e) Mixing 2-(3,4-dimethoxyphenyl ethoxy)-cyclohexanone with the solution of step d);
   f) Adding a mixture of IPA and MTBE to create a biphasic mixture and discarding the aqueous layer;
   g) Performing a solvent switch on the organic layer from the mixture of IPA and MTBE to a fourth solvent, which is selected from sec-butanol or isopropanol, to obtain a solution;
   h) Adding a solution of oxalic acid in the fourth solvent, which is selected from sec-butanol or isopropanol, to the solution of step g to obtain 2-(3,4-dimethoxyphenylethoxy)-cyclohexylammonium oxalate iv-b;
   i) Adding 2-(3,4-dimethoxyphenylethoxy)-cyclohexylammonium oxalate iv-b to a mixture of DMAc and potassium bicarbonate followed by (R)-1,4-dibromo-butan-2-ol;
   j) Adding IPAc and a basic aqueous solution to obtain a biphasic mixture and discarding the aqueous layer to obtain

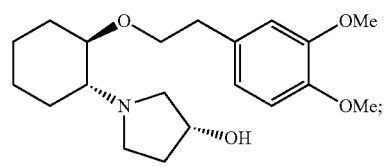

Compound A and
   k) Adding hydrochloric acid to obtain the salt of Compound A.

* * * * *